(12) United States Patent
Novak

(10) Patent No.: US 8,083,746 B2
(45) Date of Patent: Dec. 27, 2011

(54) OPEN WEDGE OSTEOTOMY SYSTEM AND SURGICAL METHOD

(75) Inventor: Vincent P. Novak, Groton, MA (US)

(73) Assignee: Arthrex, Inc., Naples, FL (US)

( * ) Notice: Subject to any disclaimer, the term of this patent is extended or adjusted under 35 U.S.C. 154(b) by 1099 days.

(21) Appl. No.: 11/047,551

(22) Filed: Jan. 31, 2005

(65) Prior Publication Data

US 2005/0273114 A1 Dec. 8, 2005

Related U.S. Application Data

(60) Provisional application No. 60/569,545, filed on May 7, 2004, provisional application No. 60/603,899, filed on Aug. 24, 2004, provisional application No. 60/626,305, filed on Nov. 9, 2004.

(51) Int. Cl.
*A61B 17/58* (2006.01)
(52) U.S. Cl. .......................... 606/88; 606/87
(58) Field of Classification Search .............. 606/79, 606/82, 84, 88, 90; 623/20.32
See application file for complete search history.

(56) References Cited

U.S. PATENT DOCUMENTS

| | | |
|---|---|---|
| 2,737,724 A | 3/1956 | Herz |
| 3,579,777 A | 5/1971 | Milewski |
| 3,750,652 A | 8/1973 | Sherwin |
| 4,349,018 A | 9/1982 | Chambers |
| 4,421,112 A | 12/1983 | Mains et al. |
| 4,501,268 A | 2/1985 | Comparetto |
| 4,523,587 A | 6/1985 | Frey |
| 4,563,489 A | 1/1986 | Urist |
| 4,565,191 A | 1/1986 | Slocum |
| 4,750,481 A | 6/1988 | Reese |
| 4,769,040 A | 9/1988 | Wevers |
| 4,817,794 A | 4/1989 | Workman |
| 4,851,005 A | 7/1989 | Hunt et al. |

(Continued)

FOREIGN PATENT DOCUMENTS

CN 1132067 10/1996

(Continued)

OTHER PUBLICATIONS

Oliver C. Kessler et al., Avoidance of Medial Cortical Fracture in High Tibial Osteotomy: Improved Technique, Clinical Orthopaedics and Related Research, Feb. 2002, pp. 180-185, No. 395.

(Continued)

*Primary Examiner* — Eduardo C Robert
*Assistant Examiner* — Stuart S Bray
(74) *Attorney, Agent, or Firm* — Dickstein Shapiro LLP

(57) ABSTRACT

A system and method for performing an opening wedge osteotomy in a tibia, the system and method comprising (i) a positioning guide configured for aligning a portion of the positioning guide with a joint line of the tibia and for fixing the positioning guide to the tibia; (ii) a cutting guide configured to direct a cutting blade into the tibia so as to form a bone cut therein; (iii) a mechanical jack configured for placement into the bone cut in the tibia so as to distract the tibia at the bone cut; and (iv) a multi-part implant for supporting the open wedge osteotomy in the tibia, with a first component for disposition in a posterior portion of the open wedge osteotomy, a second component for disposition in an anterior portion of the open wedge osteotomy, and a connection device for selectively connecting the components to one another.

13 Claims, 80 Drawing Sheets

U.S. PATENT DOCUMENTS

| | | | |
|---|---|---|---|
| 4,852,558 A | | 8/1989 | Outerbridge |
| 4,892,093 A | * | 1/1990 | Zarnowski et al. ............. 606/82 |
| 4,936,844 A | | 6/1990 | Chandler et al. |
| 4,961,740 A | | 10/1990 | Ray et al. |
| 5,053,039 A | | 10/1991 | Hofmann et al. |
| 5,254,119 A | | 10/1993 | Schreiber |
| 5,275,603 A | | 1/1994 | Ferrante et al. |
| 5,297,538 A | | 3/1994 | Daniel |
| 5,306,276 A | | 4/1994 | Johnson et al. |
| 5,352,229 A | | 10/1994 | Goble et al. |
| 5,413,579 A | | 5/1995 | Du Toit |
| 5,445,640 A | | 8/1995 | Johnson et al. |
| 5,451,228 A | | 9/1995 | Johnson et al. |
| 5,540,695 A | | 7/1996 | Levy |
| 5,569,250 A | | 10/1996 | Sarver et al. |
| 5,601,565 A | | 2/1997 | Huebner |
| 5,609,635 A | | 3/1997 | Michelson |
| 5,613,969 A | | 3/1997 | Jenkins, Jr. |
| 5,620,448 A | | 4/1997 | Puddu |
| 5,640,813 A | | 6/1997 | Glazik et al. |
| 5,662,655 A | | 9/1997 | Laboureau et al. |
| 5,669,909 A | | 9/1997 | Zdeblick et al. |
| 5,674,296 A | | 10/1997 | Bryan et al. |
| 5,681,316 A | | 10/1997 | DeOrio et al. |
| 5,722,978 A | * | 3/1998 | Jenkins, Jr. ............. 606/87 |
| 5,733,290 A | | 3/1998 | McCue et al. |
| 5,749,875 A | | 5/1998 | Puddu |
| 5,766,251 A | | 6/1998 | Koshino |
| 5,843,085 A | | 12/1998 | Graser |
| 5,888,223 A | | 3/1999 | Bray, Jr. |
| 5,911,724 A | | 6/1999 | Wehrli |
| 5,980,526 A | | 11/1999 | Johnson et al. |
| 6,008,433 A | | 12/1999 | Stone |
| 6,027,504 A | | 2/2000 | McGuire |
| 6,039,761 A | | 3/2000 | Li et al. |
| 6,086,593 A | | 7/2000 | Bonutti |
| 6,099,531 A | | 8/2000 | Bonutti |
| 6,102,950 A | | 8/2000 | Vaccaro |
| 6,190,390 B1 | | 2/2001 | McAllister |
| 6,200,347 B1 | | 3/2001 | Anderson et al. |
| 6,203,546 B1 | | 3/2001 | MacMahon |
| 6,214,007 B1 | | 4/2001 | Anderson |
| 6,224,599 B1 | | 5/2001 | Baynham et al. |
| 6,264,694 B1 | | 7/2001 | Weiler |
| 6,277,149 B1 | | 8/2001 | Boyle et al. |
| 6,287,308 B1 | | 9/2001 | Betz et al. |
| 6,379,361 B1 | | 4/2002 | Beck, Jr. et al. |
| 6,423,063 B1 | | 7/2002 | Bonutti |
| 6,461,359 B1 | | 10/2002 | Tribus et al. |
| 6,478,800 B1 | | 11/2002 | Fraser et al. |
| 6,565,570 B2 | | 5/2003 | Sterett et al. |
| 6,575,982 B1 | | 6/2003 | Bonutti |
| 6,699,252 B2 | | 3/2004 | Farr, II et al. |
| 6,743,255 B2 | | 6/2004 | Ferree |
| 6,755,841 B2 | | 6/2004 | Fraser et al. |
| 6,796,986 B2 | | 9/2004 | Duffner |
| 6,823,871 B2 | * | 11/2004 | Schmieding ............. 128/898 |
| 2002/0010513 A1 | * | 1/2002 | Schmieding ............. 623/23.72 |
| 2002/0029084 A1 | | 3/2002 | Paul et al. |
| 2002/0095156 A1 | | 7/2002 | Kuras et al. |
| 2002/0133157 A1 | * | 9/2002 | Sterett et al. ............. 606/69 |
| 2003/0028197 A1 | | 2/2003 | Hanson et al. |
| 2003/0105526 A1 | * | 6/2003 | Bryant et al. ............. 623/16.11 |
| 2003/0171757 A1 | | 9/2003 | Coon et al. |
| 2003/0195516 A1 | | 10/2003 | Sterett et al. |
| 2003/0199881 A1 | | 10/2003 | Bonutti |
| 2004/0039387 A1 | | 2/2004 | Gause et al. |
| 2005/0075641 A1 | | 4/2005 | Singhatat et al. |
| 2005/0216090 A1 | | 9/2005 | O'Driscoll et al. |
| 2005/0228498 A1 | | 10/2005 | Andres |
| 2005/0251147 A1 | | 11/2005 | Novak |
| 2005/0273115 A1 | | 12/2005 | Coon et al. |
| 2006/0106396 A1 | | 5/2006 | Justin et al. |
| 2006/0122617 A1 | | 6/2006 | Lavallee et al. |
| 2006/0129163 A1 | | 6/2006 | McGuire |
| 2006/0149274 A1 | | 7/2006 | Justin et al. |
| 2006/0149275 A1 | | 7/2006 | Cadmus |
| 2006/0217808 A1 | | 9/2006 | Novak et al. |
| 2006/0241636 A1 | | 10/2006 | Novak et al. |
| 2007/0016209 A1 | | 1/2007 | Ammann et al. |

FOREIGN PATENT DOCUMENTS

| | | |
|---|---|---|
| CN | 1181696 | 5/1998 |
| EP | 1 099 428 | 5/2001 |
| EP | 1669033 | 6/2006 |
| FR | 2741525 | 5/1997 |
| FR | 2 764 183 | 12/1998 |
| WO | WO 96/14802 | 5/1996 |
| WO | WO 99/52473 | 10/1999 |
| WO | WO 2005/048888 | 6/2005 |
| WO | WO 2006/107800 | 10/2006 |

OTHER PUBLICATIONS

Sohn, Meniscus Transplantation: Current Concepts, The Journal of Knee Surgery, Apr. 2008, pp. 163-172, vol. 21, No. 2.

* cited by examiner

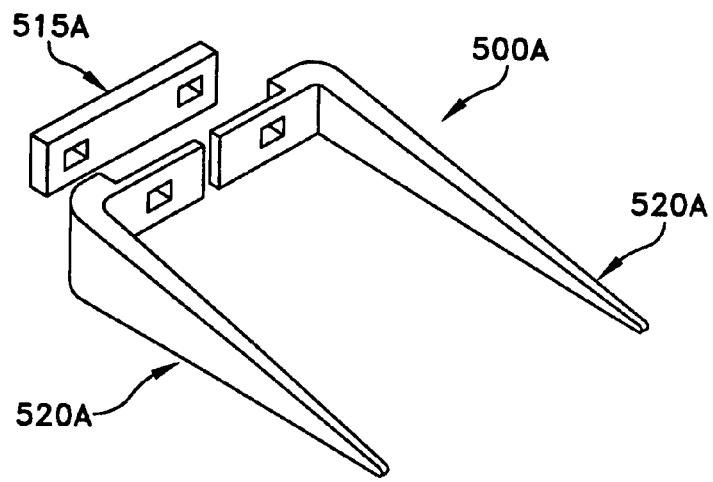
FIG. 79
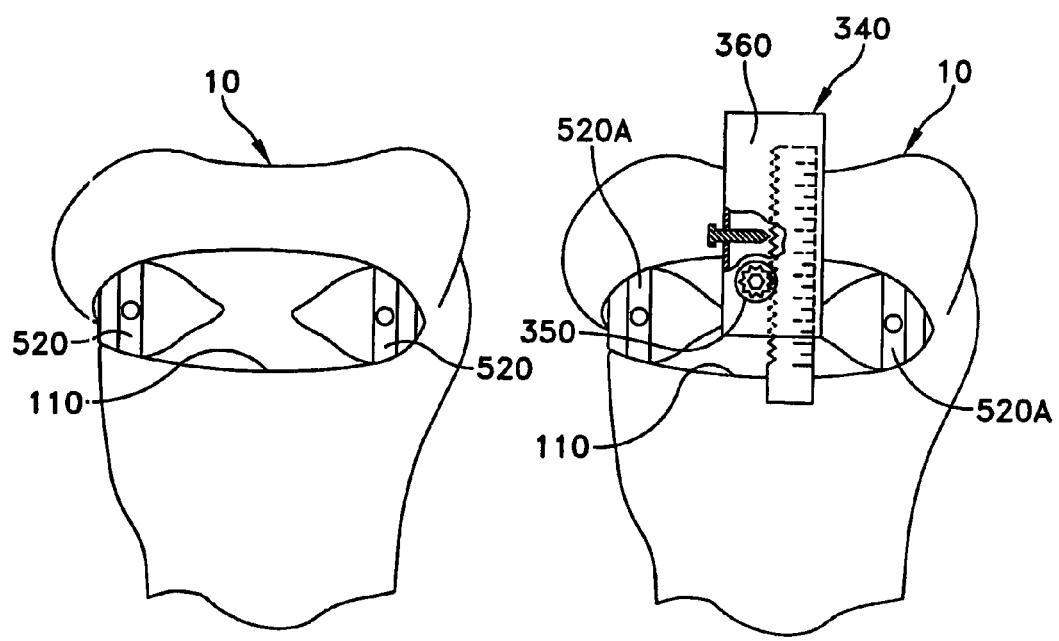
FIG. 81
FIG. 80

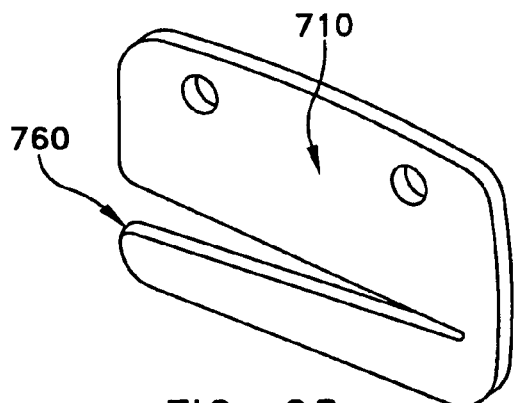
FIG. 98
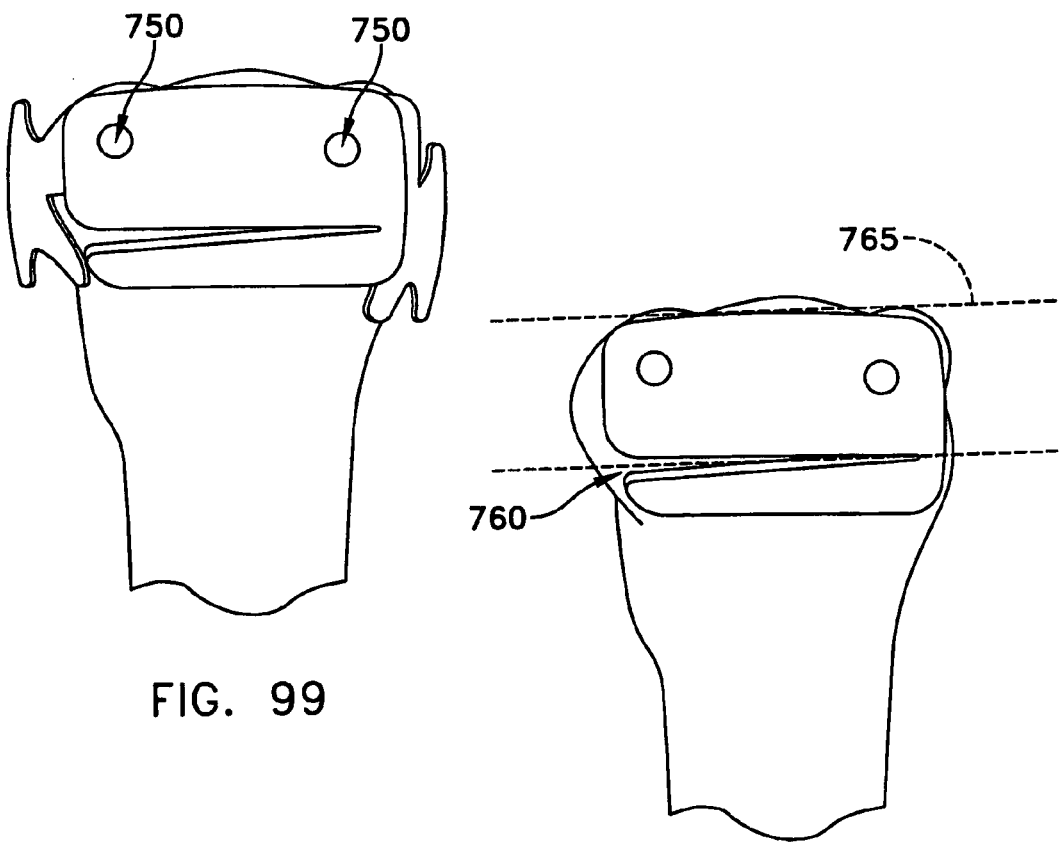
FIG. 99
FIG. 100

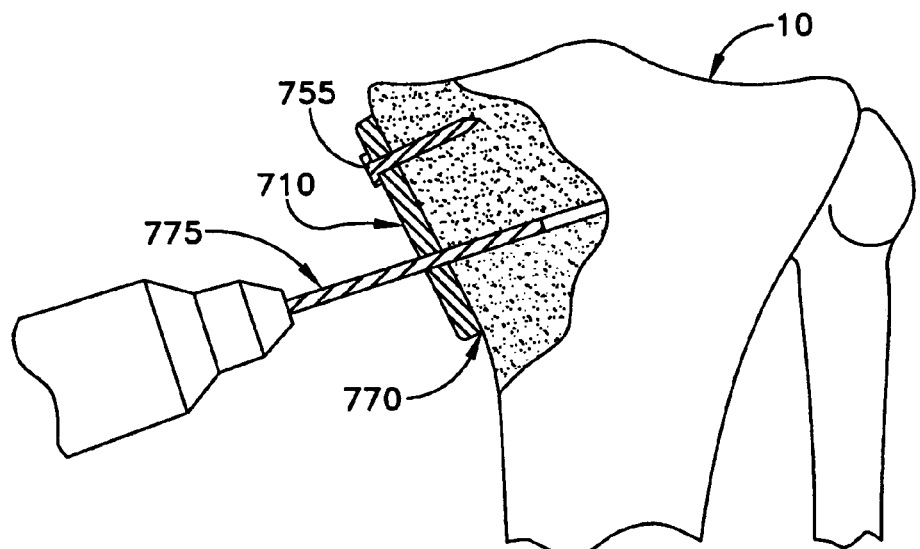
FIG. 101
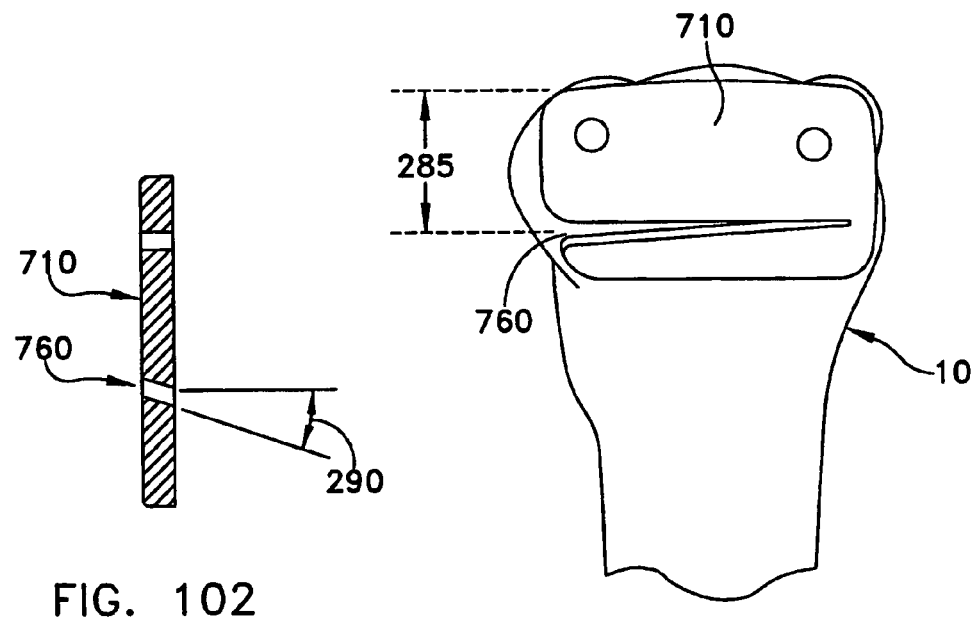
FIG. 102
FIG. 103

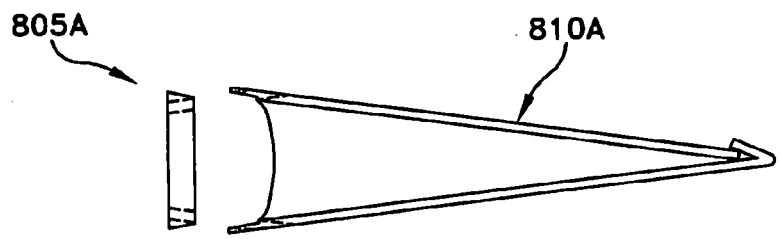
FIG. 121
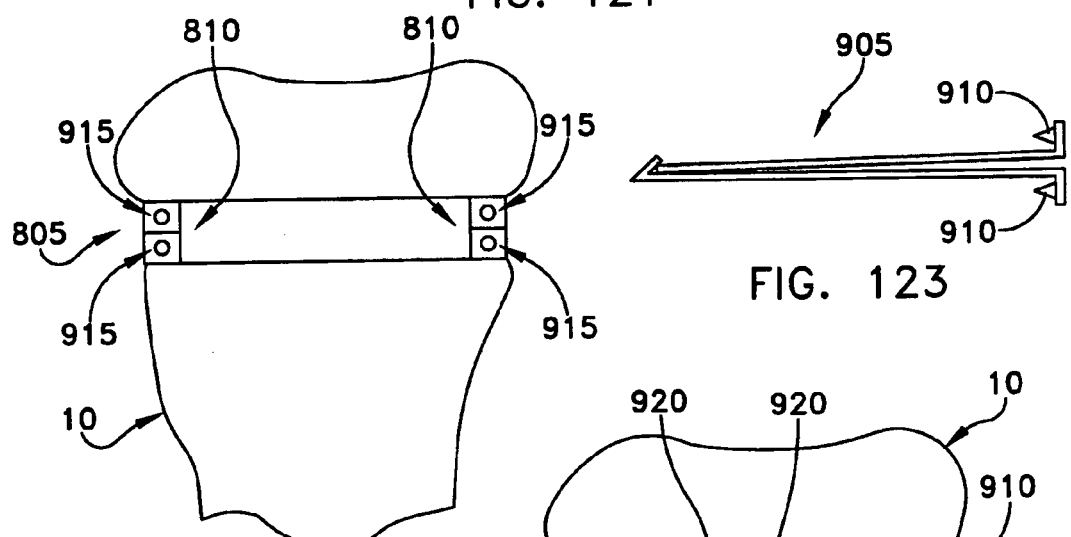
FIG. 122  FIG. 123
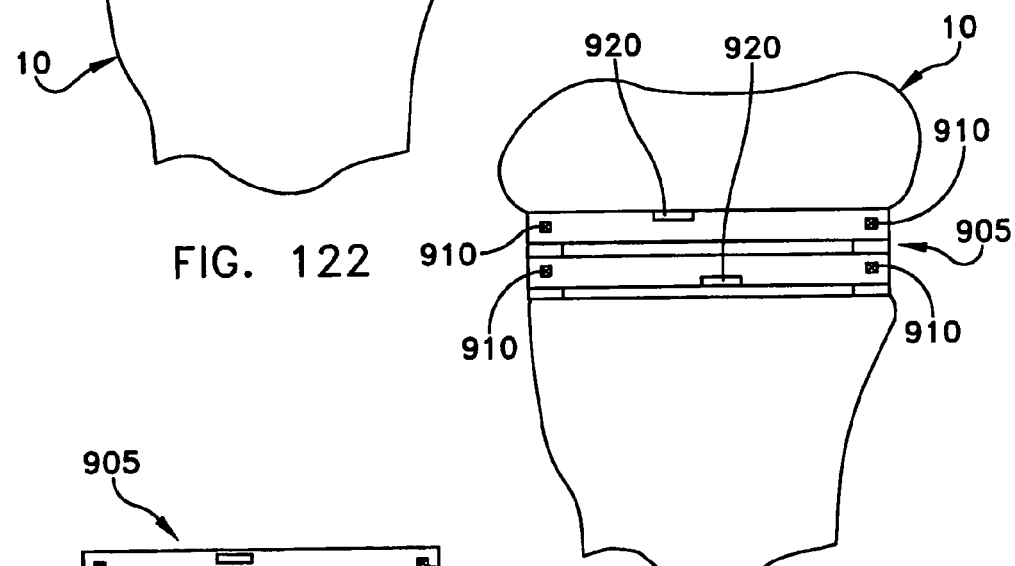
FIG. 124
FIG. 125

OPEN WEDGE OSTEOTOMY SYSTEM AND SURGICAL METHOD

REFERENCE TO PENDING PRIOR PATENT APPLICATIONS

This patent application claims benefit of:
(1) prior U.S. Provisional Patent Application Ser. No. 60/569,545, filed May 7, 2004 by Vincent P. Novak for OPEN WEDGE OSTEOTOMY SYSTEM AND SURGICAL TECHNIQUE;
(2) prior U.S. Provisional Patent Application Ser. No. 60/603,899, filed Aug. 24, 2004 by Vincent P. Novak for OPEN WEDGE OSTEOTOMY SYSTEM AND SURGICAL TECHNIQUE; and
(3) prior U.S. Provisional Patent Application Ser. No. 60/626,305, filed Nov. 9, 2004 by Vincent P. Novak for OPEN WEDGE OSTEOTOMY SYSTEM AND SURGICAL TECHNIQUE.

The three above-identified patent applications are hereby incorporated herein by reference.

FIELD OF THE INVENTION

This invention is related to surgical apparatus and methods in general, and more particularly to apparatus and methods for open wedge osteotomy surgery.

BACKGROUND OF THE INVENTION

Osteotomies about the knee have been an important component of the surgical treatment in the management of knee osteoarthritis. The ultimate goal of knee osteotomies has been to relieve pain symptoms, slow disease progression and postpone total knee arthroplasty in younger patients by transferring weight bearing load to the relatively unaffected portions of the knee.

The most commonly performed knee osteotomy has been the proximal tibial osteotomy or "high tibial" osteotomy. The first reported tibial osteotomy was in 1958. Knee osteotomy principles and techniques continued to evolve through the 1960s and 1970s. Today, however, other than at a minority of leading orthopedic centers, proximal tibial osteotomies are generally regarded critically by the general populace of orthopedic surgeons. The overall community holds the opinion that, first and foremost, the surgical technique of osteotomy is challenging and cumbersome, requiring much practice in the "art" in order to effectively perform and reproduce the osteotomy procedure.

More particularly, current techniques generally require the passage of hand-directed guidewires and hand-guided bone resecting tools while requiring continual use of fluoroscopy throughout the procedure. In such a procedure, the failure to properly execute the required precision can lead to a lack of, or postoperative loss of, correction and complications such as delayed union or nonunion, unintended changes to the slope of the tibial plateau, intraarticular fractures, and neurovascular problems. All of these issues pose a direct risk to a successful surgical outcome. In addition, the postoperative rehabilitation period using current techniques may require a conservatively long duration so as to protect the osteotomy from potential nonunion during the long healing period. Also, currently practiced procedures often require a second surgery to remove fixation hardware.

The reported long-term surgical outcomes of high tibial osteotomy procedures vary considerably. Published research of these procedures demonstrates that the relief of pain and restoration of function is generally achieved in approximately 80% to 90% of patients at five years, and 50% to 65% of patients at ten years.

The methods and principles of surgically performing an osteotomy have slowly developed over time. The two common osteotomy methods are: (i) the lateral closing wedge method; and (ii) the medial opening wedge method (with either an internal fixation device or an external fixation device). Within these two general categories of surgical methods, there are varying nuances to the surgical techniques purported by individual orthopedic surgeons. For example, in discussions with individual surgeons, it is common to hear "this is how I do it" inasmuch as no "gold standard" surgical technique has emerged to date.

The lateral closing wedge method has been the traditional method for osteotomy surgery. This is the most common osteotomy for medial compartment osteoarthritis. Correction of alignment is typically achieved by first removing a laterally-based, angled wedge of bone, and then closing the resultant opening.

The medial opening wedge method with internal fixation has been gaining in popularity in recent years. Correction of alignment is typically achieved by first making a single transverse bone cut into the medial sagittal plane of the knee, and then manually opening the cut under fluoroscopy with a series of osteotomes, or pre-sized wedge osteotomes. This technique generally provides the surgeon with the intraoperative ability to more easily achieve the required correction angle. The wedge opening is then fixated at a given height with a small fixation plate and bone screws that support the opening of the wedge osteotomy. The opened bony void is then filled with bone graft material.

The medial opening wedge method with an external fixation device is most often used when a large correction is needed in order to achieve proper alignment. Correction of alignment is achieved by first making a single bone cut into the medial sagittal plane of the knee. Next, an external fixation device is applied and then regularly adjusted, in small increments, usually on a daily basis, so as to slowly open the wedge to a desired correction angle. The progress of this surgical technique is usually confirmed with weekly radiographs.

The opening wedge technique has been advocated as a faster, simpler surgical procedure that can be more easily learned while providing a better method for achieving the desired corrective angle with minimal risks to surrounding neurovascular structures. However, the various opening wedge surgical techniques, as currently practiced, allow a wide window for the introduction of surgical error.

All of these opening wedge osteotomy techniques, as currently practiced, require the hand-guided placement of guide pins to define the anterior-to-posterior tibial slope, sometimes referred to as the AP tibial slope, and require the use of hand-held and hand-guided osteotomes, which are all used under fluoroscopy. The use of frequent fluoroscopic pictures is critical to determine the work performed to that point in the procedure and the required adjustments still to be made in the remainder of the procedure. Errors by the surgeon in defining the AP tibial slope can result in an inappropriately-placed osteotomy with unintended changes to the tibial slope, which in turn may affect knee stability. Errors in the use of hand-driven osteotomes or hand-guided saw blades in creating the bone cut can lead to tibial slope changes, migration of the osteotomy into the joint, and/or injury to neurovasculature and soft tissue structures.

Recent evolutionary developments in osteotomies have focused on two general components. One of these includes improved wedge-shaped osteotomes which are used to form or open the bony wedge osteotomy. The other includes low profile internal fixation plates used during the nonweight-bearing rehabilitation phase to rigidly maintain the wedge opening, and used during the weight-bearing rehabilitation phase to add support to the entire osteotomy site. While significant, these advances do not address important issues including, but not limited to, the reduction of the surgical learning curve to make the procedures more reproducible, the improvement of the surgical precision of osteotomy procedures, the reduction in the use of fluoroscopy, and the fact that internal fixation devices used in an open wedge osteotomy effectively stress-shield the osteotomy or fracture site. Such stress-shielding is often a factor in complications involving nonunion and loss of correction.

Today, the orthopedic surgeon's requirements are demanding prior to the adoption of a new surgical procedure. The actual demands include a predictive knee osteotomy procedure with accuracy in determining the correction angle before surgery, and precision in carrying out the surgical technique with reproducible results. The ultimate surgical outcome depends upon the ability of the surgeon to precisely execute the corrective angle and to ensure that the correction remains long lasting.

EXAMPLE OF DEFICIENCIES OF THE PRIOR ART

In current surgical practice, if the surgeon desires to institute a desired change in the AP slope (either a change planned from pre-operative x-rays or a change required from intra-operative bone cuts during a routine knee osteotomy), the surgeon is faced with various options to help re-adjust the slope of the bone.

First, the surgeon can place additional bone graft material or solid pieces of bone graft (i.e., allograft bone or synthetic bone) into the osteotomy void, at a specific location within the void, to help re-adjust the AP slope. However, this practice of "shimming" is frequently difficult to estimate and calculate during surgery.

Second, and referring to FIG. 1, the surgeon can use a fixation plate 5 that provides a specific AP slope change to tibia 10. The difficulty with this approach is the fact that fixation plate 5 only directly supports a portion of the wedge void 15. A potential complication exists wherein even small weight-bearing forces may act upon the slope of the bone and affect the planned slope adjustment in the least supported areas.

Third, the surgeon may both (i) place solid pieces of bone graft (i.e., allograft bone or synthetic bone) into the osteotomy void, at a specific location within the void, to help re-adjust the AP slope and, in addition, (ii) utilize a fixation plate 5. Again, this combined approach suffers from the aforementioned shimming and fixation plate problems.

There are also other issues with the three above-identified options. First, although the exact measurement of an AP slope change may be determined pre-operatively, the execution of a planned change is generally still carried out with intra-operative adjustments due to offset cutting planes which require subsequent shims and perhaps re-estimation of the desired sloped fixation plate. Second, even if the surgeon's intention is not to affect the AP tibial slope, the current practice of knee osteotomy almost always ensures that it will be affected somewhat. With the antero-medial approach, this is due to the offset cutting plane and the opening of the osteotomy void. The surgeon must then make intra-operative adjustments with shims and a sloped fixation plate, changes that are visually estimated and not pre-determined from superior pre-operative radiographic means. Third, inaccuracies in carrying out adjustments to the AP slope may result in immediate poor results following surgery, or the eventual loss of correction adversely affecting long-term outcomes.

OBJECTS OF THE INVENTION

Accordingly, one object of the present invention is to provide an improved open wedge osteotomy system that is instrument-guided and modular in fashion.

Another object of the present invention is to reduce the overall surgeon learning curve in performing an open wedge osteotomy procedure.

Another object of the present invention is to provide an improved open wedge osteotomy system that allows a more surgically reproducible procedure and reduces surgical error.

A still further object of the present invention is to provide an improved open wedge osteotomy system that allows the procedure to be performed more quickly.

Another object of the present invention is to provide an improved open wedge osteotomy system that reduces or eliminates the need for fluoroscopy during the procedure.

A further object of the present invention is to provide an improved open wedge osteotomy system that defines the anterior-to-posterior tibial slope from visual inspection, and enables marking of the natural anterior-to-posterior joint line without the use of radiographic imaging.

A still further object of the present invention is to provide an improved open wedge osteotomy system that accurately executes pre-operative measurements.

A further object of the present invention is to provide an improved open wedge osteotomy system in which the natural joint line is marked by the positioning and fixation of a guide device on which a system of bone cutting guides is attached, whereby to reliably provide a transverse cut through the bone according to the physician's pre-operative calculations.

A still further object of the present invention is to provide an improved open wedge osteotomy system that accurately defines the cutting plane in relation to the AP tibial slope.

A still further object of the present invention is to provide an improved open wedge osteotomy system that maintains a consistent angled cutting plane from the posterior aspects of the bone to the anterior aspects of the bone, and that passes through the sagittal plane during bone resection.

A still further object of the present invention is to provide an improved open wedge osteotomy system that accurately opens the osteotomy void to the desired angle while decreasing the risks of changing the AP tibial slope and the risk of bone fracture.

Another object of the present invention is to provide an improved open wedge osteotomy system that reduces or eliminates the use of static internal fixation plates and screws.

Another object of the present invention is to provide an improved open wedge osteotomy system that better promotes the physiologic growth of bone across the osteotomy site.

Another object of the present invention is to provide a multi-part implant system that rims the periphery of the osteotomy void, allowing for the containment of various bone graft materials while supporting the reoriented bone segments.

A still further object of the present invention is to provide a multi-part implant system for custom assembly in-situ by a surgeon.

A still further object of the present invention is to provide a method for creating an osteotomy in which a multi-part implant is introduced into the osteotomy void part by part, so as to facilitate a minimally invasive procedure, and wherein the implant parts are subsequently assembled in-situ by the surgeon.

A still further object of the present invention is to provide a multi-part implant system that allows graft materials to be optimally compacted or inserted within the osteotomy void and contained by the multi-part implant system.

A still further object of the present invention is to provide a multi-part implant system in which implant parts of varying measurements are assembled together in order to enable accurate adjustments to the AP tibial slope.

A still further object of the present invention is to provide a multi-part implant system that accurately maintains and supports the tibial plateau at a desired slope from its anterior aspect to its posterior aspect.

A still further object of the present invention is to provide a multi-part implant system in which the implant parts support the periphery of bone and the subsequent passage of screws or fastener devices through the implant parts and into surrounding bone secures the multi-part implant in place.

A still further object of the present invention is to provide a multi-part implant system in which channels lead to the surface interface between the implant and the host bone, whereby to facilitate the directed injection of bone glues, cements, biologic materials or grafting materials.

A still further object of the present invention is to provide a multi-part implant system in which two implant parts comprise different biomaterials, biocomposites or formulations thereof, so as to allow for different rates of selective resorption of the implant parts.

A still further object of the present invention is to provide an osteotomy system in which a positioning guide is positioned on top of the skin and percutaneously fixed to the tibia so as to provide a minimally invasive osteotomy.

SUMMARY OF THE INVENTION

With the above and other objects in view, in one form of the invention, there is provided a positioning guide for performing an opening wedge osteotomy in a tibia, the positioning guide comprising an alignment component for aligning a portion of the positioning guide with a joint line of the tibia, a fixation component for fixing the positioning guide to the tibia, and a connection component for connecting the positioning guide to a cutting guide.

In another form of the invention, there is provided a cutting guide for performing an opening wedge osteotomy in a tibia, the cutting guide having a guide attachment component for selective attachment of the cutting guide to the tibia, the cutting guide forming an angled cutting slot therein configured to direct a cutting blade into the tibia so as to form a bone cut therein.

In another form of the invention, there is provided an anterior protector member and a posterior protector member for performing an opening wedge osteotomy, each of the anterior protector member and the posterior protector member having a first end, a second end and a given length between the first end and the second end, the first end of the anterior protector member and the posterior protector member each having a connector portion configured for anchoring to the tibia, the anterior protector member and the posterior protector member each having a contoured shape to closely approximate an anterior aspect and a posterior aspect of the tibia, respectively, wherein the second end of the anterior protector member and the second end of the posterior protector member are each inserted around the tibia from the medial aspect toward the anterior aspect and the posterior aspect, respectively, and the first end of the anterior protector member and the first end of the posterior protector member are each anchored to the tibia.

In another form of the invention, there is provided a mechanical jack for performing an opening wedge osteotomy in a tibia, the mechanical jack comprising a jack attachment component for selective attachment of the jack to the tibia, the mechanical jack having a pair of plates with a first end and a second end in opposition to one another, the first end of the pair of plates configured to remain substantially together with one another and configured for placement into the bone cut in the tibia, and the second end of the pair of plates configured for selective positioning (i) from a first position with the second ends of the pair of plates substantially together with one another, (ii) to a second position with the second ends of the pair of plates apart from one another so as to distract the tibia at the bone cut.

In another form of the invention, there is provided a system for performing an opening wedge osteotomy in a tibia, the system comprising:

a positioning guide having an alignment component for aligning a portion of the positioning guide with a joint line of the tibia, and a fixation component for fixing the positioning guide to the tibia;

a cutting guide having a guide attachment component for selectively attaching the cutting guide to the positioning guide, the cutting guide forming an angled cutting slot therein configured to direct a cutting blade into the tibia so as to form a bone cut therein;

a mechanical jack having a jack attachment component for selectively attaching the jack to the positioning guide, the mechanical jack having a pair of plates with a first end and a second end in opposition to one another, the first end of the pair of plates configured to remain substantially together with one another and configured for placement into the bone cut in the tibia, and. the second end of the pair of plates configured for selective positioning (i) from a first position with the second ends of the pairs of plates substantially together with one another, (ii) to a second position with the second ends of the pair of plates apart from one another so as to distract the tibia at the bone cut; and a multi-part implant for supporting the open wedge osteotomy in the tibia, the multi-part implant having a first component for disposition in a posterior portion of the open wedge osteotomy, a second component for disposition in an anterior portion of the open wedge osteotomy, and a connection device for selectively connecting the first component and the second component to one another.

In another form of the invention, there is provided a method for performing an opening wedge osteotomy in a tibia, the method comprising:

providing a system for performing the opening wedge osteotomy in the tibia, the system comprising:

a positioning guide having an alignment component for aligning a portion of the positioning guide with a joint line of the tibia, and a fixation component for fixing the positioning guide body to the tibia;

a cutting guide having a guide attachment component for selectively attaching the cutting guide to the positioning guide, the cutting guide forming an angled cutting slot therein configured to direct a cutting blade into the tibia so as to form a bone cut therein;

a mechanical jack having a jack attachment component for selectively attaching the jack to the positioning guide, the mechanical jack having a pair of plates with a first end and a second end in opposition to one another, the first end of the pair of plates configured to remain substantially together with one another and configured for placement into the bone cut in the tibia, and the second end of the pair of plates configured for selective positioning (i) from a first position with the second ends of the pair of plates substantially together with one another, to (ii) a second position with the second ends of the pair of plates apart from one another so as to distract the tibia at the bone cut; and a multi-part implant for supporting the open wedge osteotomy in the tibia, the multi-part implant having a first component for disposition in a posterior portion of the open wedge osteotomy, a second component for disposition in an anterior portion of the open wedge osteotomy, and a connection device for selectively connecting the first component and the second component to one another;

aligning the positioning guide to the joint line of the tibia using the alignment component;

fixing the positioning guide to the tibia using the fixation component;

attaching the guide attachment component of the cutting guide to the positioning guide so as to position the angled cutting slot in a predetermined orientation with the joint line of the tibia;

moving the cutting blade through the angled cutting slot of the cutting guide so as to form the bone cut therein;

positioning the first end of the pair of plates of the mechanical jack into the bone cut, the pair of plates having their second ends in the first position with the second ends of the pair of plates substantially together;

actuating the mechanical jack to move the second ends of the pair of plates from the first position to the second position with the second ends of the pair of plates apart from one another so as to distract the tibia at the bone cut; and inserting the multi-part implant into the tibia.

In another form of the invention, there is provided a system for performing an opening wedge osteotomy in a tibia, the system comprising:

a cutting guide having a guide attachment component for selectively attaching the cutting guide to the tibia, the cutting guide forming an angled cutting slot therein configured to direct a cutting blade into the tibia so as to form a bone cut therein;

a mechanical jack having a pair of plates with a first end and a second end in opposition to one another, the first end of the pair of plates configured to remain substantially together with one another and configured for placement into the bone cut in the tibia, and the second end of the pair of plates configured for selective positioning (i) from a first position with the second ends of the pair of plates substantially together with one another, to (ii) a second position with the second ends of the pair of plates apart from one another so as to distract the tibia at the bone cut; and a multi-part implant for supporting the open wedge osteotomy in the tibia, the multi-part implant having a first component for disposition in a posterior portion of the open wedge osteotomy, a second component for disposition in an anterior portion of the open wedge osteotomy, and a connection device for selectively connecting the first component and the second component to one another.

In another form of the invention, there is provided a method for performing an opening wedge osteotomy in a tibia, the method comprising:

providing a system for performing an opening wedge osteotomy in a tibia, the system comprising:

a cutting guide having a guide attachment component for selectively attaching the cutting guide to the tibia, the cutting guide forming an angled cutting slot therein configured to direct a cutting blade into the tibia so as to form a bone cut therein;

a mechanical jack having a pair of plates with a first end and a second end in opposition to one another, the first end of the pair of plates configured to remain substantially together with one another and configured for placement into the bone cut in the tibia, and the second end of the pair of plates configured for selective positioning from (i) a first position with the second end of the pair of plates substantially together with one another, to (ii) a second position with the second end of the pair of plates apart from one another so as to distract the tibia at the bone cut; and a multi-part implant for supporting the open wedge osteotomy in the tibia, the multi-part implant having a first component for disposition in a posterior portion of the open wedge osteotomy, a second component for disposition in an anterior portion of the open wedge osteotomy, and a connection device for selectively connecting the first component and the second component to one another;

aligning the cutting guide to joint line of the tibia;

attaching the cutting guide to the tibia so as to position the angled cutting slot in a predetermined orientation with the joint line of the tibia;

positioning the cutting blade through the angled cutting slot of the cutting guide so as to form the bone cut therein;

positioning the first ends of the pair of plates of the mechanical jack into the bone cut, the pair of plates having their second ends in the first position with the second end of the pair of plates substantially together;

actuating the mechanical jack to move the second ends of the pair of plates from the first position to the second position with the second ends of the pair of plates apart from one another so as to distract the tibia at the bone cut; and inserting the multi-part implant into the tibia.

The above and other features of the invention, including various novel details of construction and combinations of parts and method steps, will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIGS. 48-89 are schematic views of alternative novel implants 500 which are illustrative of alternative embodiments for the novel multi-part implant shown in FIGS. 17-27;

FIGS. 90-110 are schematic views of a novel resection system 700, comprising a two blade positioning guide and a resection guide, which is illustrative of an alternative embodiment for the novel positioning guide shown in FIGS. 2-5 and for the novel cutting guide system shown in FIGS. 6-12; and FIGS. 111-130 are schematic views of a novel expandable wedge implant 805 which is illustrative of an alternative embodiment for the novel multi-part implant 125 shown in FIGS. 17-27.

DETAILED DESCRIPTION OF THE PREFERRED EMBODIMENTS

Overview

The present invention comprises surgical apparatus and methods for performing open wedge osteotomies. In one preferred embodiment of the present invention, the system embodies several novel devices and methods that provide for precise bone resection, precise control in opening an osteotomy void in the bone, precise achievement of the corrective angle for the open wedge osteotomy, and precise maintenance of the open wedge osteotomy that provides for the containment of bone graft or filler materials. The present invention provides an instrumentation-guided system with a minimally invasive approach for performing open wedge osteotomy procedures. In addition, the present invention provides an implant fixation system that promotes new bone growth and a strong bone repair.

Figure 1:
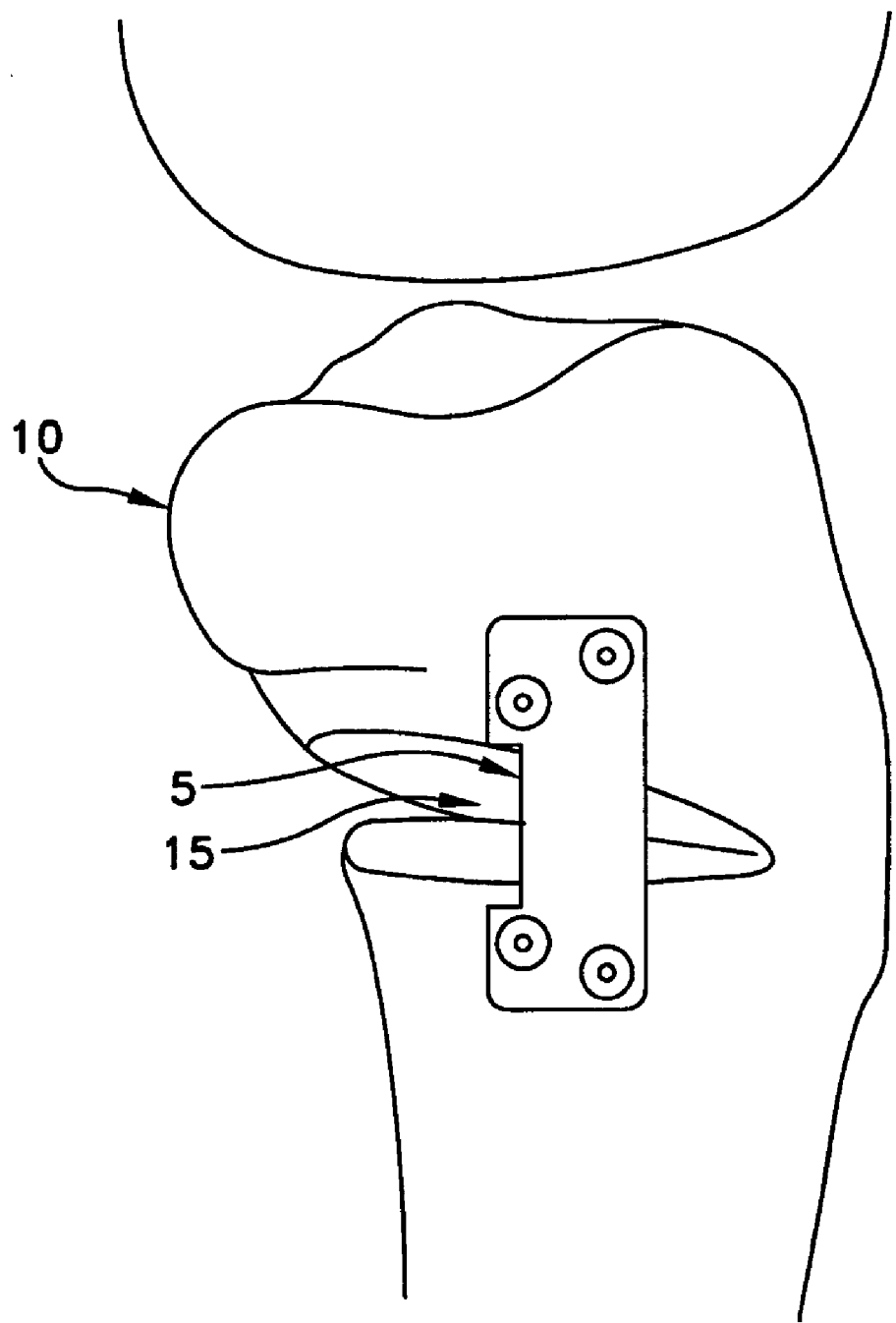
FIG. 1 is a schematic view of an osteotomy system using a prior art bone plate.
Figure 2:
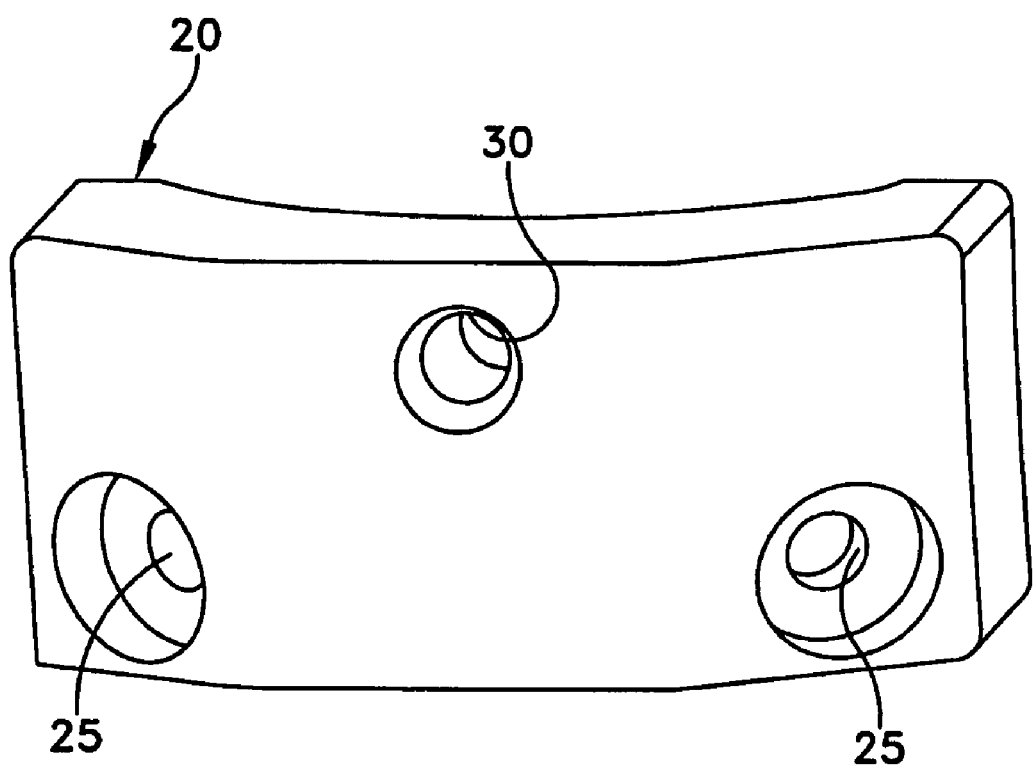
FIGS. 2-5 are schematic views of a novel positioning guide 20 which is illustrative of one component of a preferred embodiment of the novel osteotomy system.
Figure 15:
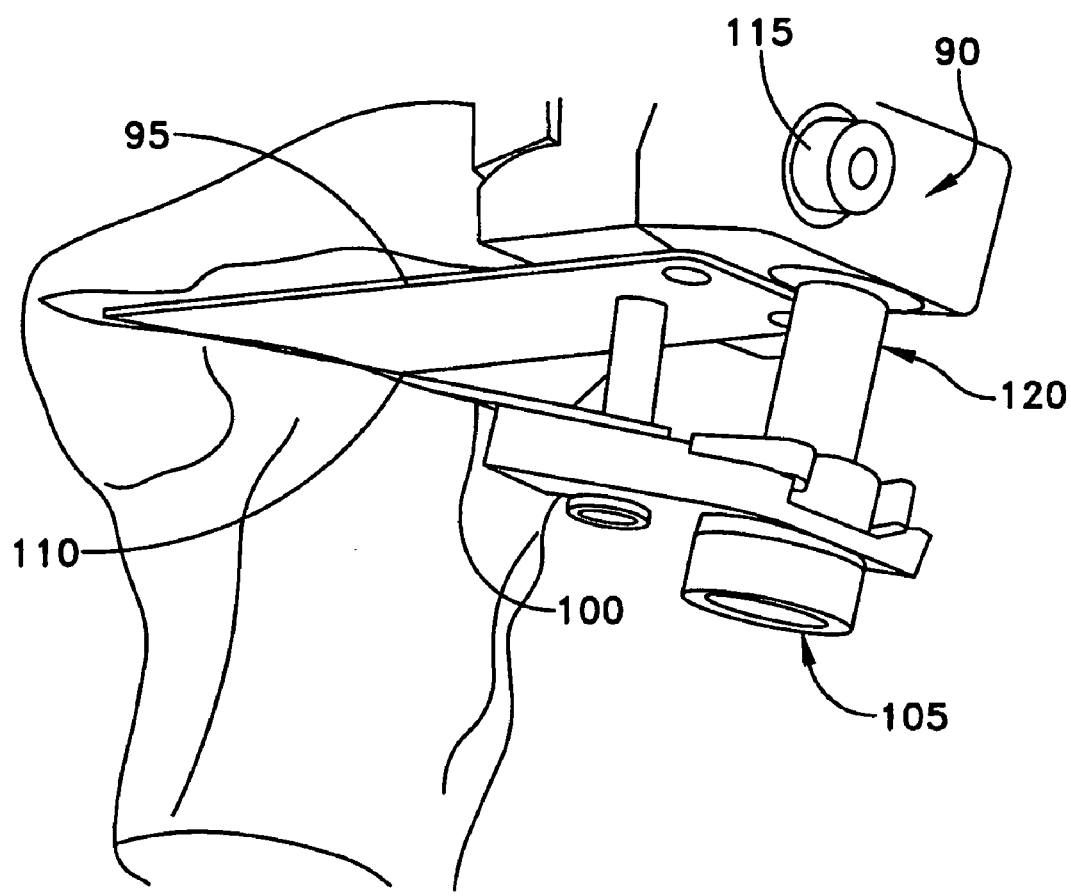
Figure 16:
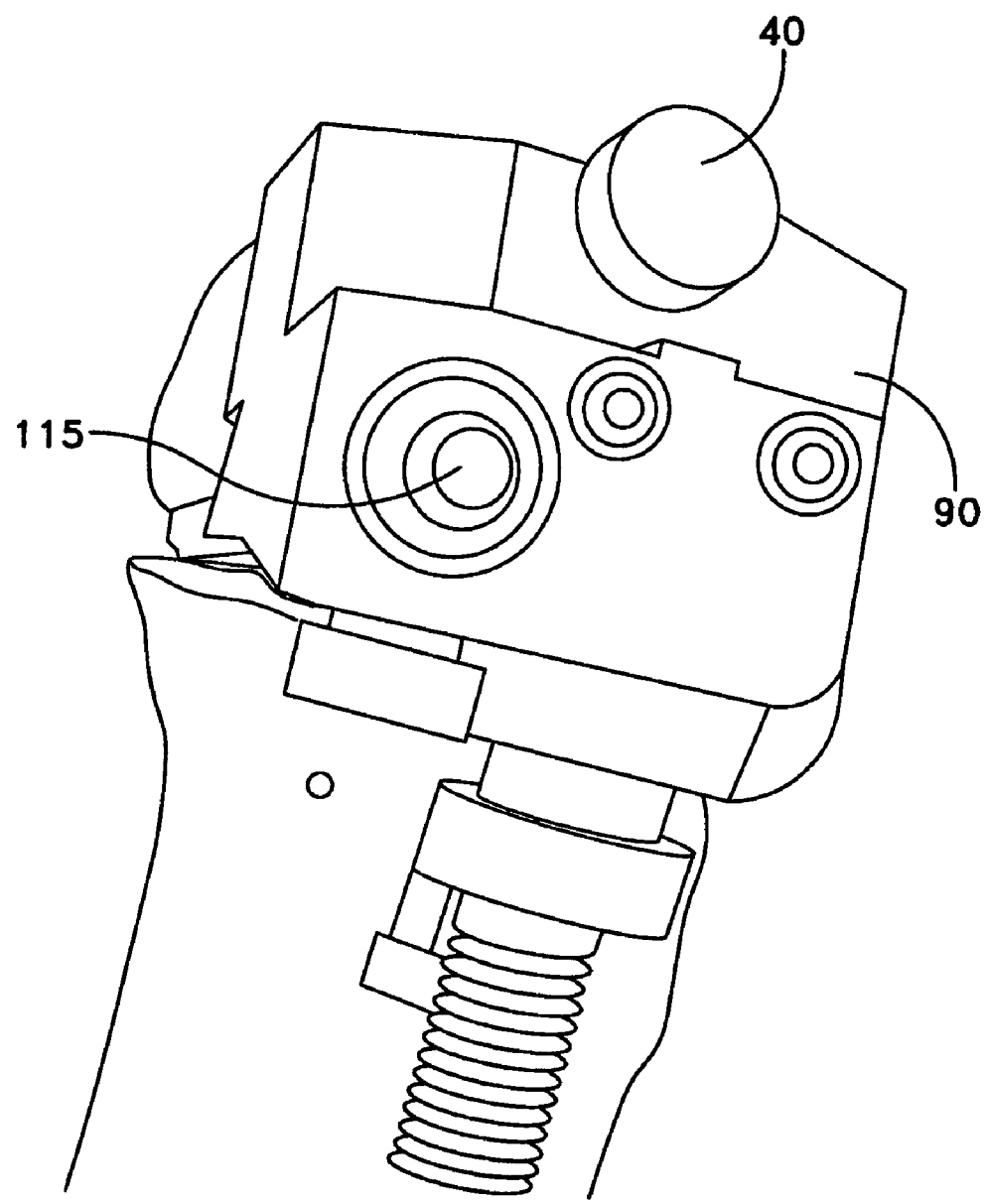
Figure 16A:
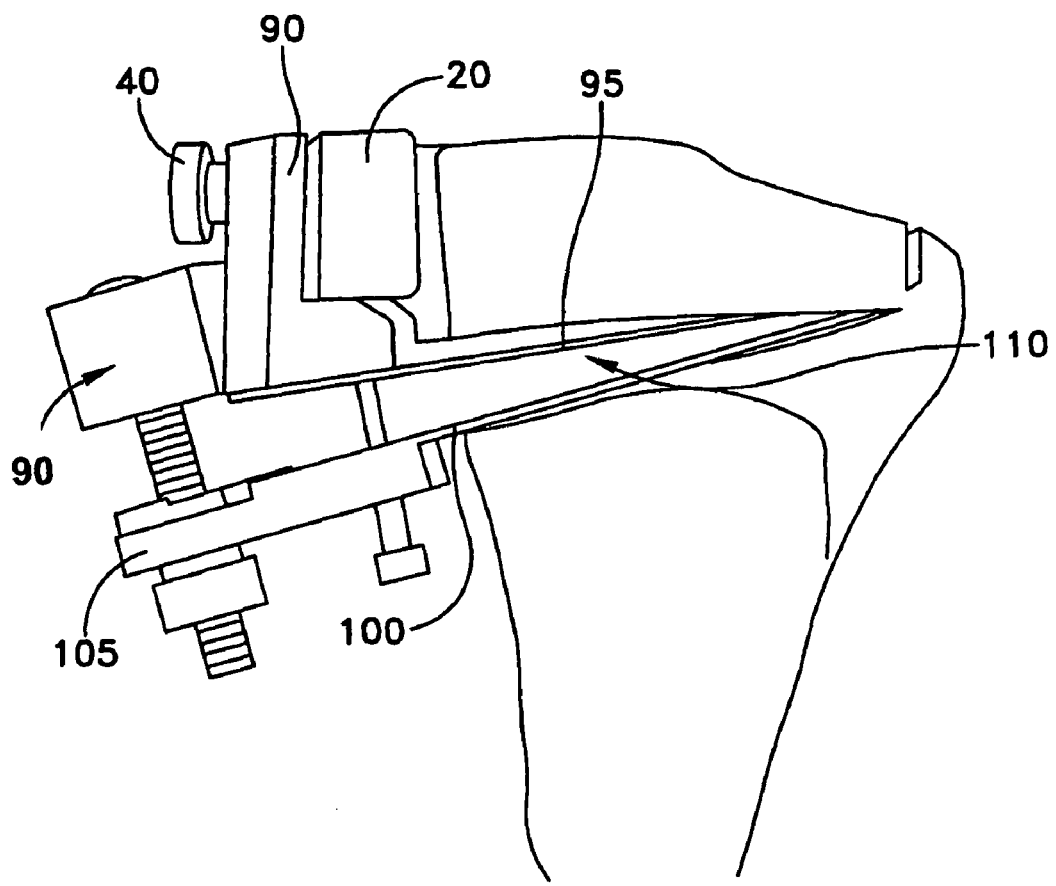
Figure 17:
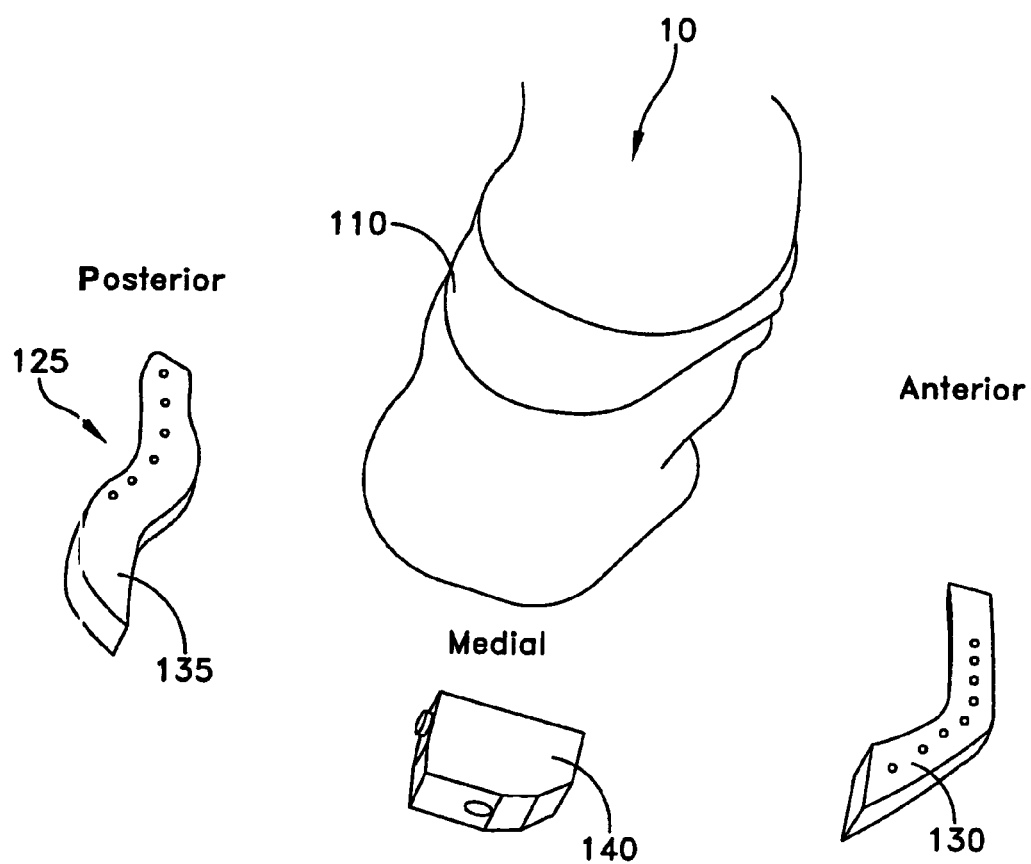
FIGS. 17-27 are schematic views of a novel multi-part implant 125 which is illustrative of one component of a preferred embodiment of the novel osteotomy system.
Figure 18:
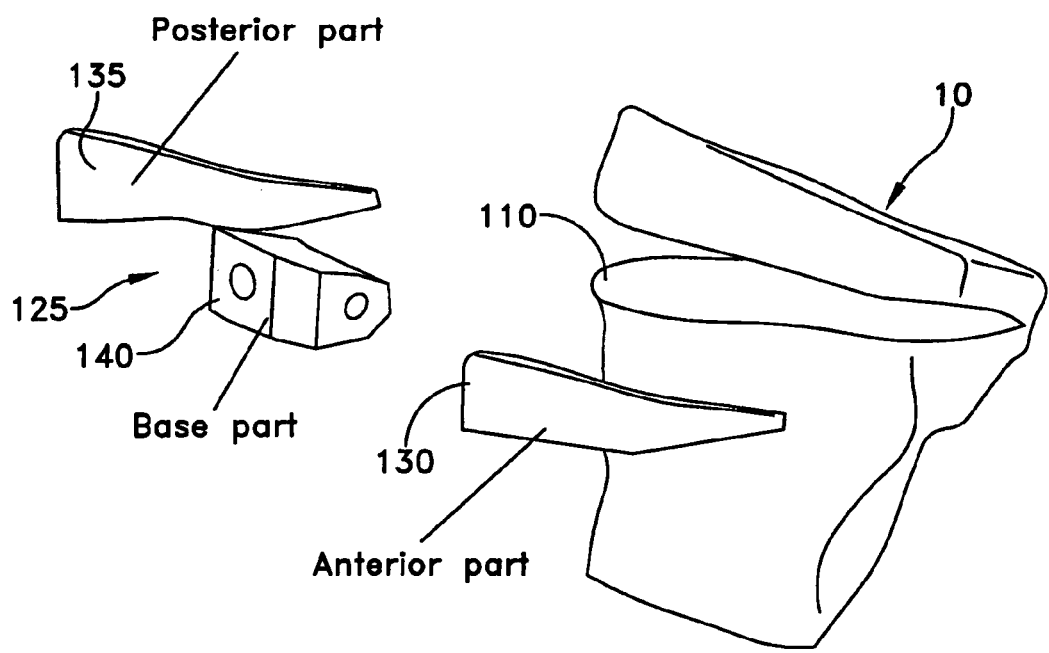
Figure 19:
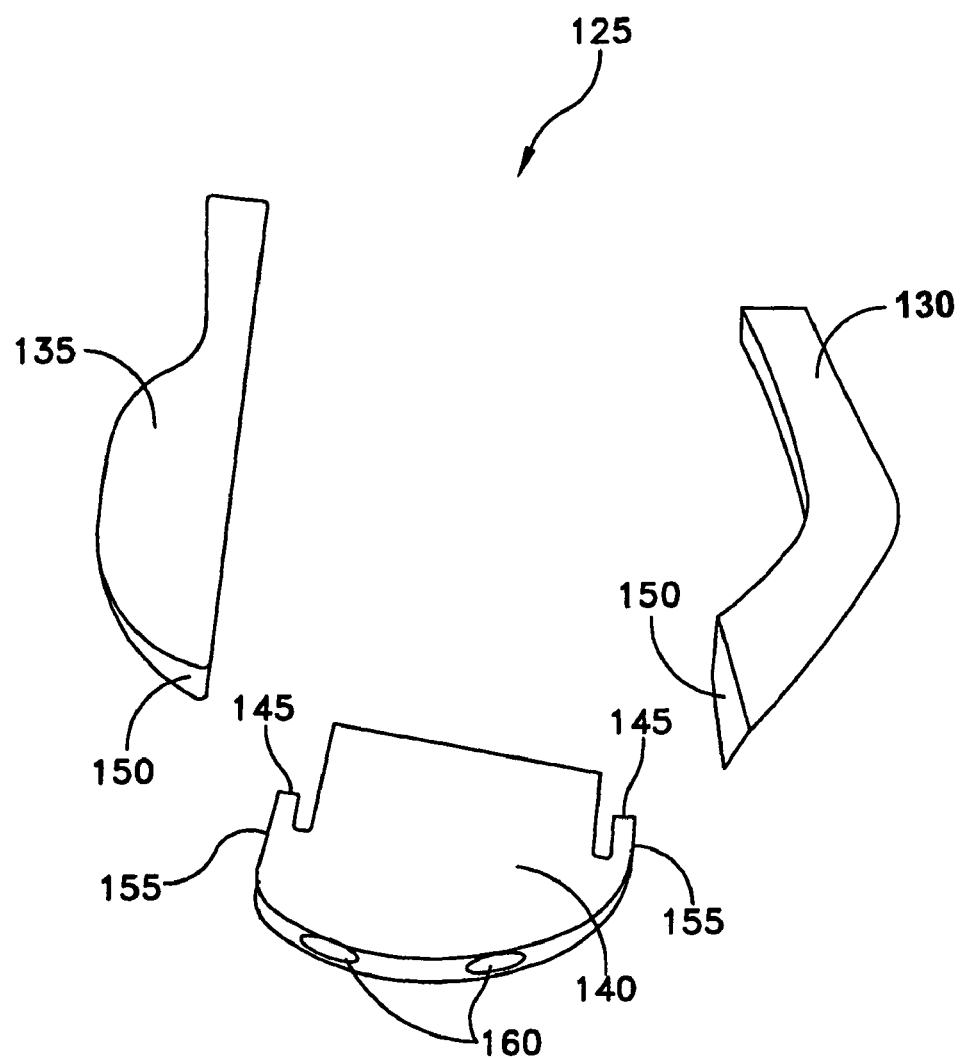
Figure 20:
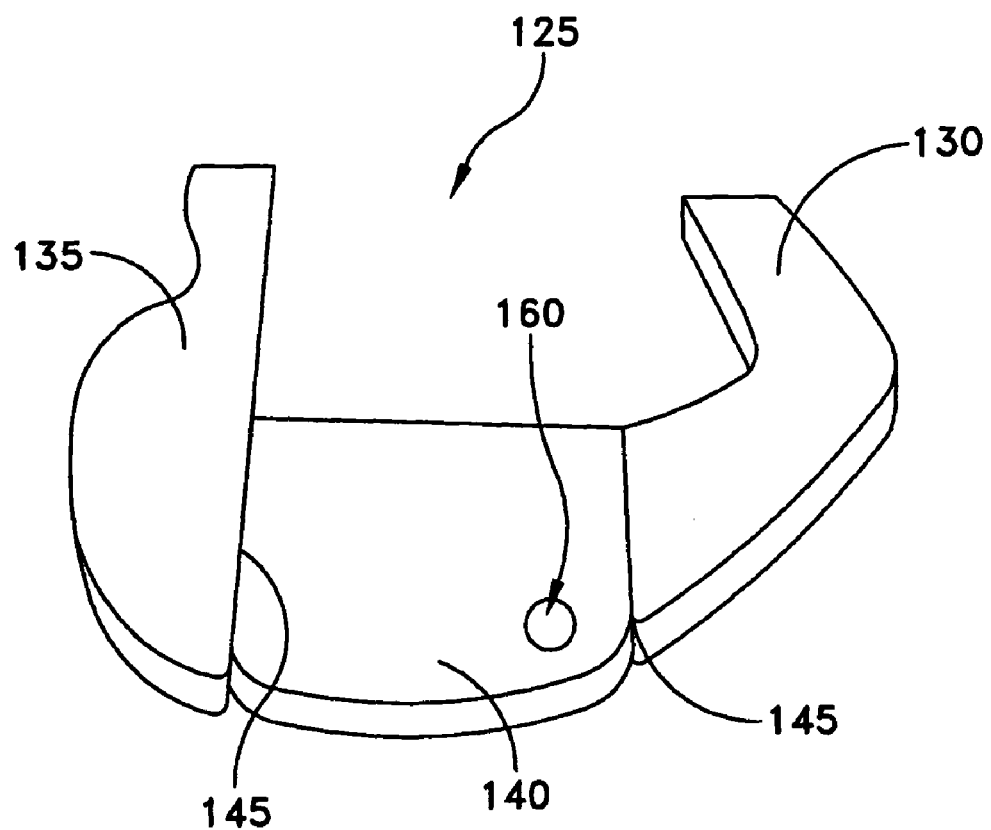
Figure 21:
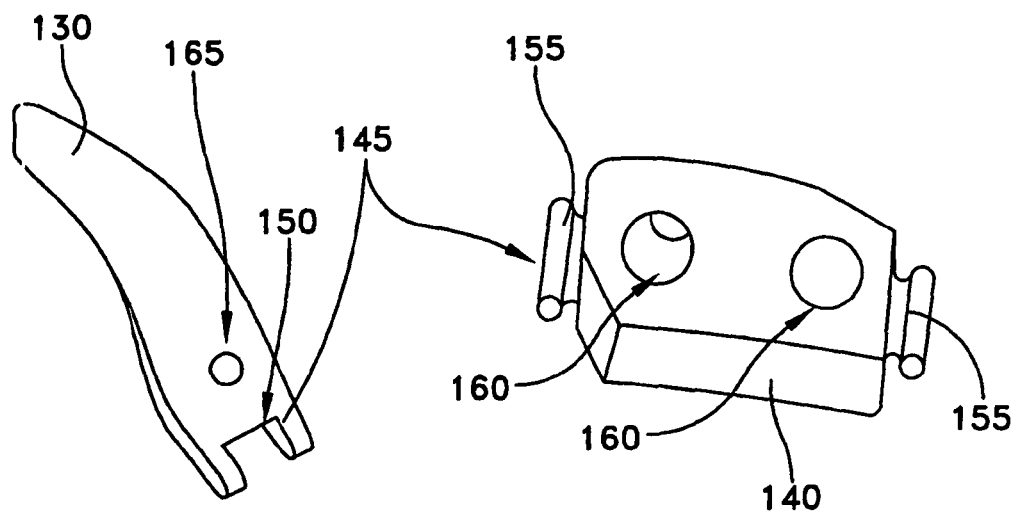
Figure 22:
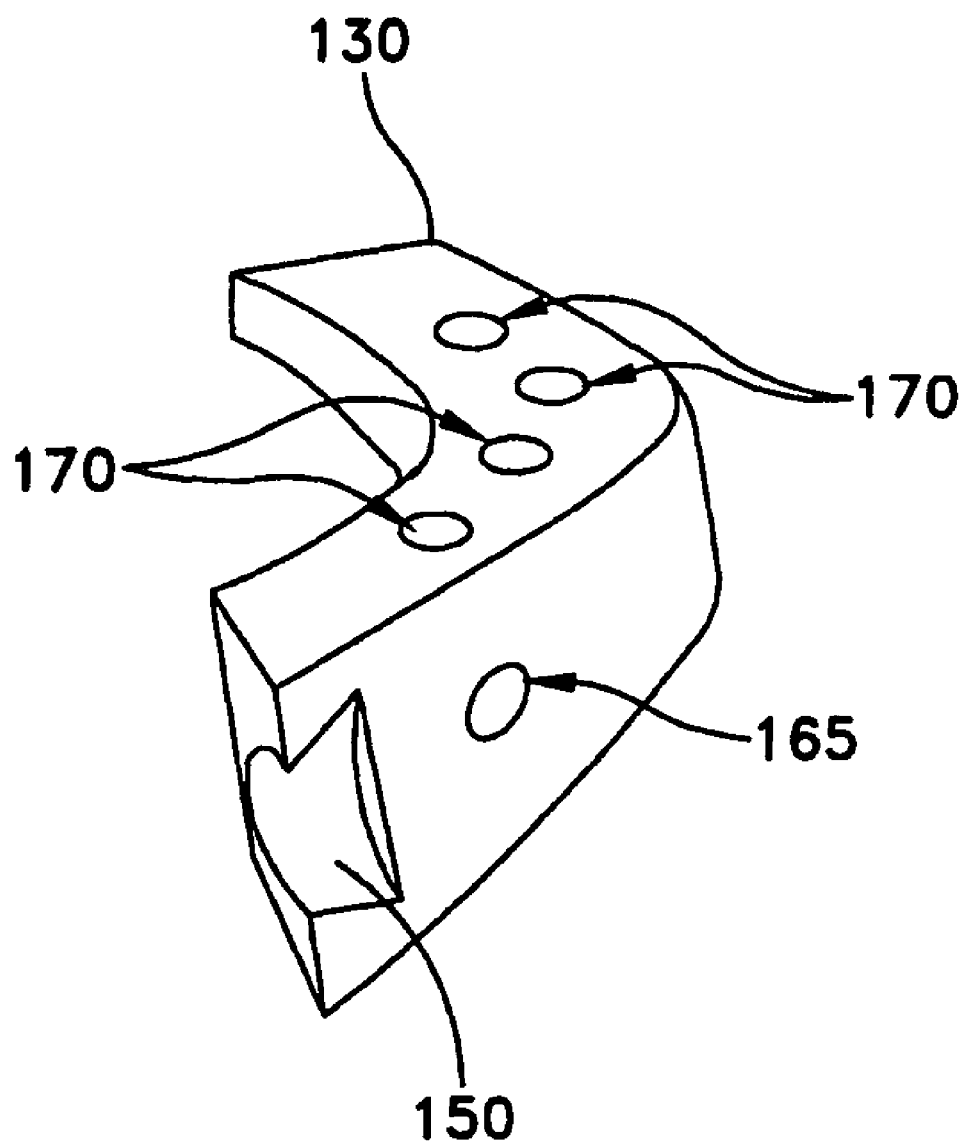
Figure 23:
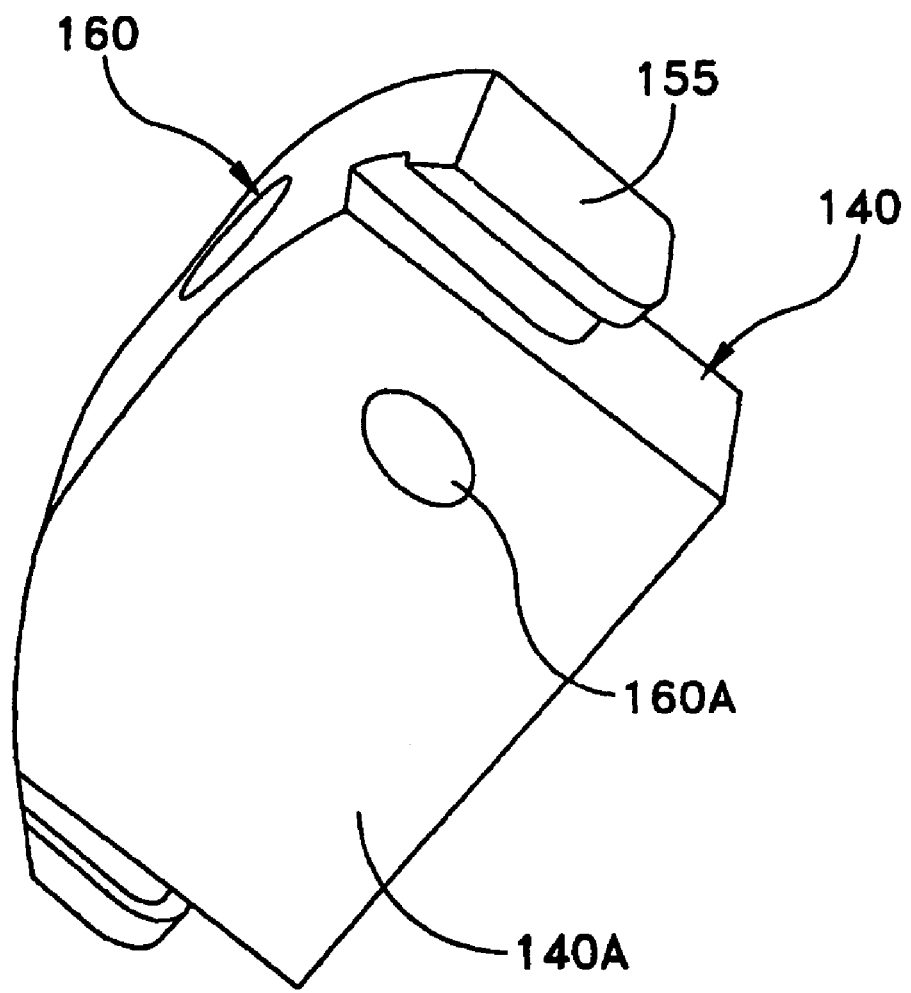
Figure 24:
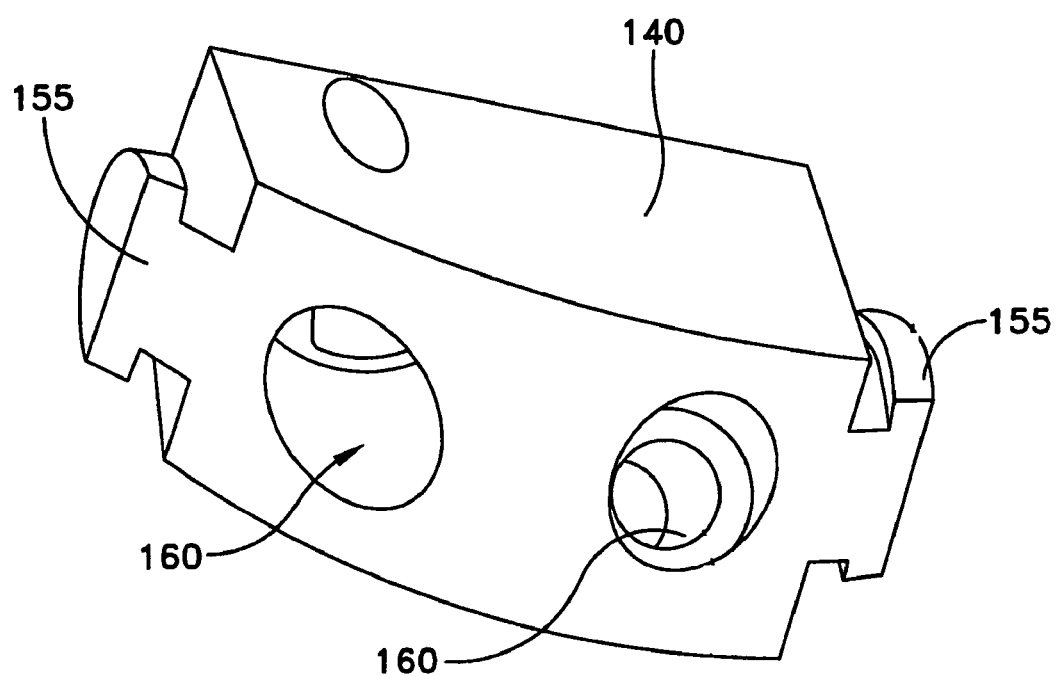
Figure 25:
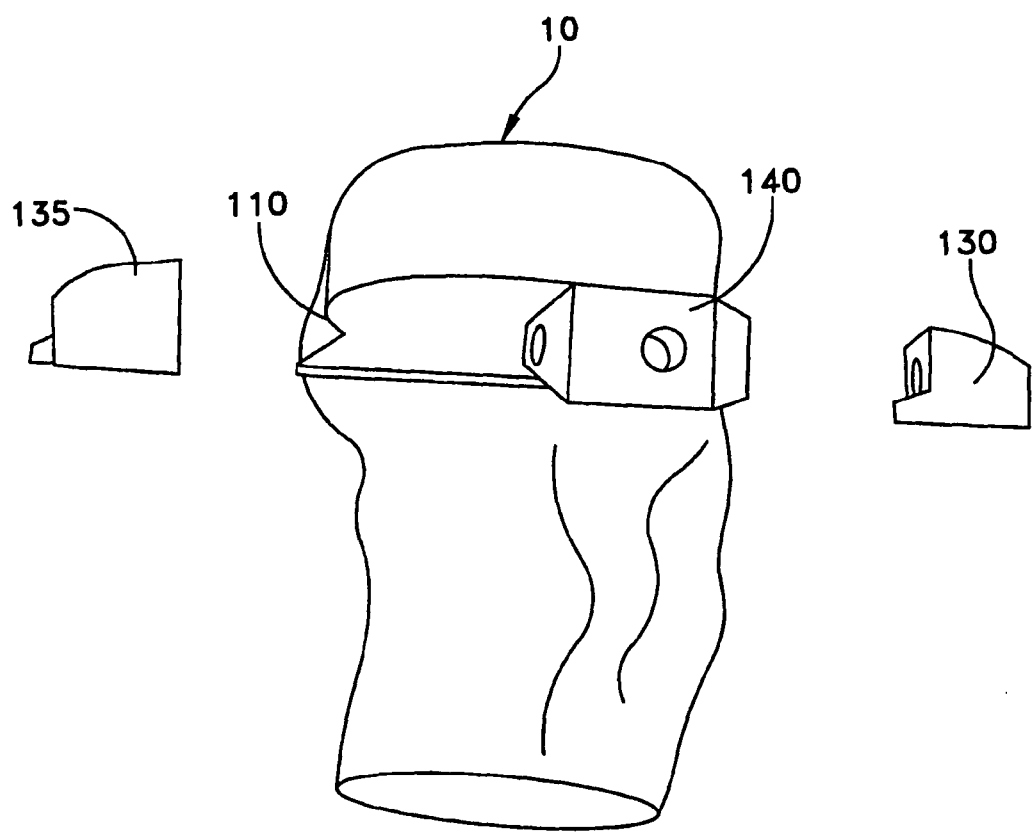

In one preferred form of the invention, the surgical system comprises four primary components: (i) a positioning guide 20 (FIG. 2) for establishing the orientation of the system relative to the patient's tibia; (ii) a cutting guide 45 (FIG. 7) for directing the osteotomy cut through the bone; (iii) a mechanical jack 90 (FIG. 15) for opening the osteotomy void in the bone; and (iv) a multi-part implant 125 (FIG. 20) for supporting the open wedge osteotomy during bone healing.

In accordance with the present invention, the surgeon first identifies the proper bone cut to be made in the tibia. Once surgeon has identified the proper attributes of the bone cut, the surgeon then uses the method and apparatus of the present invention to effect the bone resection.

More particularly, the surgeon preferably:

(i) attaches positioning guide 20 to the proper location on patient's tibia;

(ii) selects the proper cutting guide 45 to be attached to positioning guide 20, whereby to define the target slope (or plane) of the cut to be made in the tibia;

(iii) selects the proper protector members 70, 75 to be attached to the cutting guide 45, whereby to protect the soft tissue and neurovasculature structures surrounding the tibia;

(iv) secures the cutting guide 45 to positioning guide 20, and then secures protector members 70, 75 to the cutting guide 45;

(v) selects the proper cutting blade 65 to be used in the procedure, whereby to define the proper depth of the cut to be made in the tibia;

(vi) passes cutting blade 65 through guide slot 50 formed in cutting guide 45 and through tibia 10, following the pathway 65A established by cutting guide 45, until the cut has been made to the proper depth;

(vii) withdraws cutting blade 65;

(viii) uses mechanical jack 90 to open the cut in the bone to the proper angle; and (ix) inserts the multi-part implant 125 into the osteotomy void 110 created in the bone, whereby to hold the resected tibia in the proper configuration.

Preferably, bone cement or bone paste, etc. is inserted into interior of the osteotomy void, within multi-part implant 125, whereby to facilitate strong bone regrowth and/or bony ingrowth; and preferably bone cement is injected into the implant/bone interface to help further secure the multi-part implant to the bone.

Significantly, with the present invention, the bone cut is made easily and reliably using an antero-medial approach, while providing excellent protection of the soft tissue and neurovasculature structures surrounding the tibia. Furthermore, osteotomy stabilization is achieved through the use of an implant device that provides stability about the osteotomy site while allowing the direct contact of bone graft material with native bone within the open wedge osteotomy. Significantly, the present invention also allows for the necessary physiologic compression and stimulation required to promote new tissue and bone growth through the bony void. This is in sharp contrast with prior art open wedge osteotomy systems, which use fixation plates and screws to maintain and support the corrective wedge opening; such systems do not allow beneficial physiologic compressive forces to act on the bone/graft interfaces. This can lead to nonunion osteotomies and failed corrections.

Positioning Guide 20

Figure 3:
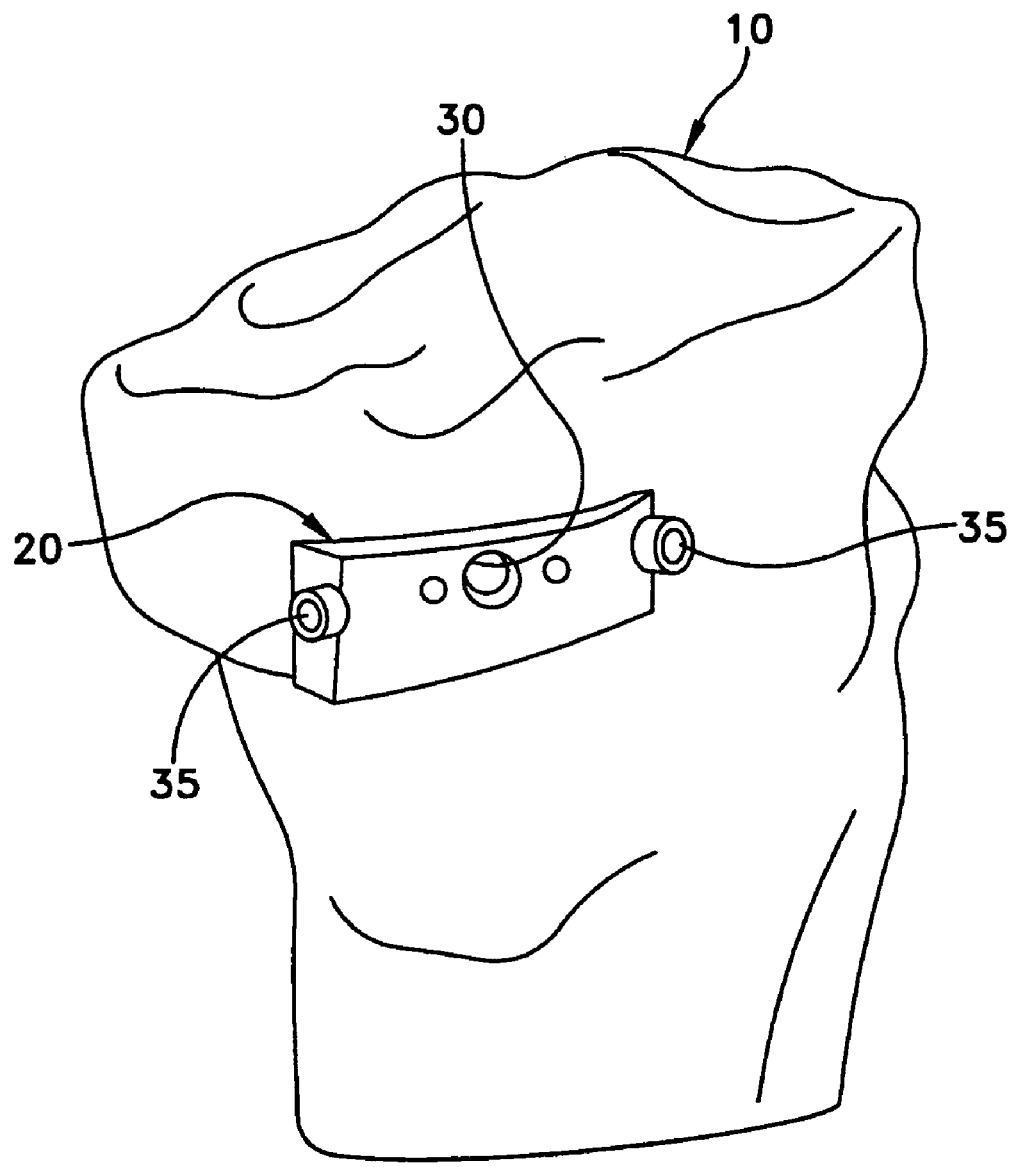
Figure 4:
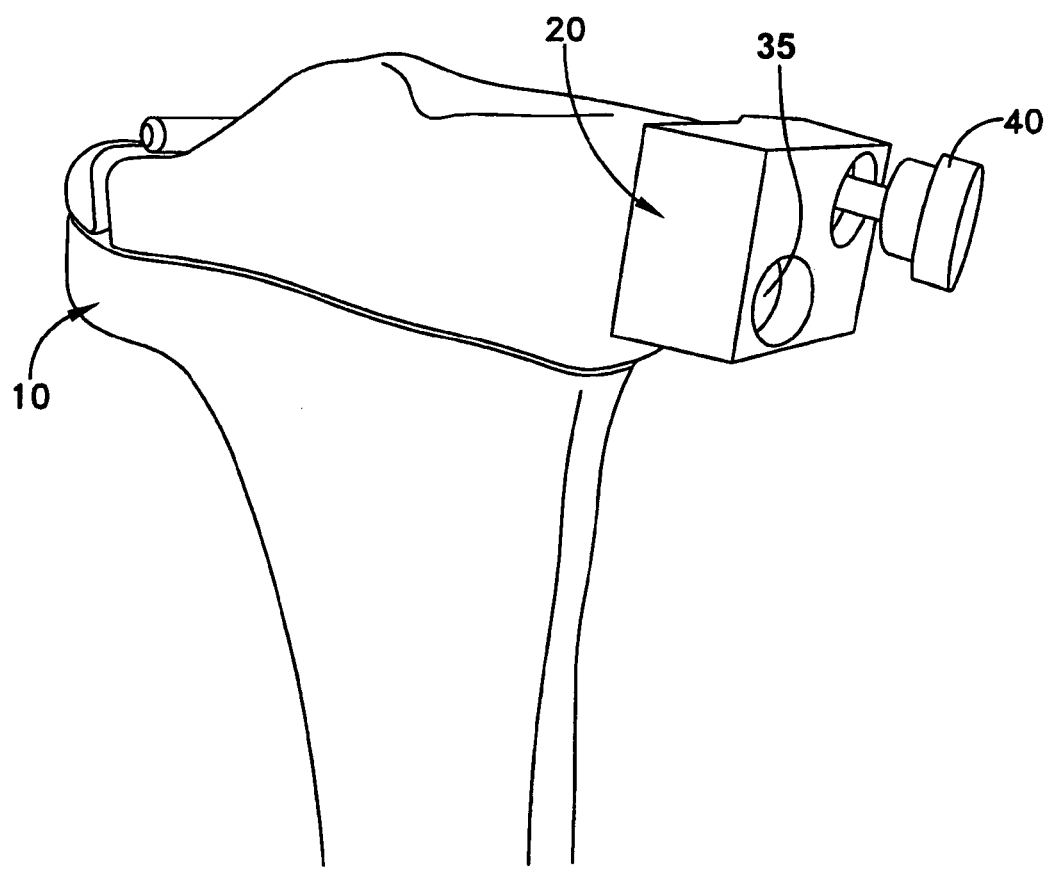

Looking next at FIGS. 2-5, in a preferred embodiment of the present invention, there is provided a positioning guide 20 which is configured to be aligned along the joint line of tibia 10 (FIG. 3) and fixed in place. In particular, the top of positioning guide 20 is aligned with the tibial plateau (i.e., the AP tibial slope), as shown in FIG. 4. Positioning guide 20 preferably includes a pair of fixation screw passageways 25 and a threaded attachment bore 30.

Figure 5:
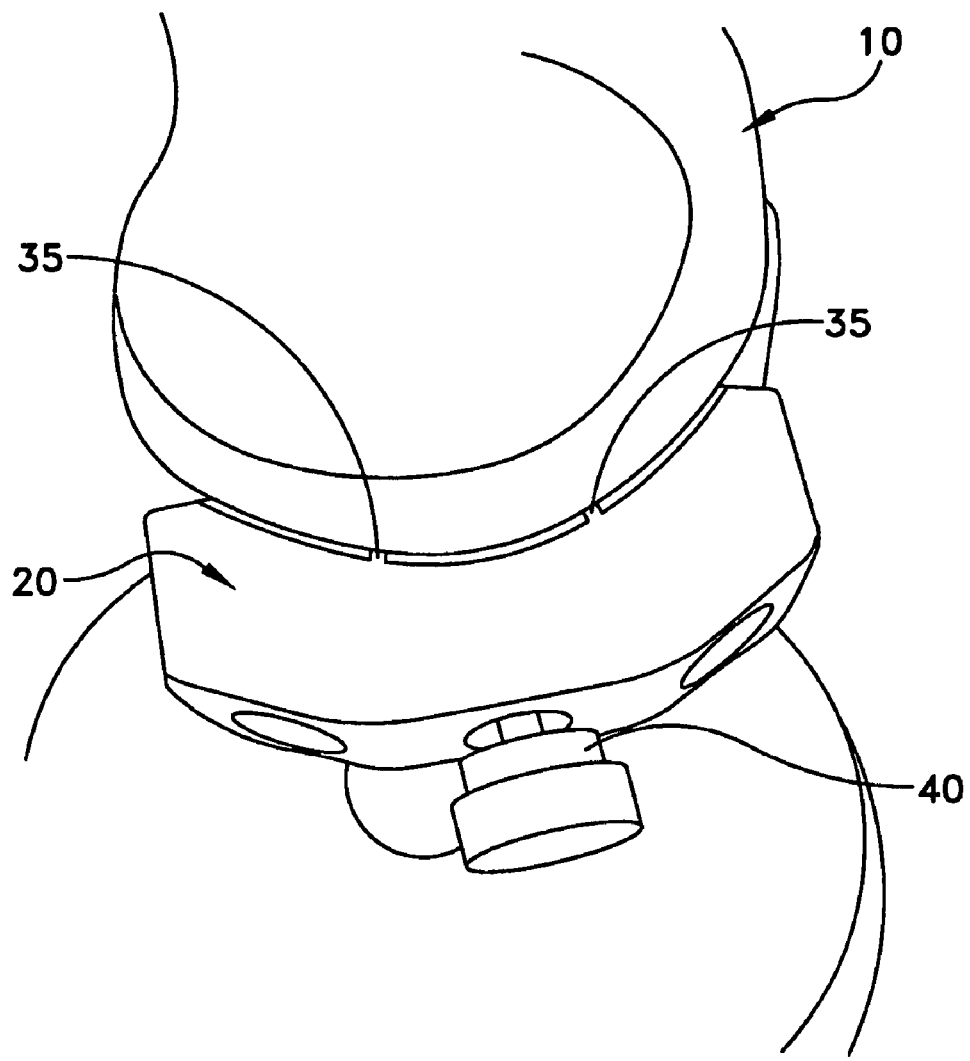
Figure 6:
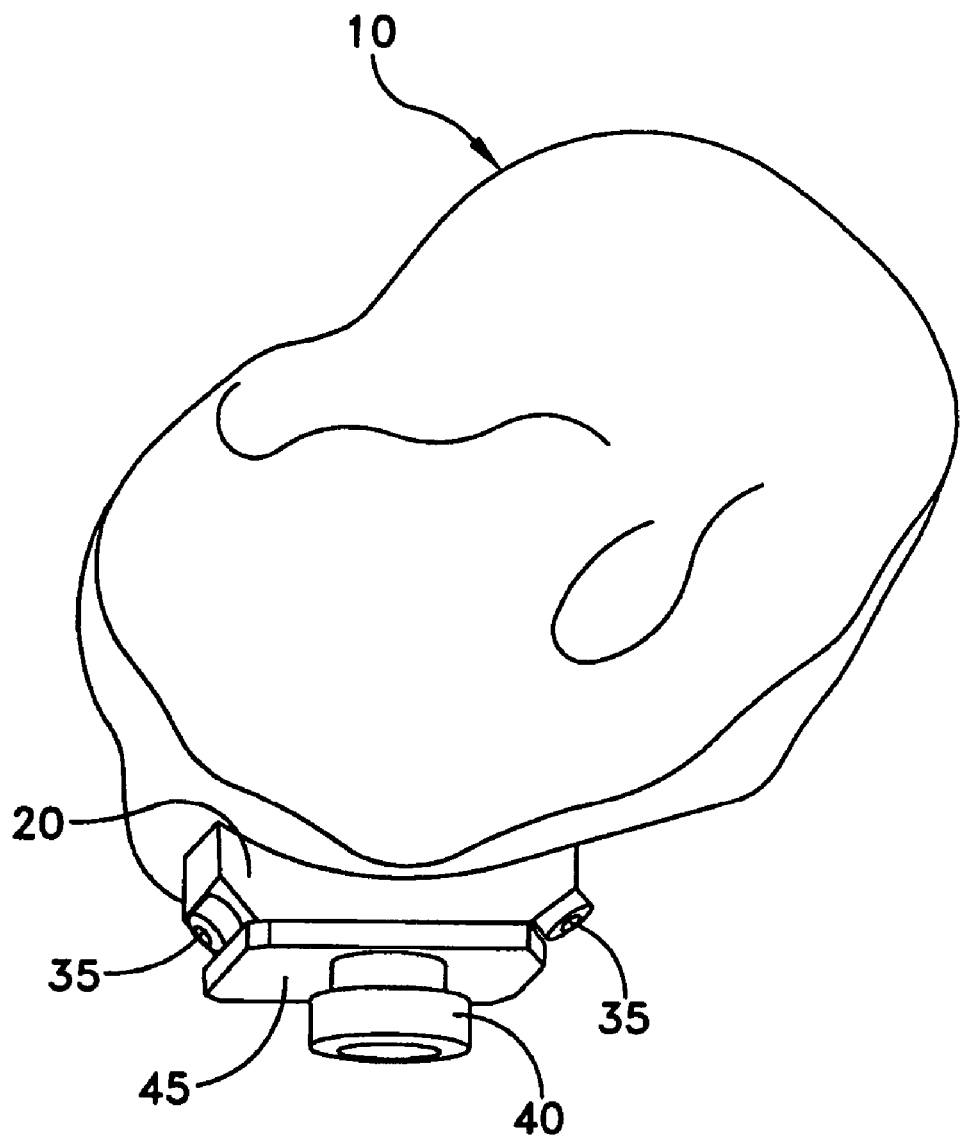
FIGS. 6-12 are schematic views of a novel cutting guide 45 which is illustrative of another component of a preferred embodiment of the novel osteotomy system.

Referring now to FIGS. 3-5, there is shown a pair of fixation screws 35 extending through positioning guide 20 and into tibia 10 so as to fix positioning guide 20 to tibia 10 after the top of positioning guide 20 is aligned with the top of tibia 10. An attachment screw 40 (FIGS. 4 and 5) is preferably provided for removable attachment of various devices to positioning guide 20. Attachment screw 40 preferably includes a threaded shaft configured for engagement with threaded attachment bore 30.

Cutting Guide 45

Figure 7:
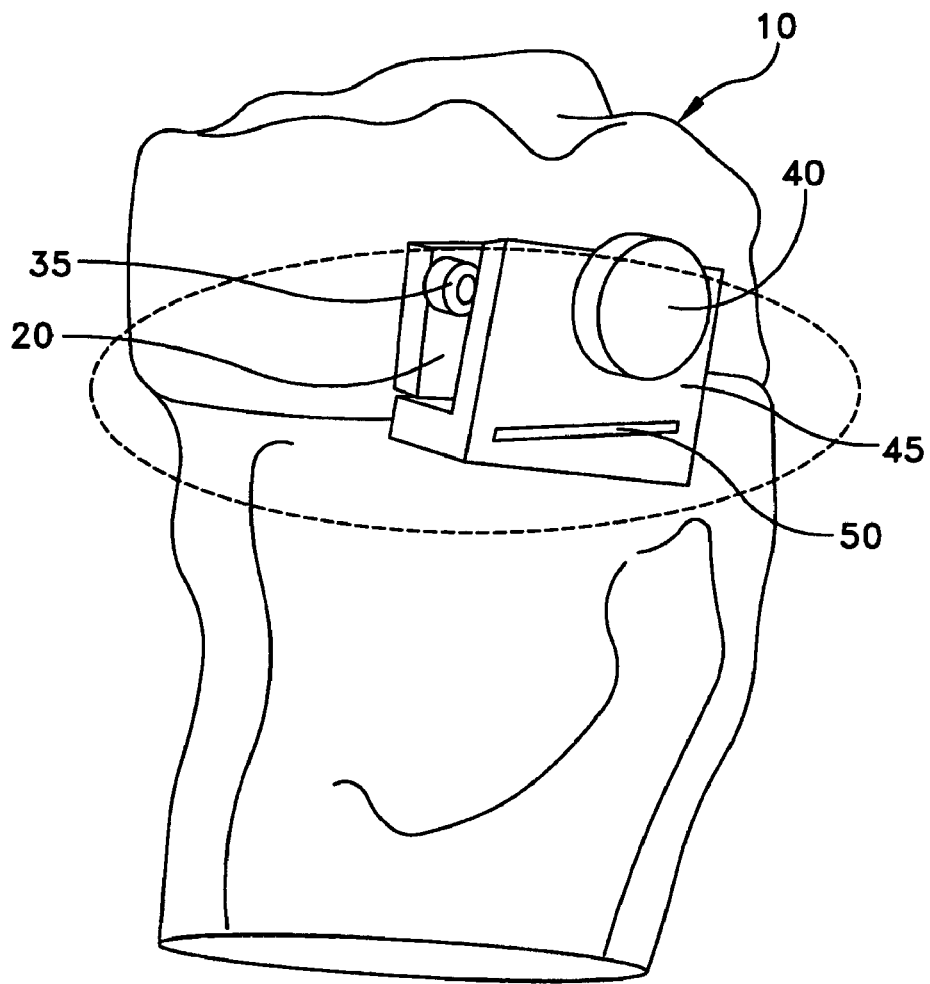

Looking next at FIGS. 6-12, there is shown a cutting guide 45 configured for attachment to positioning guide 20. Cutting guide 45 is preferably secured to positioning guide 20 with attachment screw 40. As seen in FIG. 7, a cutting guide slot 50 provides a fixed angle by which a controlled bone resection can be performed.

Figure 8:
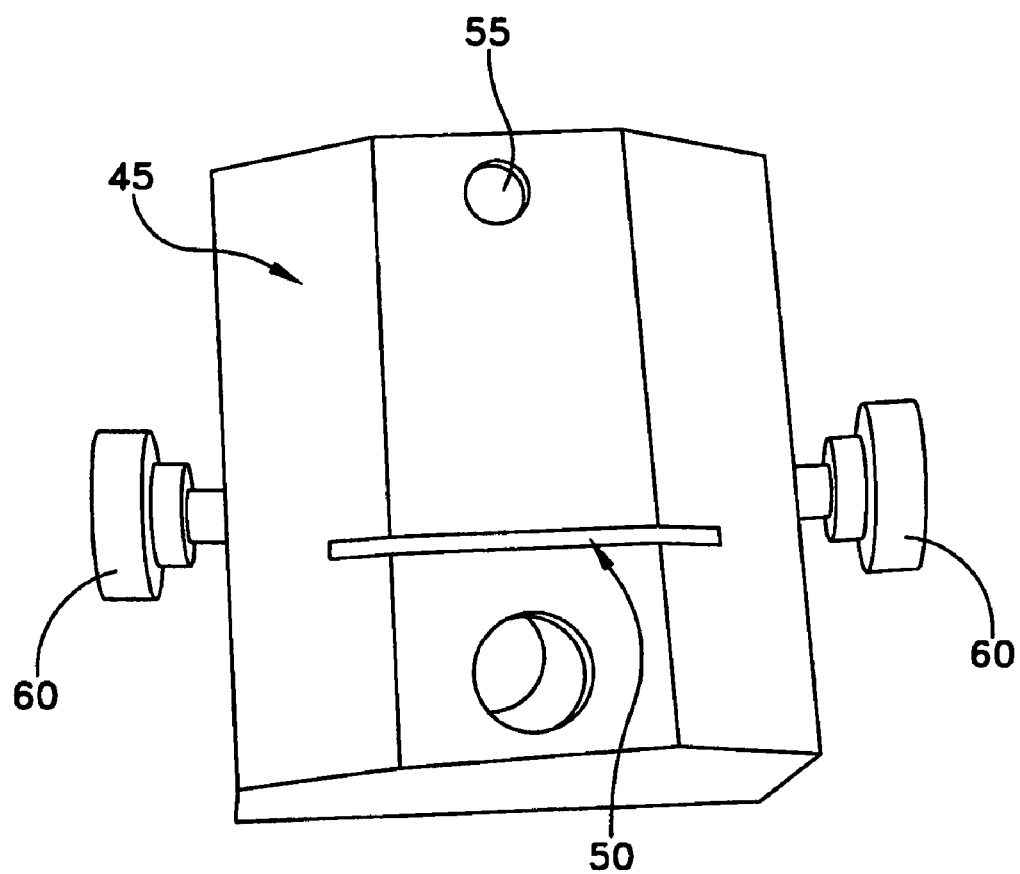
Figure 9:
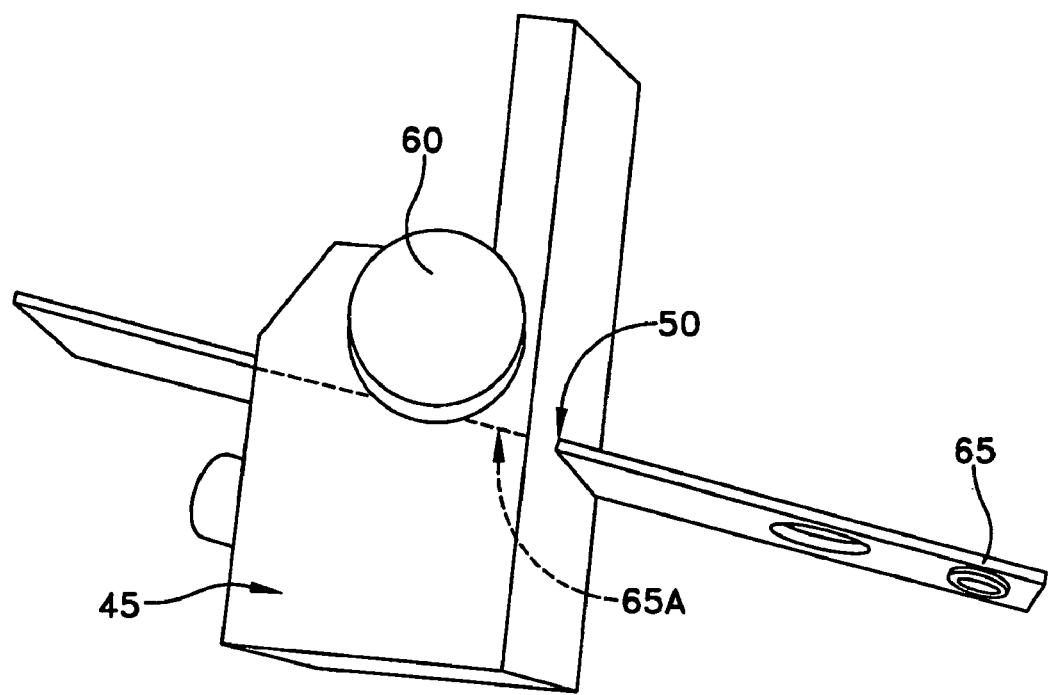

More particularly, and referring now to FIGS. 8 and 9, cutting guide 45 comprises a throughbore 55 (FIG. 8) which receives the attachment screw 40 (FIG. 7) so as to mount cutting guide 45 to positioning guide 20, whereby to position the angled cutting slot 50 relative positioning guide 20 (and hence relative to the AP tibial slope). Preferably, mounting clamps 60 (FIG. 8) are provided at the side portions of cutting guide 45 for mounting protector members 70, 75 (see below) to cutting guide 45. A cutting blade 65 (FIG. 9) is selectively inserted through guide slot 50 so that the cutting blade 65 can cut along pathway 65A at a predetermined angle relative to cutting guide 45 (and hence, relative to the AP tibial slope).

Figure 10:
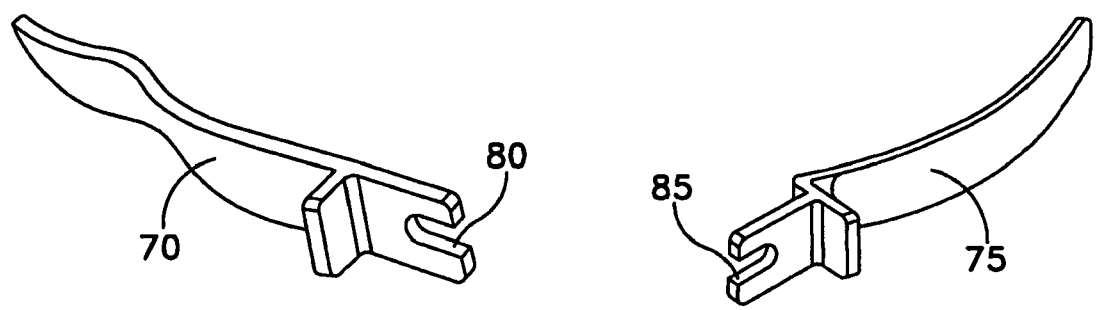
Figure 11:
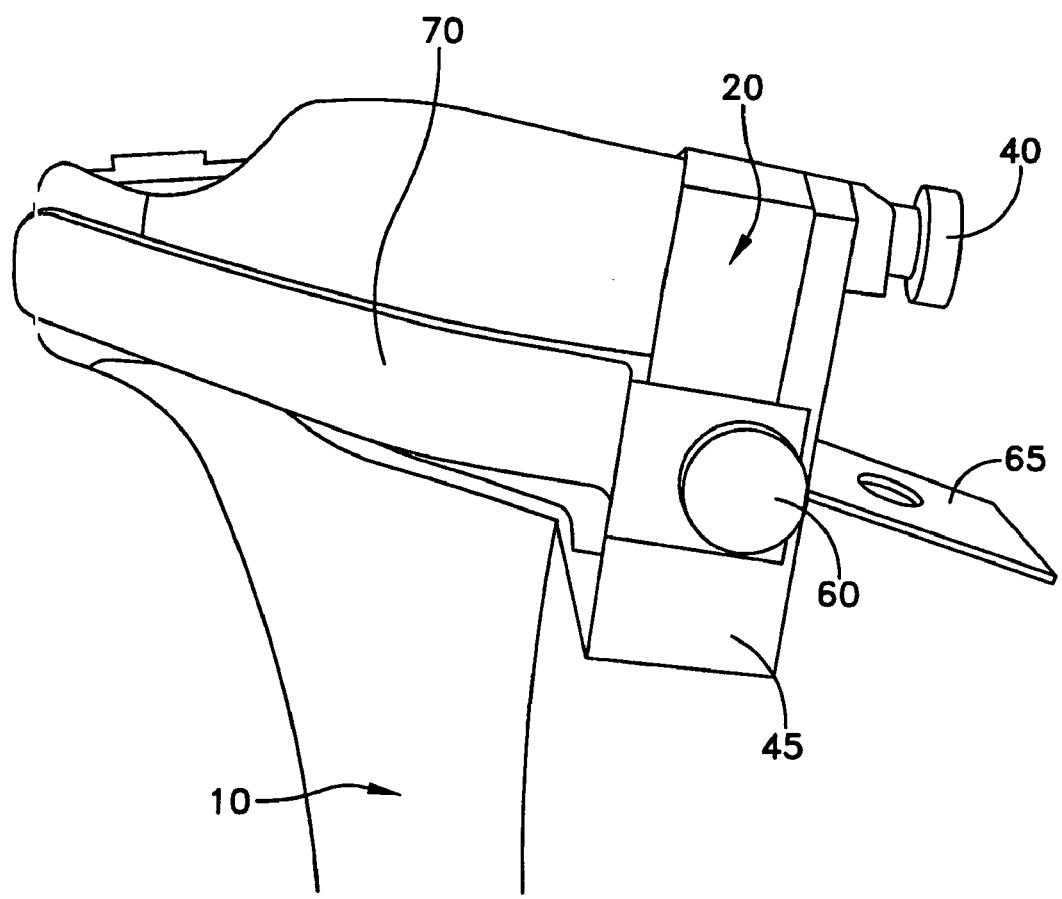
Figure 12:
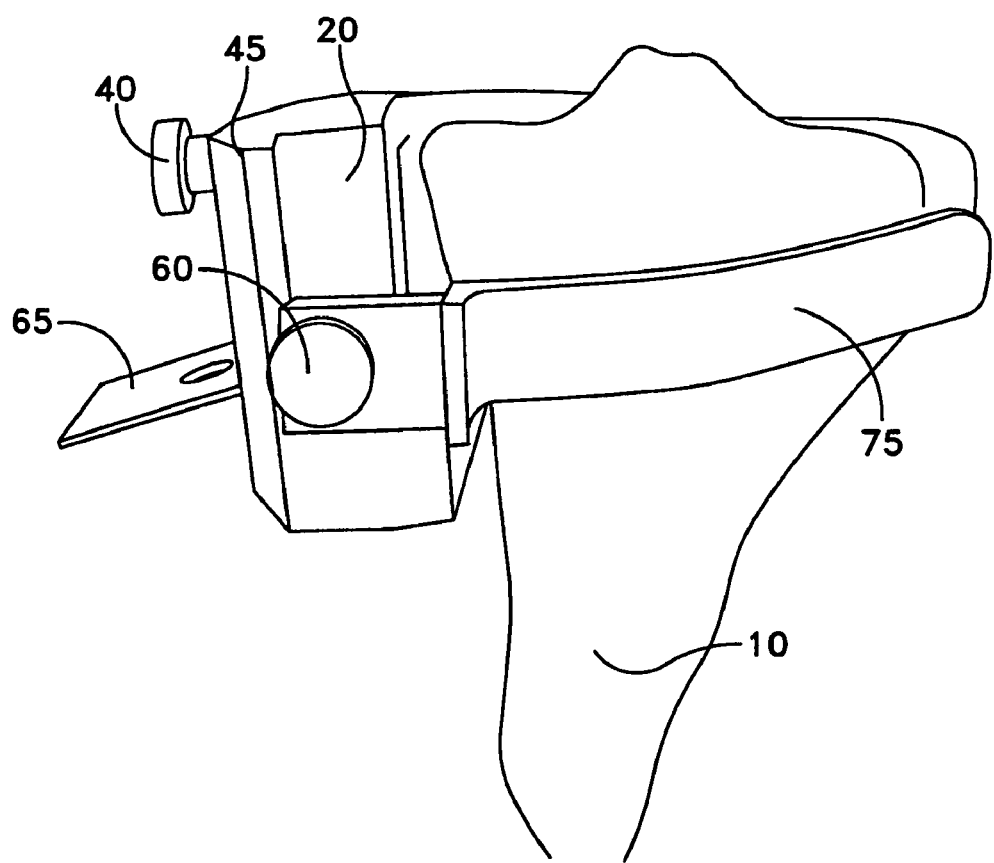
Figure 13:
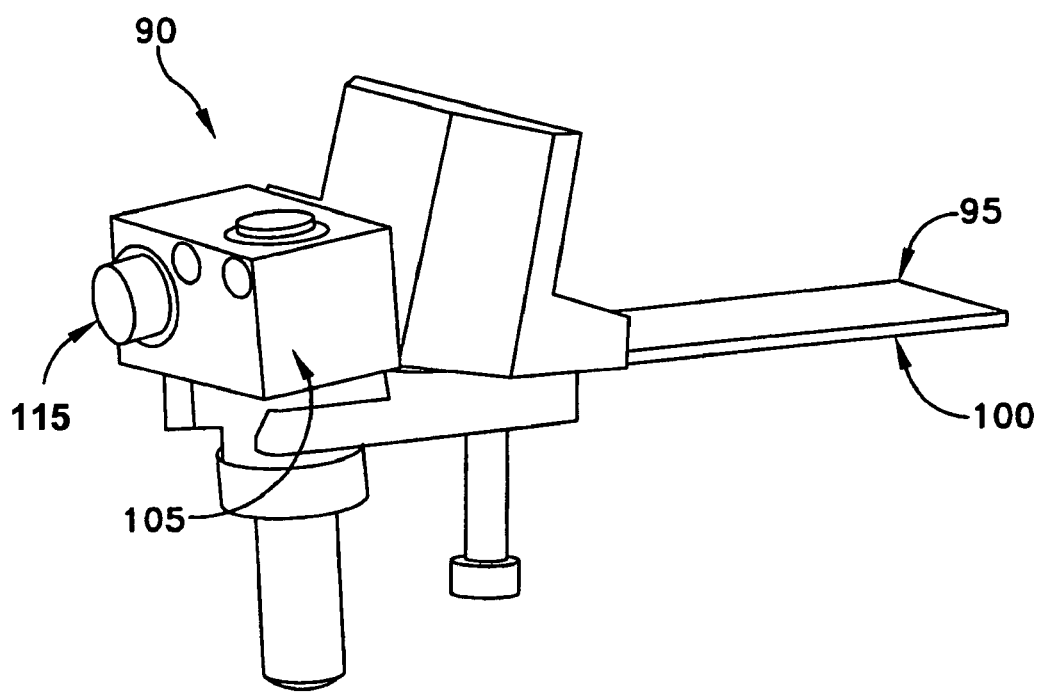
FIGS. 13-16 and 16A, are schematic views of a novel mechanical jack 90 which is illustrative of another component of a preferred embodiment of the novel osteotomy system.

Referring to FIG. 10-12, cutting guide 45 preferably comprises protector members 70, 75 to protect soft tissue and neurovascular structures during bone cutting. Protector members 70, 75 are (i) inserted into the patient through small medial surface incisions; (ii) passed beneath the skin tissue, close to the front and back surfaces of tibia 10; and (iii) secured to cutting guide 45 using mounting clamps 60 (see FIGS. 11 and 12). Protector member 70 is specifically contoured for the anterior aspect of tibia 10 (FIG. 11) and protector member 75 is specifically contoured for the posterior aspect of tibia 10 (FIG. 12). Each protector member 70, 75 can be radiolucent, with a radiographic marker running the length of its mid-section to show the direction of the bone cut, for example, under fluoroscopy, prior to beginning the bone resecting phase.

FIGS. 11 and 12 show cutting blade 65 passing through cutting slot 50 (FIG. 9) in cutting guide 45 and into tibia 10. As cutting blade 65 passes through cutting slot 50 and cuts the bone along the desired angle, protector members 70, 75 ensure that cutting blade 65 does not inadvertently cut soft tissue and neurovascular structures anterior and posterior to the bone.

Mechanical Jack 90

Referring next to FIGS. 13-16 and 16A, once the bone cut is made, cutting guide 45 and protector members 70, 75 can be removed. A mechanical jack device 90 (FIG. 13) is then secured to positioning guide 20. More particularly, two metal plates 95, 100 (of mechanical jack 90) are inserted into the bone cut in tibia 10, and mechanical jack 90 is then secured to positioning guide 20. Mechanical jack 90 may then be used to open metal plates 95, 100 relative to one another so as to create the desired osteotomy void in tibia 10.

Figure 14:
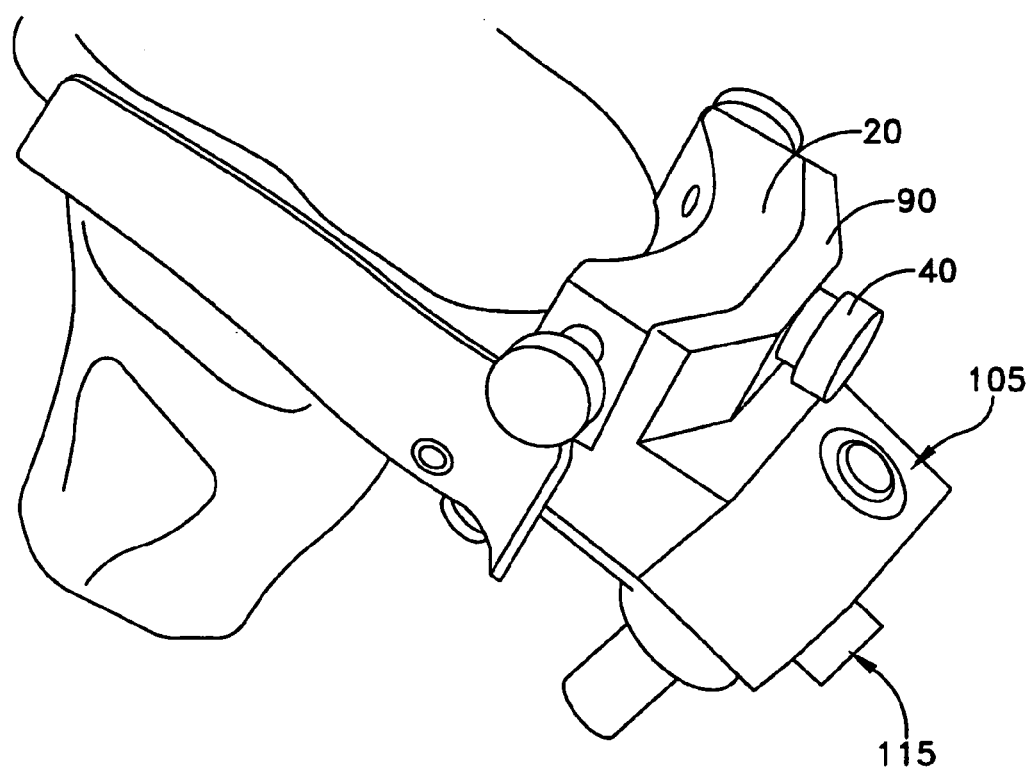

Alternatively, and looking now at FIG. 14, protector members 70, 75 may be left in place within the incision while mechanical jack 90 is secured to positioning guide 20 and operated to open the bone cut in tibia 10.

Mechanical jack 90 is opened by turning a worm gear end 115 with a screwdriver or other instrument (not shown). See FIGS. 15, 16 and 16A. Calibrations (not shown) preferably disposed on strut 120 (FIG. 15) indicate the opening or angle (or height) of void 110.

Once the osteotomy wedge has been opened to a desired position, either (i) the entire mechanical jack 90 is removed, or (ii) just the front portion 105 of the mechanical jack 90 is removed, leaving blades 95, 100 within the bone so as to hold open the osteotomy void 110 in tibia 10.

Multi-Part Implant 125

Once mechanical jack 90 has been used to open the osteotomy void 110 in tibia 10, a multi-part implant 125 is deployed in the void so as to support the bone in the desired position during healing.

More particularly, and looking now at FIGS. 17-27, there is shown a multi-part implant 125 which may be used to hold open the osteotomy void 110. Preferably, multi-part implant 125 comprises an anterior part 130, a posterior part 135, and a medial or base part 140 (see FIGS. 17-20). Anterior part 130, posterior part 135 and base part 140 are preferably assembled together in-situ to form the complete multi-part implant 125. More particularly, slotted fittings 145 (formed by a first portion 150 on each of anterior part 130 and posterior part 135, and a second portion 155 on each end of base part 50) serve to connect anterior part 130 and posterior part 135 to base part 140. While fittings 145 are shown in the drawings to comprise a male member on base part 140 and female member on anterior part 130 and posterior part 135, this arrangement could be reversed, or alternative fittings or connectors may be used. Implant 125 is preferably deployed in osteotomy void 110 by (i) first separately positioning anterior part 130, posterior part 135, and base part 140 in the void, and (ii) then joining anterior part 130, posterior part 135, and base part 140 together (using slotted fittings 145).

Figure 26:
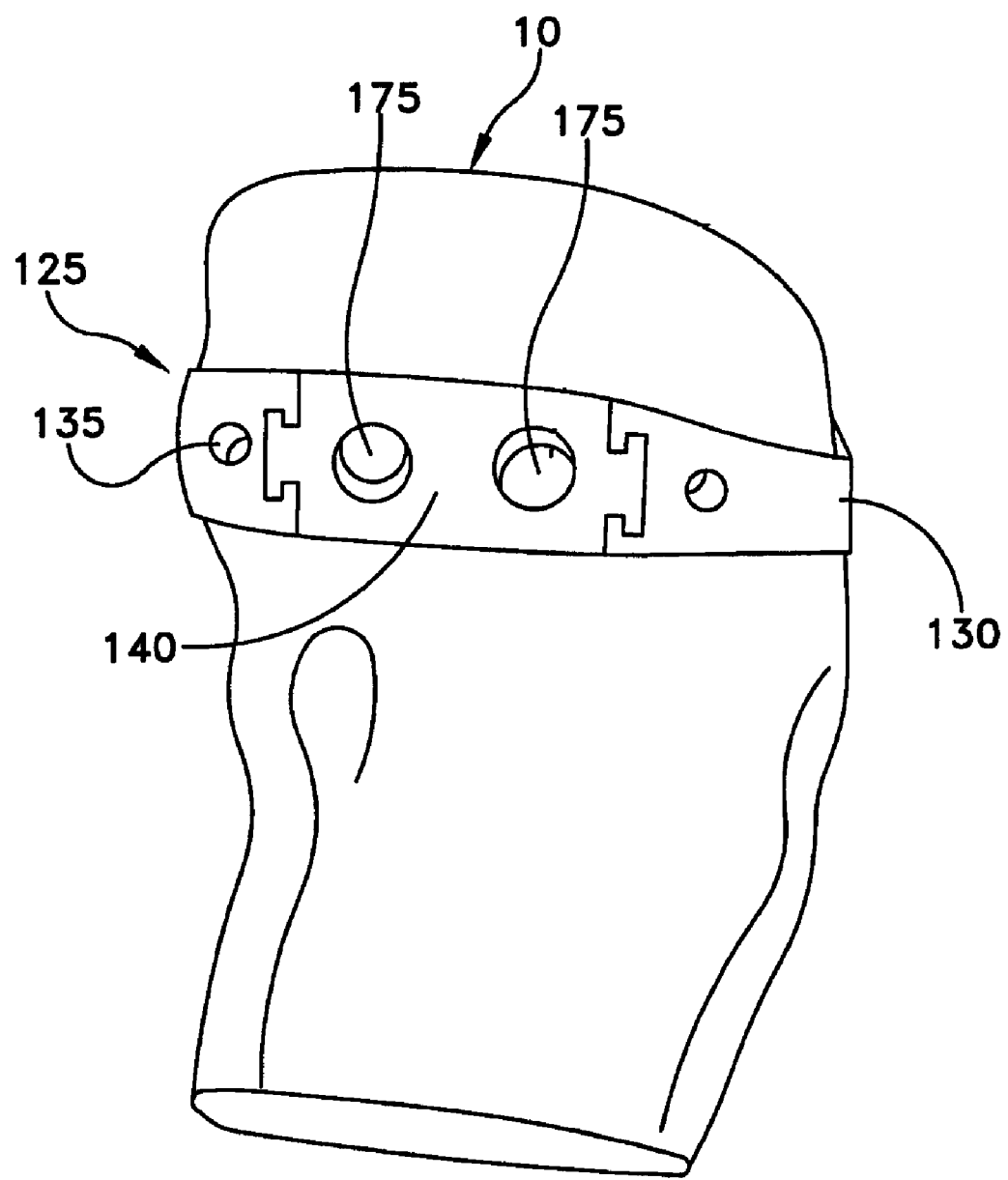
Figure 27:
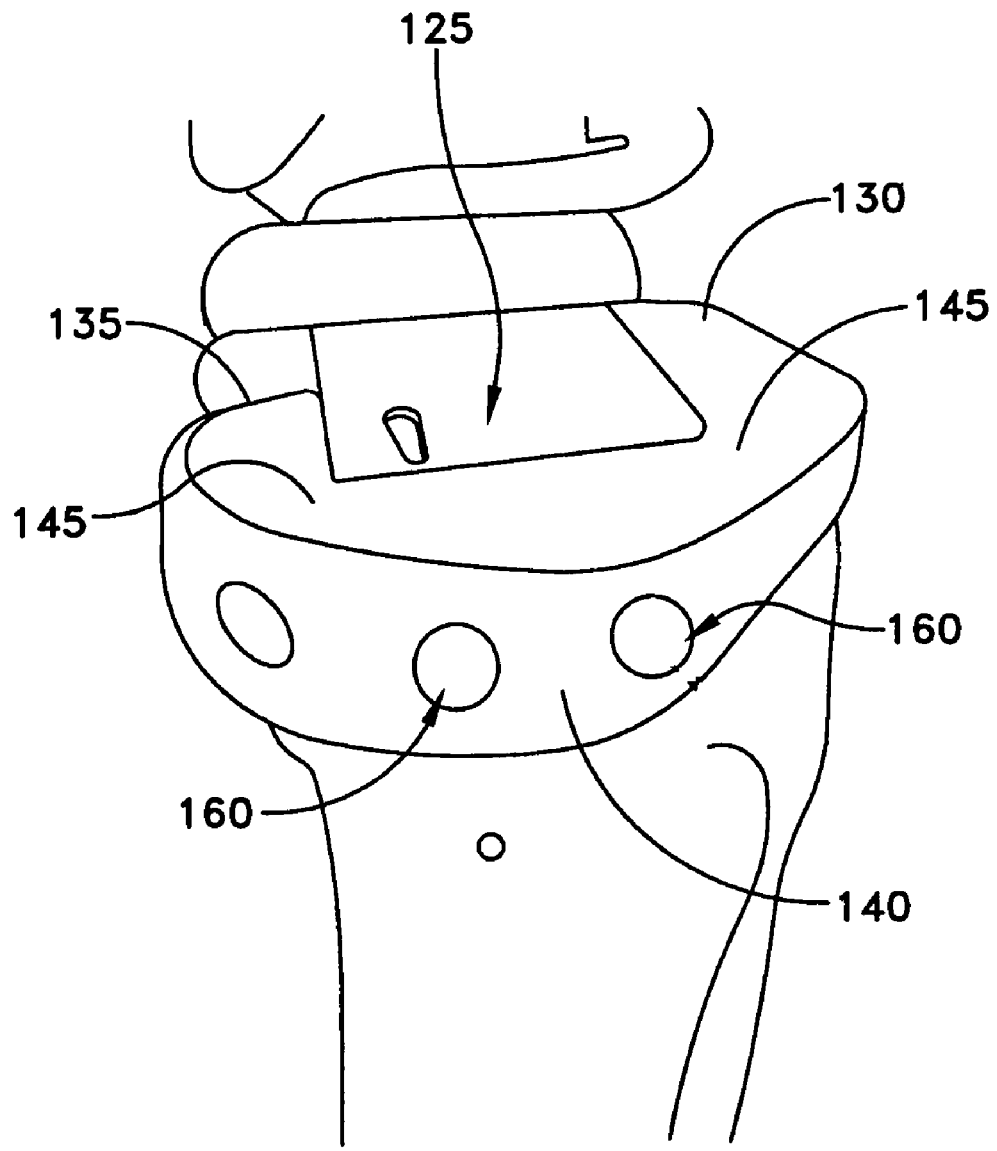
Figure 28:
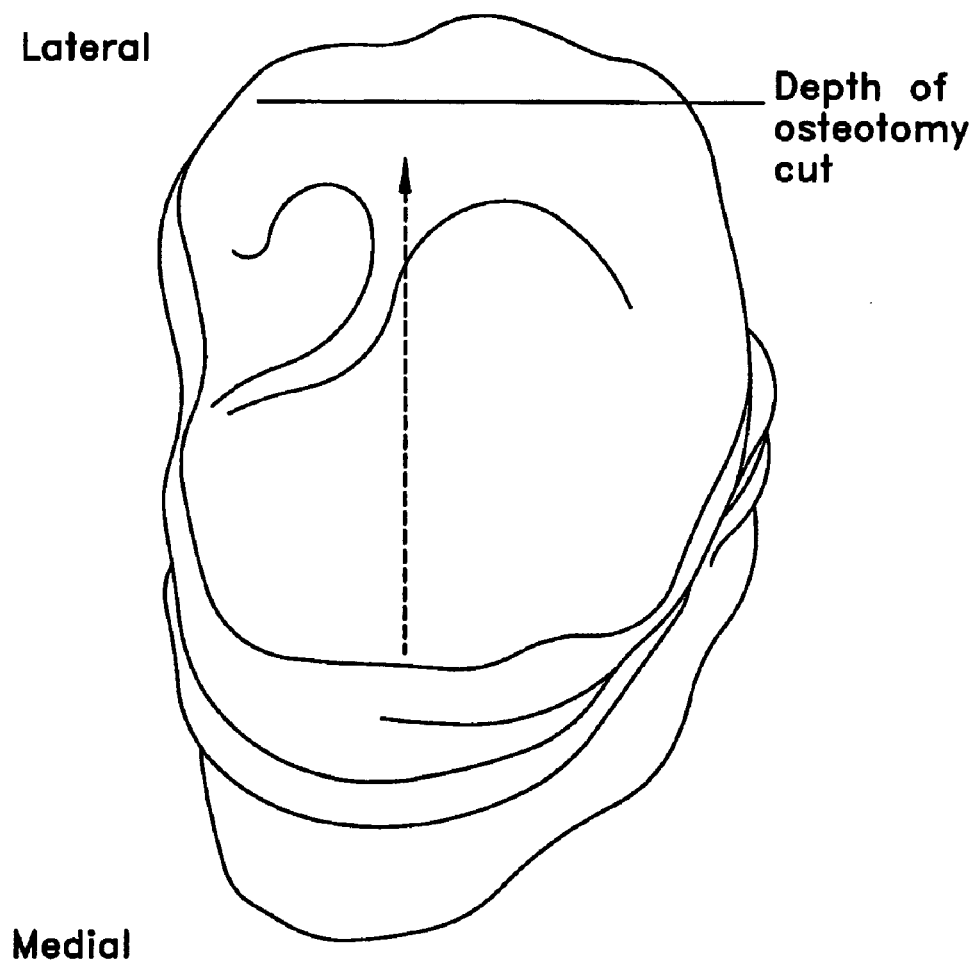
FIGS. 28-31 are schematic views of a medial-to-lateral approach for an osteotomy procedure.
Figure 29:
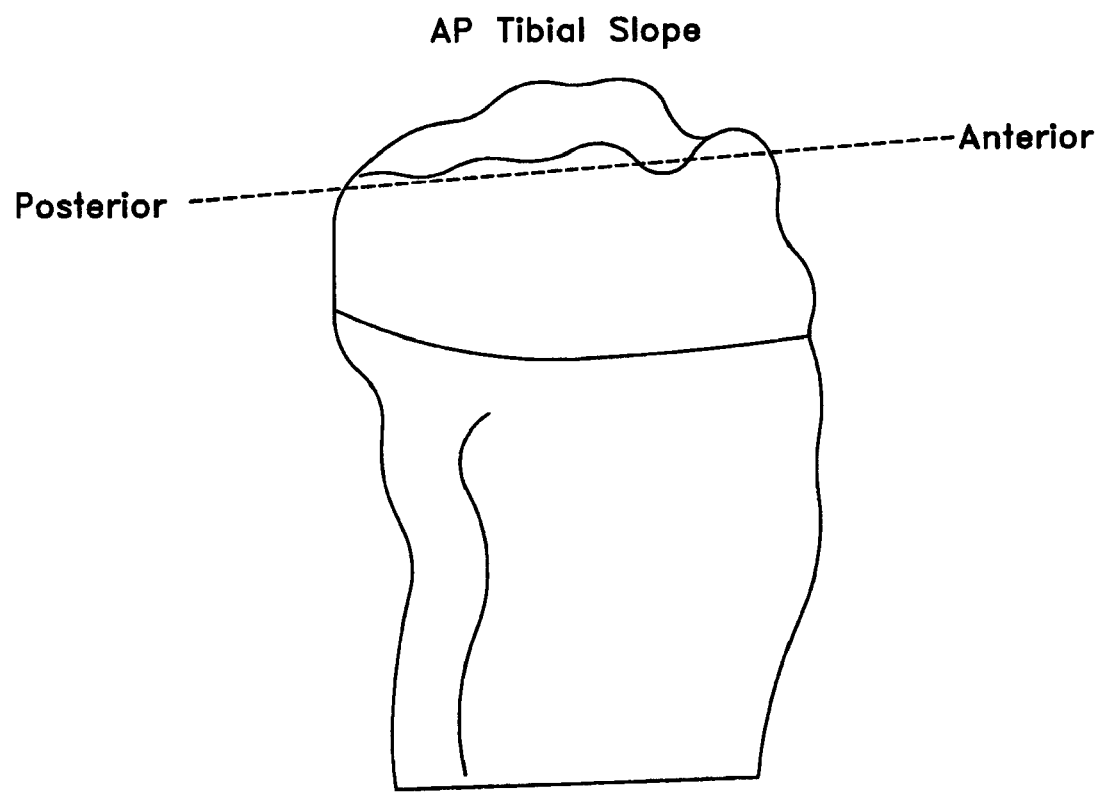
Figure 30:
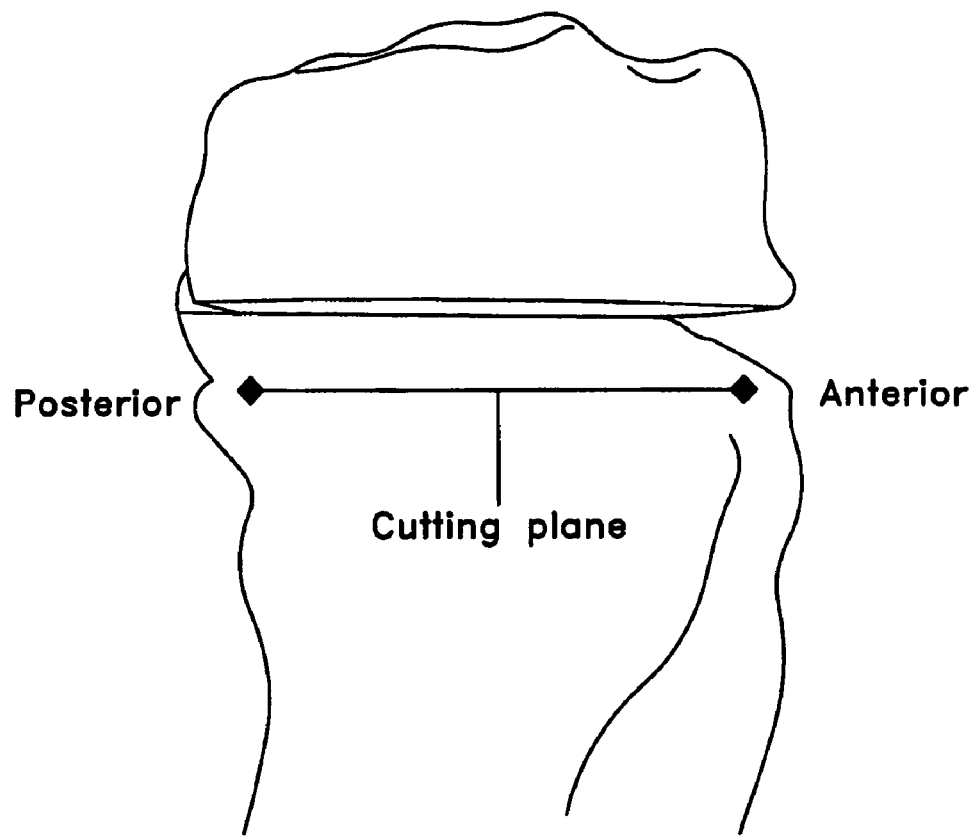

A set of fixation holes 160 (FIG. 23) are provided in base part 140 to secure the assembled implant 125 to the tibia using fixation screws 175 (FIG. 26). Base fixation holes 160 are preferably disposed at an angle relative to one another so as to direct at least one fixation screw 175 into tibia 10 on each side of void 110. More particularly, bone interface surface 140A (FIG. 23) of base part 140 engages one of the bone surfaces forming void 110 of tibia 10. Fixation hole exit 160A emerges through surface 140A so as to allow a fixation screw 175 (FIG. 26) to pass into the surrounding tibia bone 10. Fixation screw 175 enters tibia 10, whereby to fix base 140 (and hence the entire implant 125) to tibia 10.

Anterior part 130 and posterior part 135 of implant 125 preferably include injection ports 165 (FIG. 22) leading to channels 170. Channels 170 extend through anterior part 130 and posterior part 135 and exit on the upper and lower surfaces of anterior part 130 and posterior part 135, whereby to communicate with the part/bone interface. Injection ports 165 permit material (e.g., bone cement, bone paste, growth enhancers, etc.) to be delivered to the part/bone interface.

Anterior part 130, posterior part 135 and/or base part 140 may be formed out of one or more resorbable materials, whereby they may be resorbed into the host bone.

In one preferred form of the invention, anterior part 130, posterior part 135 and base part 140 are all formed out of a biomaterial and/or a biocomposite that resorbs into the host bone, with anterior part 130 and posterior part 135 being formed so that they resorb faster than base part 140. By forming base part 140 out of a longer-lasting biomaterial and/or biocomposite, base part 140 can provide lasting strength and support for the osteotomy to ensure optimal bone growth within void 110.

Preferably the area within osteotomy void 110 is filled with bone cement, bone paste, growth enhancers, etc. during the procedure, so that the osteotomy void 110 bounded by multi-part implant 125 will create bone or bony ingrowth over time. This may be done (i) after anterior part 130 and posterior part 135 are deployed in the osteotomy void, and (ii) before base part 140 is secured to parts 130 and 135. Alternatively, additional through holes (not shown) may extend through base part 140, whereby to permit the interior of osteotomy void 110 to be accessed even after the multi-part implant is assembled in the osteotomy void.

Osteotomy Procedure

An osteotomy procedure may be conducted using a medial-to-lateral approach or an antero-medial approach.

(i) Medial-To-Lateral Approach

Looking next at FIGS. 28-31, there is shown a medial-to-lateral approach with a specified depth of an osteotomy cut.

With prior art systems and methods, using the medial-to-lateral approach may allow the surgeon to more easily obtain the correct AP tibial slope, which is crucial to knee stability. In addition, with prior art systems and methods, the medial-to-lateral approach may allow the surgeon to more easily control the cutting plane from posterior to anterior.

However, in practice, the medial-to-lateral approach can be difficult to execute with prior art systems and methods due to the presence of soft tissue structures such as the medial collateral ligament attachment site. Therefore, with prior art systems and methods, it may be preferred to use an antero-medial approach.

(ii) Antero-Medial Approach

Figure 32:
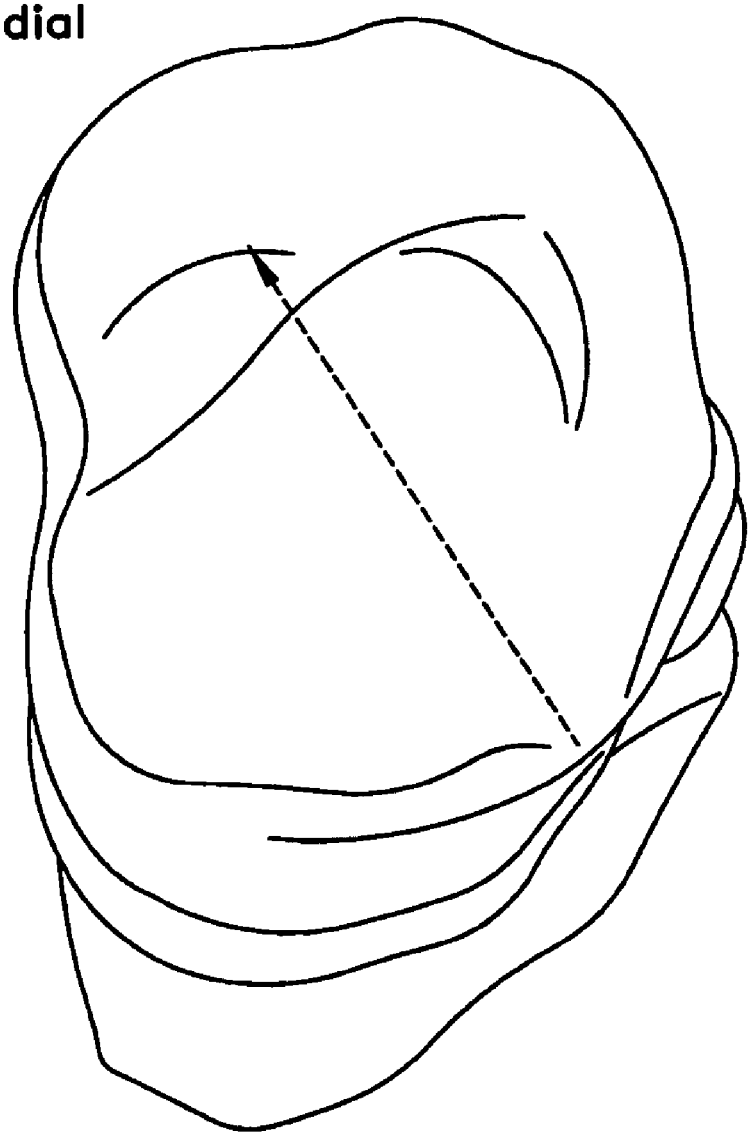
FIGS. 32-34 are schematic views of an antero-medial approach for an osteotomy procedure.
Figure 33:
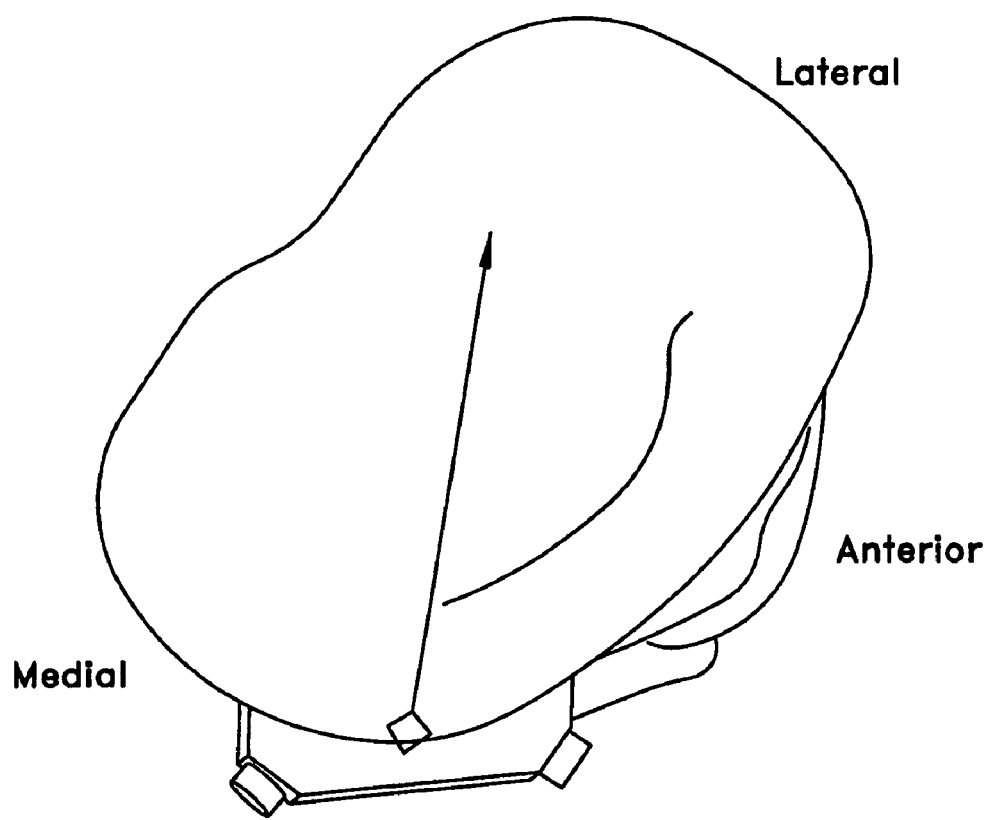
Figure 34:
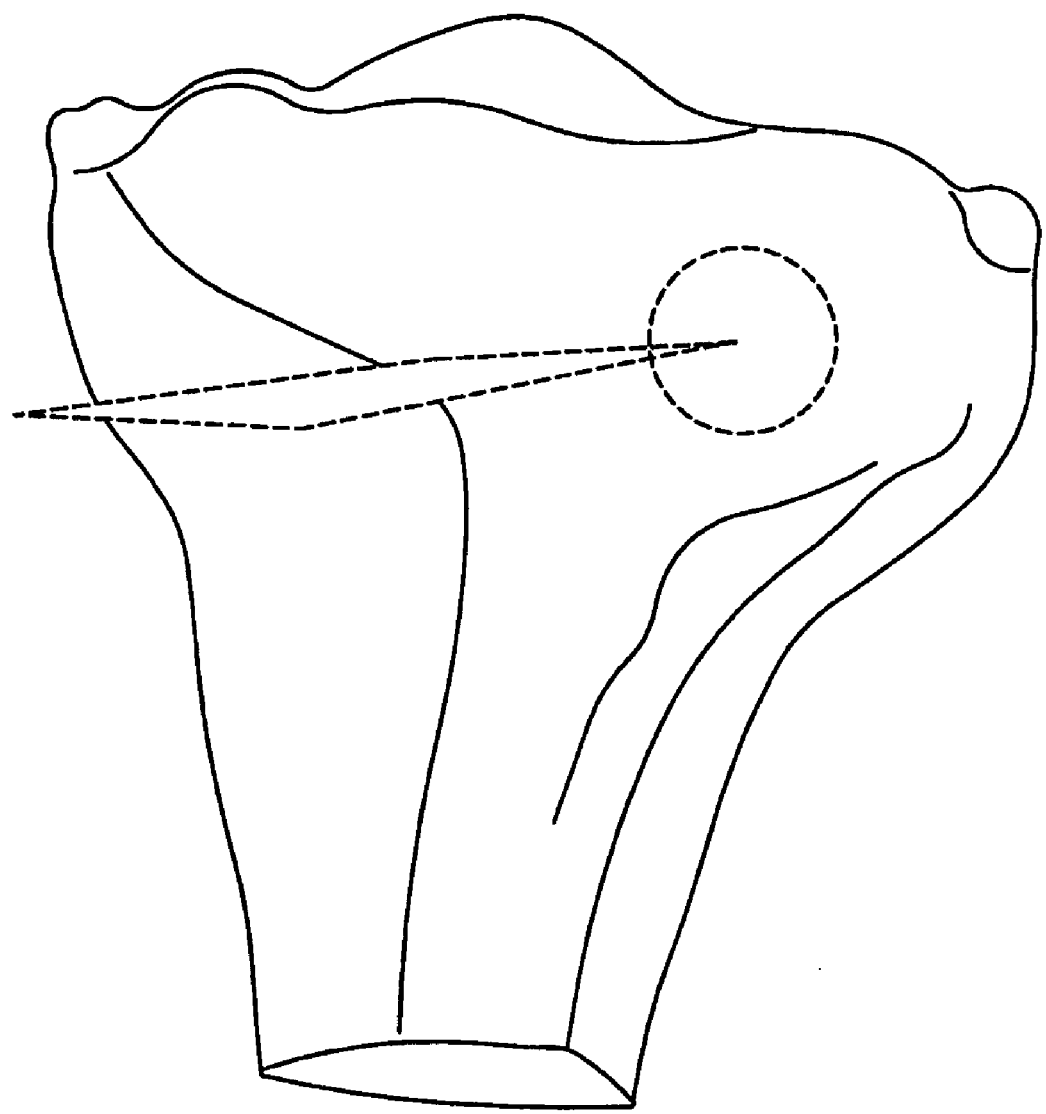

Referring next at FIGS. 32-34, with prior art systems and methods, the antero-medial approach may present difficulties in maintaining a controlled cutting plane. With prior art systems and methods, it is generally not possible to ensure a cutting plane that is offset at a fixed angle to the sagittal plane so as to maintain the existing anterior-posterior (AP) tibial slope. Essentially, with prior art systems and methods, which are hand-guided and directed, the actual cutting plane is made by means of two or more angular adjustments in an oblique fashion to the sagittal plane while the bone is being resected. Once the osteotomy is opened and the osteotomy void is created, it is this offset and oblique angles that make it difficult to maintain the patient's anatomical tibial slope.

If the anatomical AP slope is not maintained or controlled, the patient may experience postoperative knee instability. In addition, several surgeons have begun to address knee instability problems (due to knee ligament laxity or damaged knee ligaments) by making planned adjustments to the patient's AP tibial slope. Such important planned changes to the slope must be accurate and carried out methodically.

When performing an opening wedge osteotomy, and more specifically a high tibial osteotomy, there are a number of important elements that need to be executed by the surgeon in order to achieve a positive surgical outcome.

One important element is to maintain the anterior-to-posterior (AP) tibial slope.

Another important element is to maintain and control the plane in which the bone cut is made.

Still another important element is to provide a fixation system that promotes physiologic healing and regeneration of new bone in order to provide for a long lasting osteotomy.

Yet another important element is to support the osteotomy void during healing in order to maintain the AP tibial slope and protect the bone grafting materials used to enable new bone growth.

In prior art systems and methods for carrying out an antero-medial approach, the above criteria are generally not easily met. As a result, the published literature generally teaches that the best approach for making the bone cut is a direct medial-to-lateral approach.

Significantly, the present invention provides an improved system and method for an opening wedge osteotomy using an antero-medial approach.

(iii) Preferred Method

Figure 31:
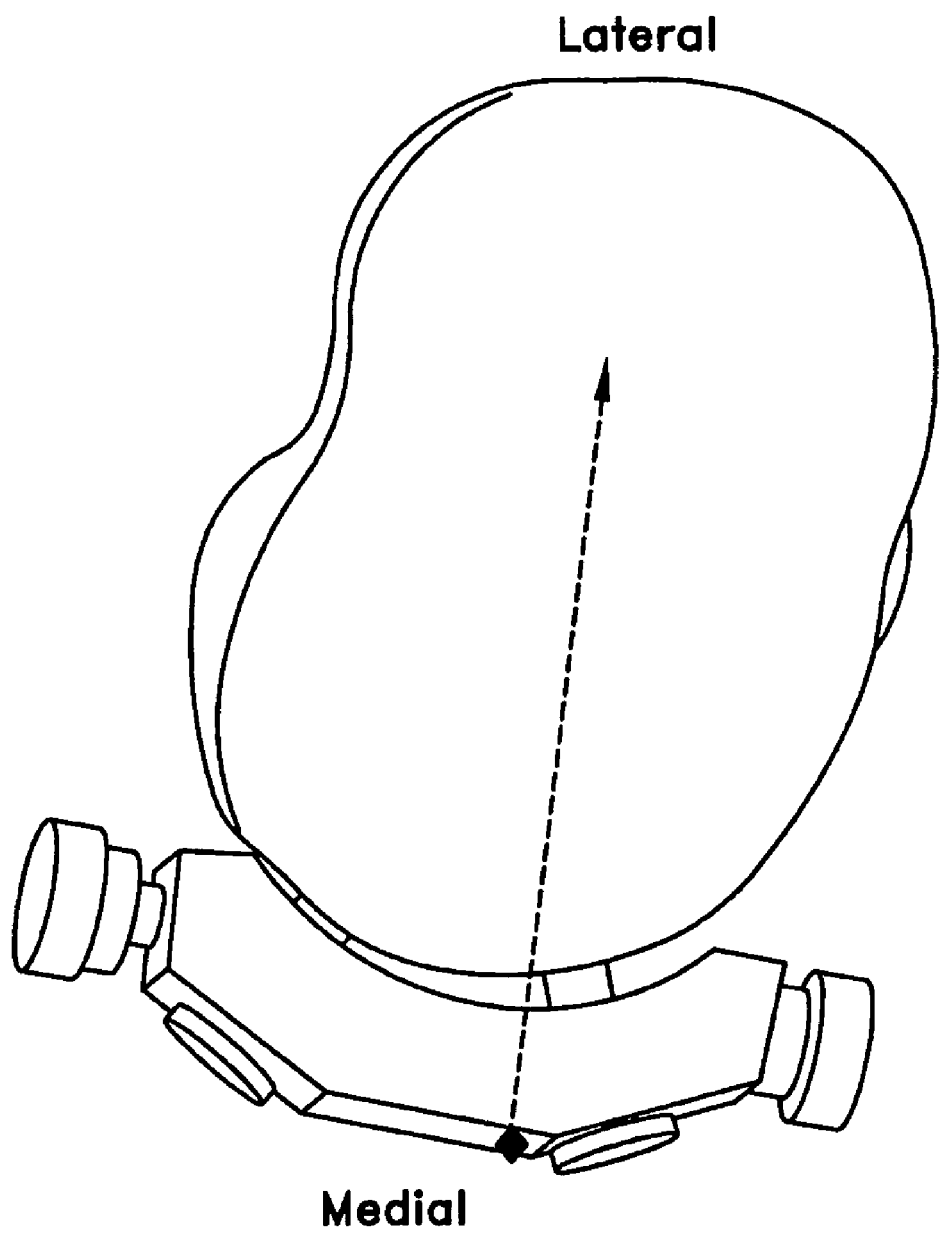

Referring next to FIG. 31, there is shown a medial-to-lateral approach which, as noted above, is discussed in much of the medical literature as being the "best" approach to make a bone cut in a sagittal plane. However, in practice, this can be a difficult procedure due to the attachments of the medial collateral ligaments.

Looking now at FIG. 33, the present invention preferably uses an antero-medial approach, with the position of the bone cut being established through the use of the positioning guide 20 and cutting guide 45, as discussed above and as will hereinafter be discussed in further detail below.

Figure 35:
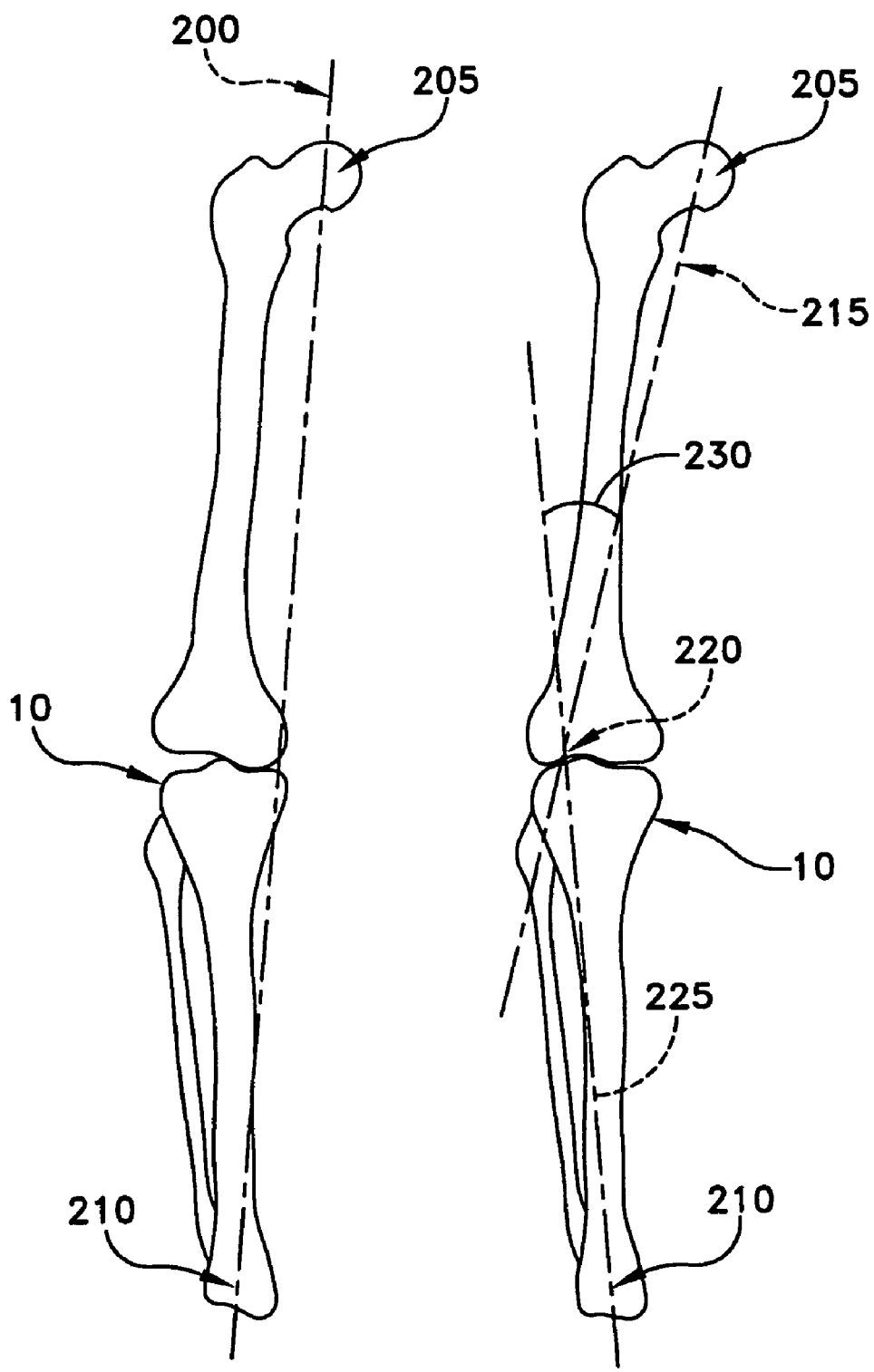
FIGS. 35-37 are schematic views of a method to determine the corrective alignment to be made to a patient's femoral head to tibial-talar joint mechanical axis.
Figure 36:
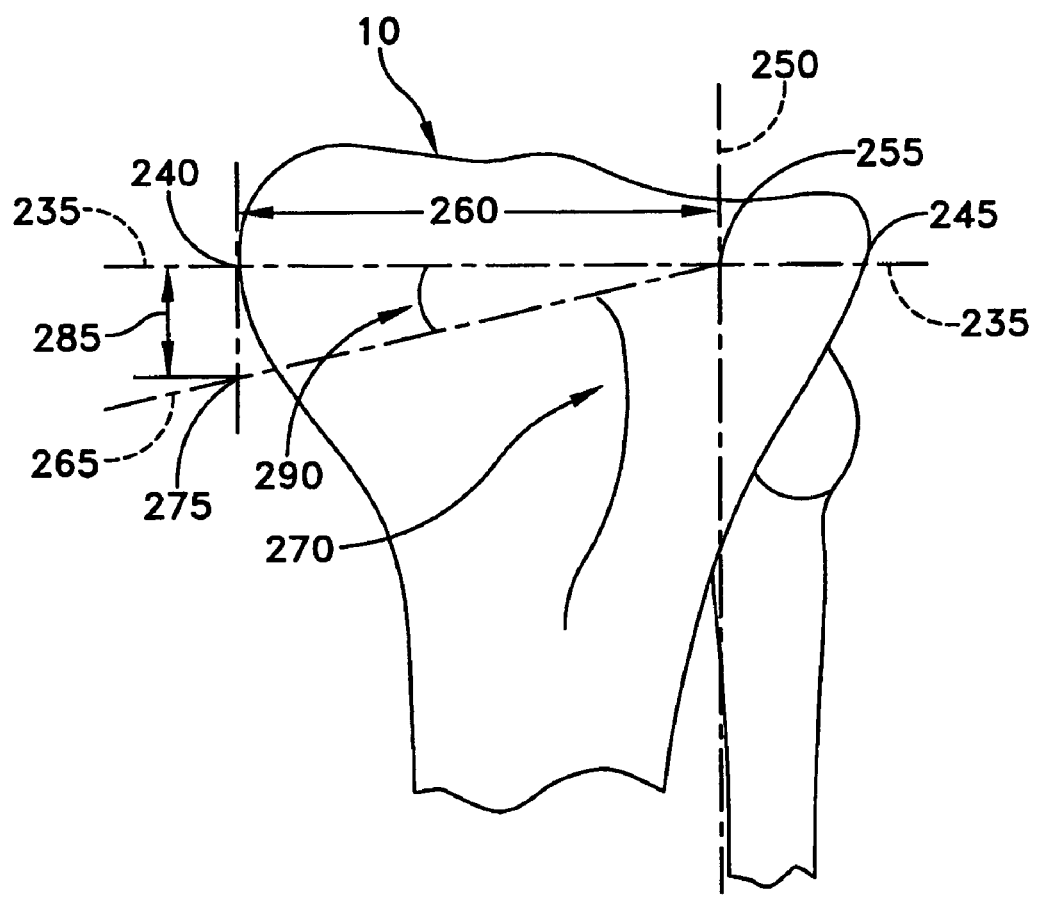
Figure 37:
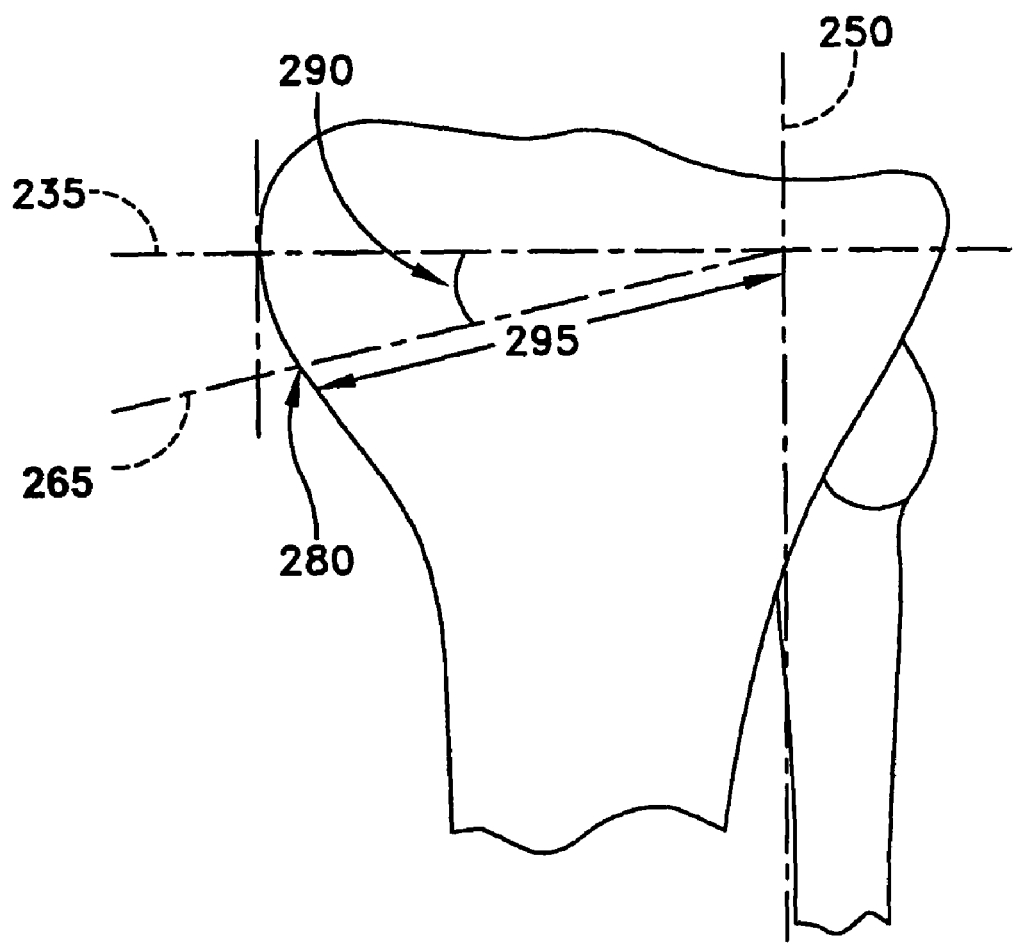

Referring now to FIGS. 35-37, there are a number of documented techniques by which the surgeon may determine the precise corrective alignment that is to be established by the osteotomy being performed. All of the techniques commonly used generally require full length standing AP and lateral radiographs. Typically, a line 200 is drawn from the center of the femoral head 205 to the center of the tibial-talar joint 210 (FIG. 35). This represents the patient's present mechanical axis. Another line 215 is drawn from the center of the femoral head 205 to a point 220 located at 62.5% of the width of the proximal tibia in the lateral knee joint. A third line 225 is drawn from the center of the tibial-talar joint 210 to the same point 220 in the lateral knee joint. An angle 230, formed by the intersection of the two lines 215 and 225, determines the degree of correction required to return the patient's mechanical axis to the point of intersection on the lateral side.

Next, the surgeon must determine the cutting depth of the osteotomy and the properly sized, slotted cutting guide 45 to be used for the procedure.

Referring now to FIG. 36, on a radiograph, the surgeon first draws a line 235 from a portion 240 of the medial cortex of the tibia to the lateral cortex that is 1 cm below the joint line. Next, a line 250 is then drawn that is (i) perpendicular to line 235, and (ii) equal to, or greater than, 1 cm from lateral cortex 245 of tibia 10. Point 255, where line 235 and line 250 intersect, marks the appropriate depth of the bone cut to be made across tibia 10. A distance 260 is measured from the medial cortex 240 to the intersecting point 255. Distance 260 is the maximum distance (or depth) of the bone cut which is to be performed.

Next, the surgeon calculates the point of entry for the osteotomy bone cut. A line 265 is drawn from the intersecting point 255, angled inferiorly but remaining above the anterior tibial tubercle 270, to a point 275 which lies on the vertical line dropped from the aforementioned portion 240 of the medial cortex. The initial point of entry 280 (FIG. 37) for performing the resection lies on line 265, and can be calculated as the distance 285 between point 240 and point 275.

The oblique resecting angle 290 is calculated from the inside wedge angle formed by points 240, 255 and 275 (FIG. 36).

Through such preoperative planning, the surgeon can calculate the required positioning of the bone cut which will be used to form an osteotomy void which, in turn, will be used to effect the corrective angle 230 (FIG. 35). More particularly, prior to initiating the osteotomy, the surgeon can calculate: (i) the point of entry 285 on the medial cortex for the bone cut; (ii) the depth of the resection 295; and (iii) the oblique angle 290 of the bone cut across tibia 10 to remain above anterior tibial tubercle 270.

Once the surgeon has identified the proper attributes of the bone cut, the surgeon then uses the method and apparatus of the present invention to effect the bone resection. More particularly, the surgeon preferably:

(i) attaches positioning guide 20 to the proper location on patient's tibia;

(ii) selects the proper cutting guide 45 to be attached to positioning guide 20, whereby to define the target slope (or plane) of the cut to be made in the tibia;

(iii) selects the proper protector members 70, 75 to be attached to the cutting guide 45, whereby to protect the soft tissue and neurovasculature structures surrounding the tibia;

(iv) secures the cutting guide 45 to positioning guide 20, and then secures protector members 70, 75 to the cutting guide 45;

(v) selects the proper cutting blade 65 to be used in the procedure, whereby to define the proper depth of the cut to be made in the tibia;

(vi) passes cutting blade 65 through guide slot 50 formed in cutting guide 45 and through tibia 10, following the pathway 65A established by cutting guide 45, until the cut has been made to the proper depth;

(vii) withdraws cutting blade 65;

(viii) uses mechanical jack 90 to open the cut in the bone to the proper angle; and (ix) inserts the multi-part implant 125 into the osteotomy void 110 created in the bone, whereby to hold the resected tibia in the proper configuration.

Preferably, bone cement or bone paste, etc. is inserted into the interior of the osteotomy void, within multi-part implant 125, whereby to facilitate strong bone growth and/or bony ingrowth; and preferably bone cement is injected into the implant/bone interface to help further secure the multi-part implant to the bone.

Significantly, with the present invention, the bone cut is made easily and reliably using an antero-medial approach, while providing excellent protection of the soft tissue and neurovasculature structures surrounding the tibia. Furthermore, osteotomy stabilization is achieved through the use of an implant device that provides stability about the osteotomy site while allowing the direct contact of bone graft material with native bone within the open wedge osteotomy. Significantly, the present invention also allows for the necessary physiologic compression and stimulation required to promote new tissue and bone growth through the bony void. This is in sharp contrast with prior art open wedge osteotomy systems, which use fixation plates and screws to maintain and support the corrective wedge opening; such systems do not allow beneficial physiologic compressive forces to act on the bone/graft interfaces. This can lead to nonunion osteotomies and failed corrections.

As noted above, the bone cut typically penetrates to within a centimeter or so of the lateral side of the tibia. In some circumstances, the subsequent opening of the osteotomy void may result in cracking at the far bone hinge. Therefore, and looking now at FIG. 34, it may be desirable to pass a small bone cutting burr along the far edge of the bone hinge, so as to remove possible stress risers that may exist and help reduce the risk of fracture when opening the osteotomy cut into wedge void 110. To the extent that the method includes such a stress-riser-reduction step, it is preferably done after making the bone cut and before opening the osteotomy void.

Alternative Mechanical Jack 300

Referring now to FIGS. 38-47, in an alternative form of the invention, a mechanical jack 300 may be used in place of the aforementioned mechanical jack 90.

Figure 38:
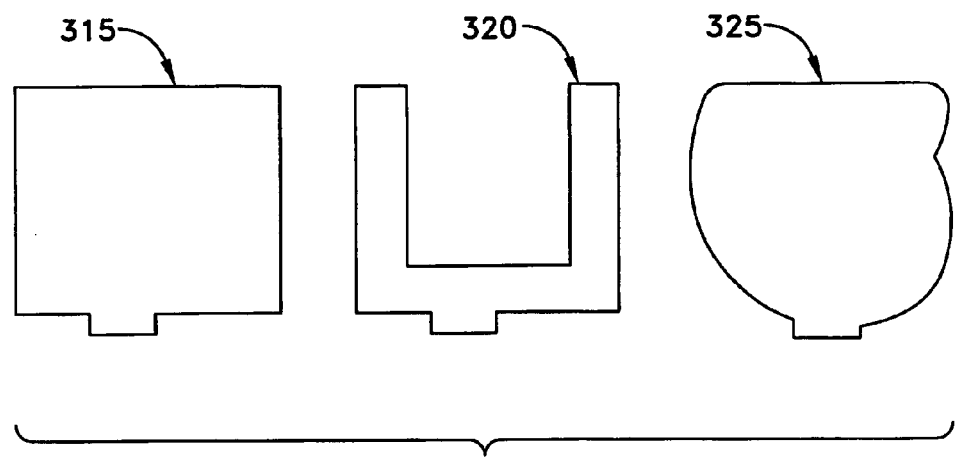
FIGS. 38-47 are schematic views of an alternative mechanical jack 300 which is illustrative of an alternative component of a preferred embodiment of the novel osteotomy system.
Figure 39:
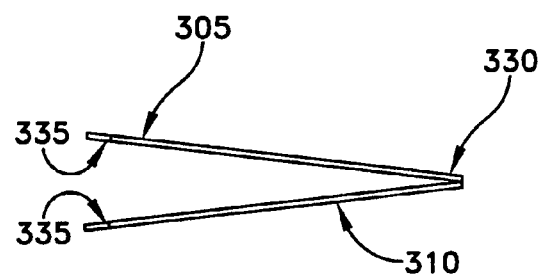
Figure 40:
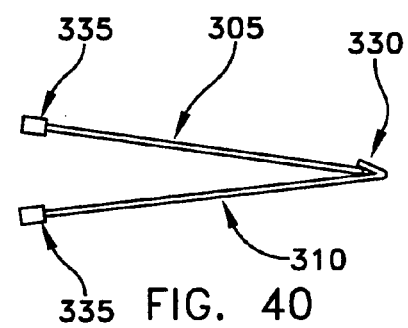
Figure 41:
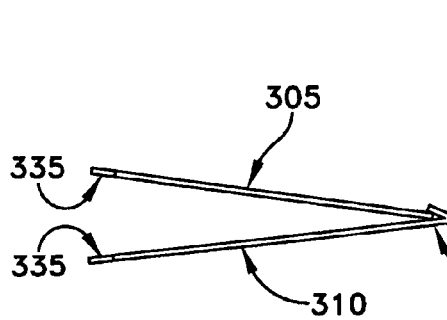
Figure 42:
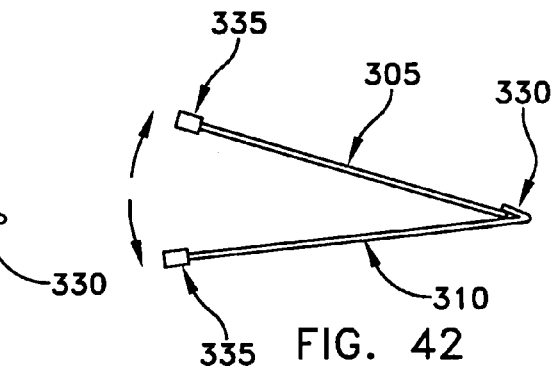
Figure 43:
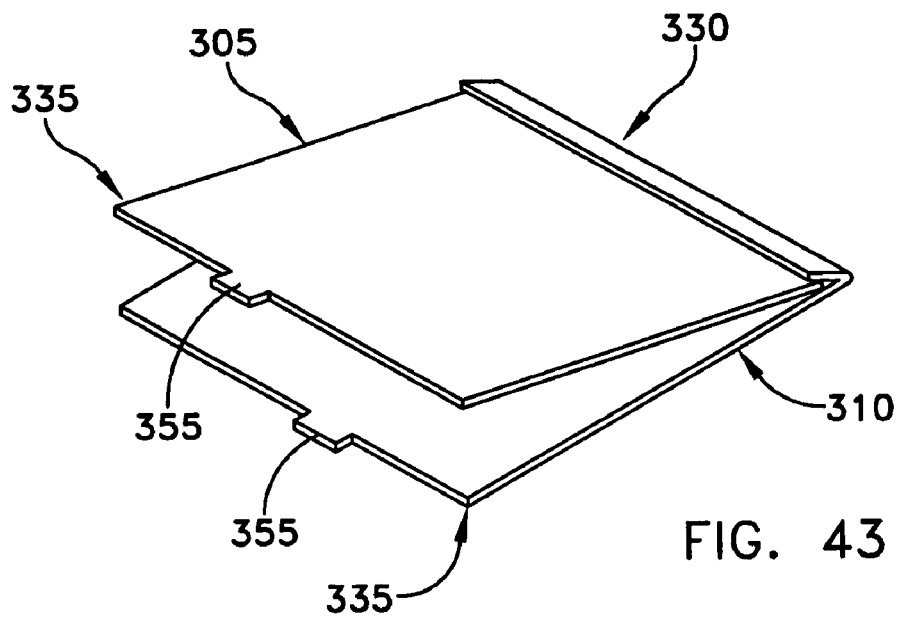

More particularly, mechanical jack 300 preferably comprises two plates 305, 310. Plate 305 is disposed in the tibial bone cut in a superior position, and plate 310 is disposed in the tibial bone cut in an inferior position. As seen in FIG. 38, plates 305, 310 may comprise one or more varying shapes 315, 320, 325, etc. A preferred shape for plates 305, 310 is oblong, measuring about 15-20 mm across and about 40-70 mm long. Plates 305, 310 are preferably configured to extend substantially the entire depth of the bone cut, in order to provide ample support when opening the bone. Both plates 305, 310 connect or join to each other at their distal ends 330 and allow their proximal ends 335 to open relative to one another, whereby to form an opened wedge.

Figure 44:
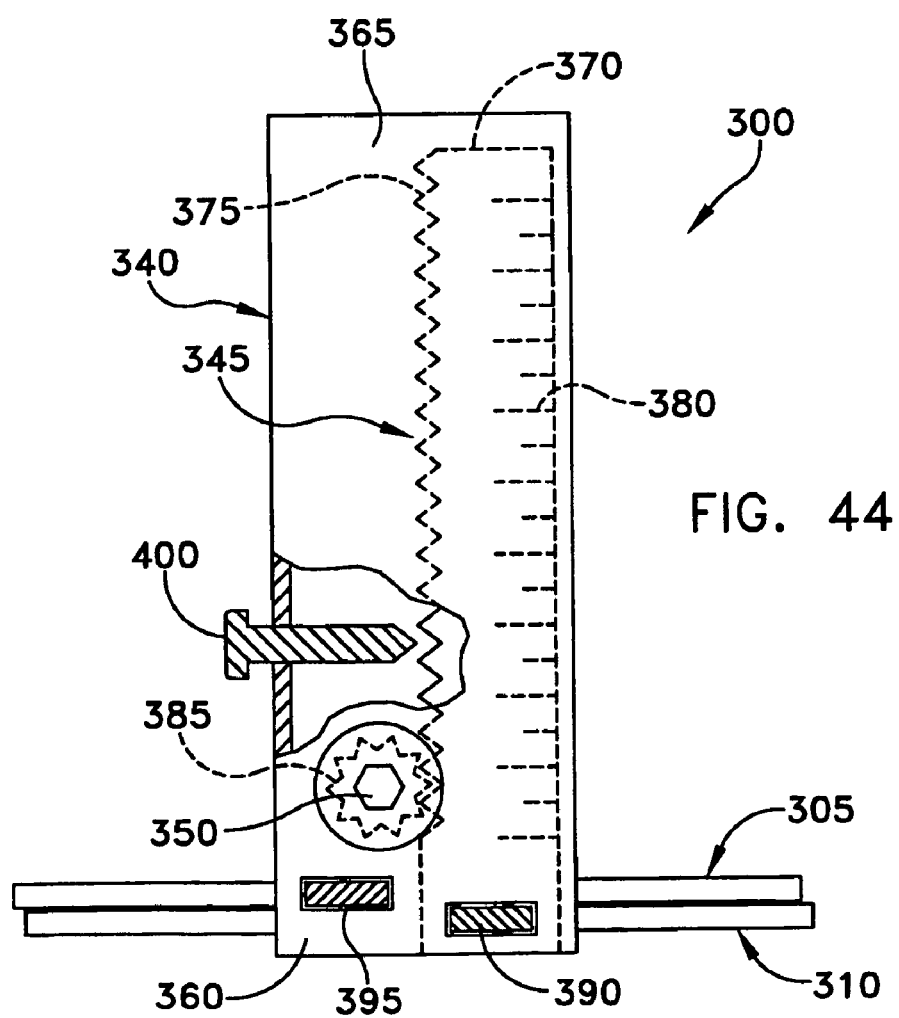

Plates 305, 310 are coupled with a mechanical device 340 (FIG. 44) that provides a deliberate degree of opening of the bone cut. Mechanical device 340 preferably comprises a rail system 345 and an actuation device 350 (FIG. 44). At the proximal end 335 of each plate 305, 310 is a male projection 355 that allows attachment of the plates to actuator housing 360. Actuator housing 360 preferably comprises a rectangular shaped plate 365 that houses at least one sliding member 370 with ratchet teeth 375. Sliding member 370 preferably comprises calibration markings 380 in specific measurements. Calibration markings 380 may be in various units of measurement including, for example, angle in degrees or millimeters of opening. Actuator housing 360 preferably measures approximately 1 cm wide×2 cm long×3-5 mm deep. Actuation device 350 is rotatably fixed to housing 360 so that teeth 385 engage teeth 375 on sliding member 370. As a result of this construction, when actuation device 350 is rotated, it effectively moves the sliding member 370 up or down (depending on the direction of rotation), whereby to open or close the plates 305, 310 relative to one another. Sliding member 370 preferably measures about 5 mm wide×2 cm long×2-4 mm thick, and has a female-type connector 390 (FIG. 44) positioned in the center that fits with the male-type projection 355 of inferior plate 310; correspondingly, housing 360 preferably has a female-type connector 395 that fits with the male-type connector 355 of superior plate 305. Preferably, a locking pin 400 is also provided which, once pushed inward, fits into gear teeth 375 of sliding member 370, whereby to prevent movement of sliding member 370.

In an alternative preferred embodiment (not shown), a circular actuator is configured to drive two sliding members in opposing directions relative to one another so as to open up or close down plates 305, 310 with respect one another.

Figures 45, 46:
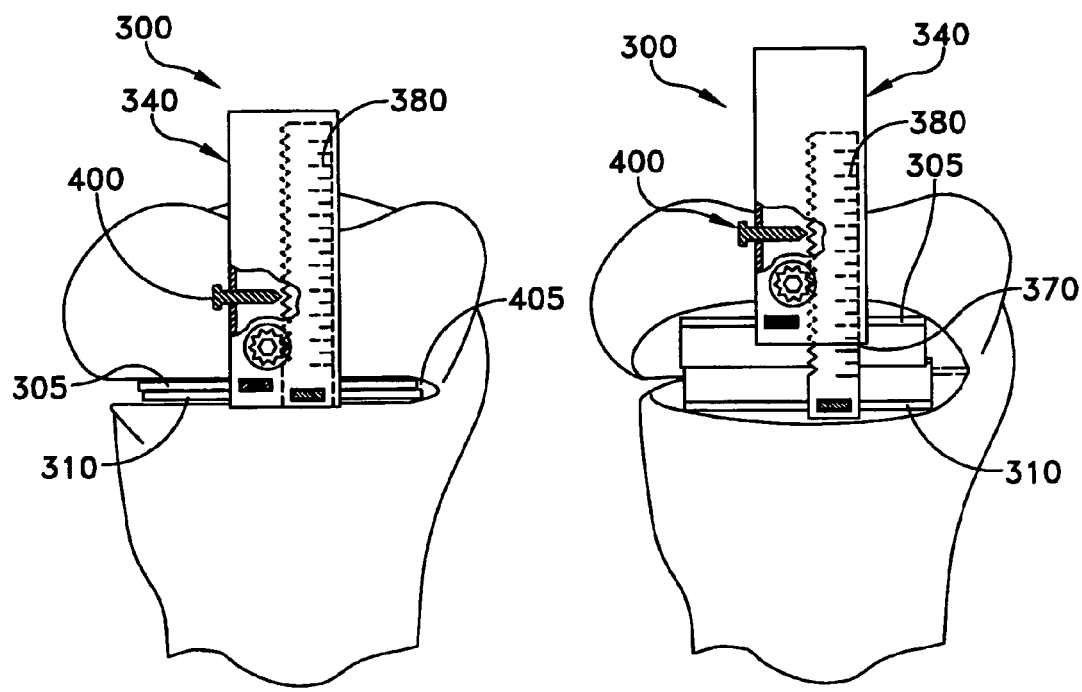
Figure 47:
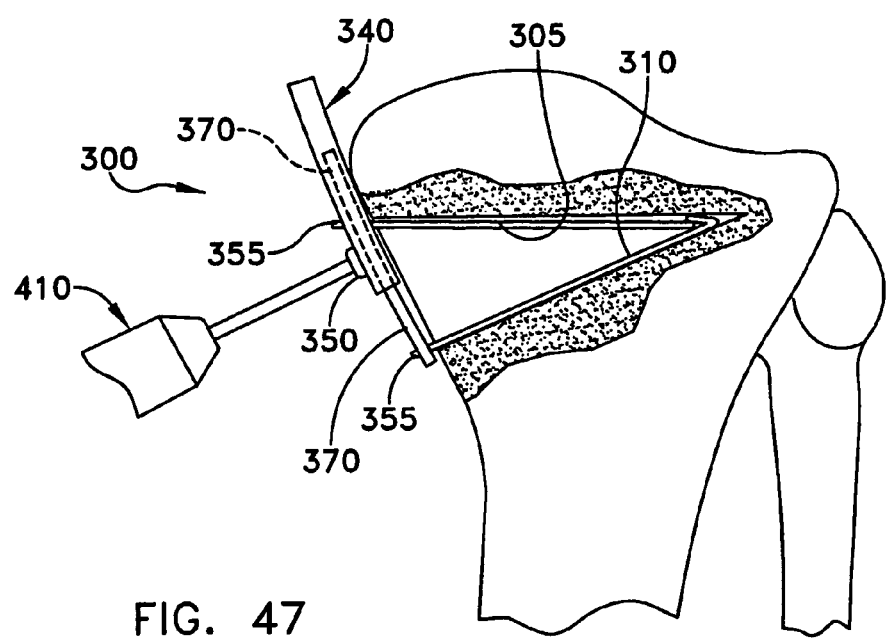

Referring now to FIGS. 45-47, operation of mechanical jack 300 is illustrated. More particularly, plates 305, 310 are slid into a previously-made bone cut 405. A hand driver tool 410 is preferably used to rotate the actuator device 350 in a direction that begins to open plates 305, 310 into a wedge configuration. As the wedge is opened, the surgeon notes the position of calibration markings 380 on sliding member 370 (FIG. 46) and opens the plates 305, 310 to the desired angle of bone reconfiguration (which was determined preoperatively). Once the corrective angle is achieved, locking pin 400, which is preferably located on the side of actuator housing 360, is slid into place so as to prevent movement of sliding member 370. Thereafter, the osteotomy may be conducted in the manner previously discussed, i.e., the surgeon inserts the multi-part implant 125 into the opening in the bone, whereby to stabilize and secure the open wedge osteotomy.

Alternative Implants 500

Figure 48:
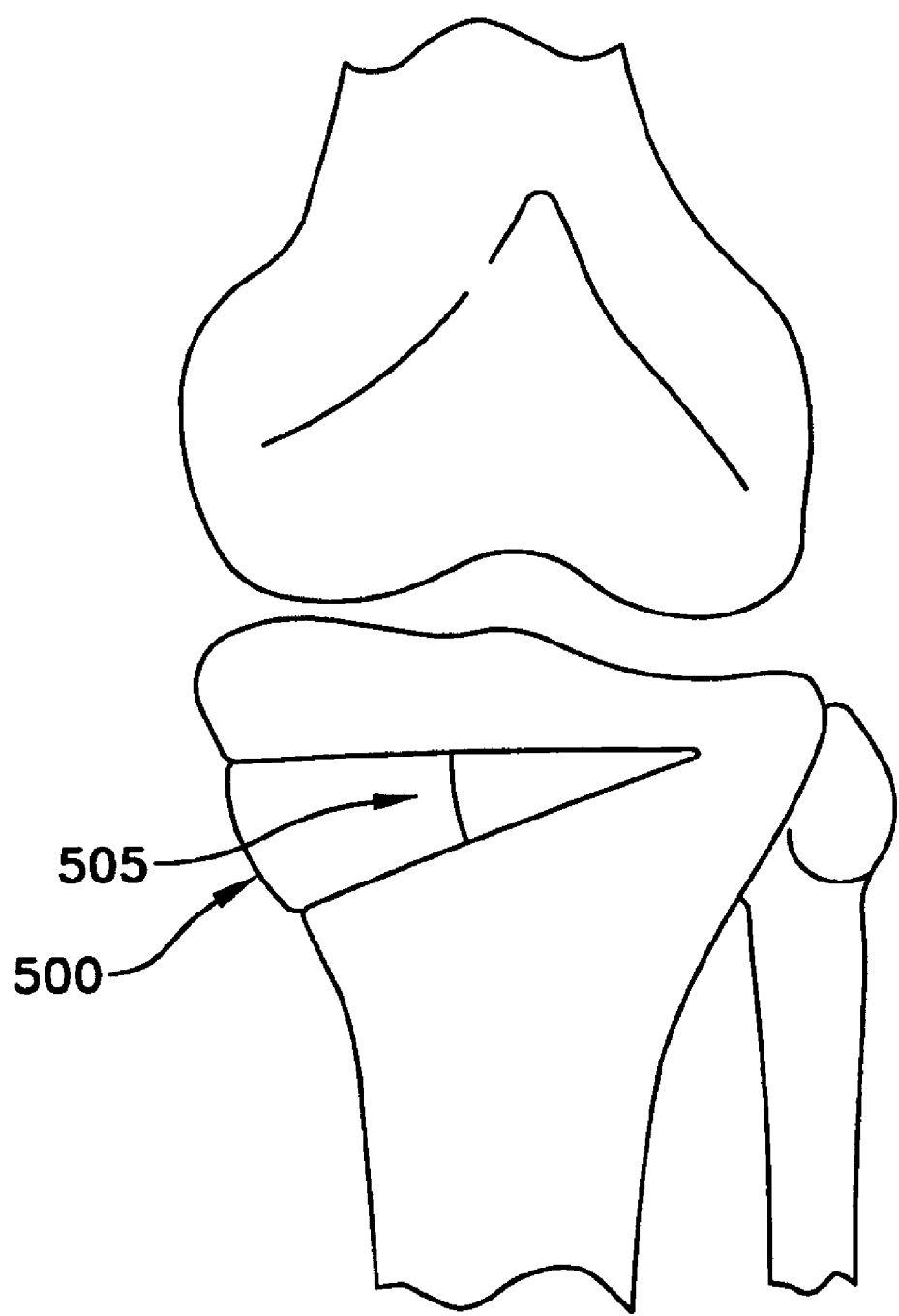

In alternative embodiments of the present invention, and referring now to FIGS. 48-60, 61-68, 69-74, 75-78, 79-87 and 88-89, the osteotomy procedures described above may be practiced using an alternative implant 500 substituted for the multi-part implant 125 described above. Preferably, the alternative implant 500 utilizes a design that frames the perimeter of the osteotomy void 110 and acts as a strut for supporting tibia 10 at the corrective angle 505 (FIG. 48).

Figure 50:
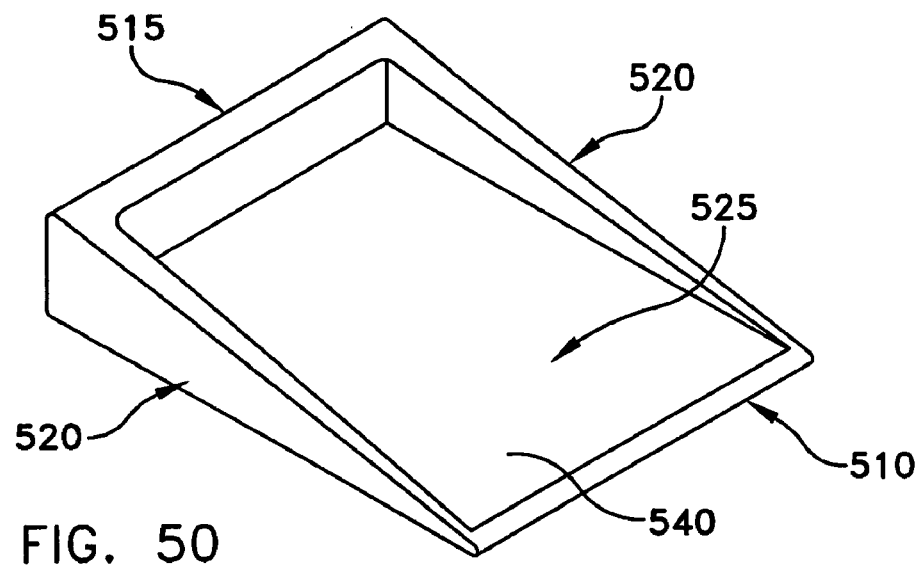
Figure 51:
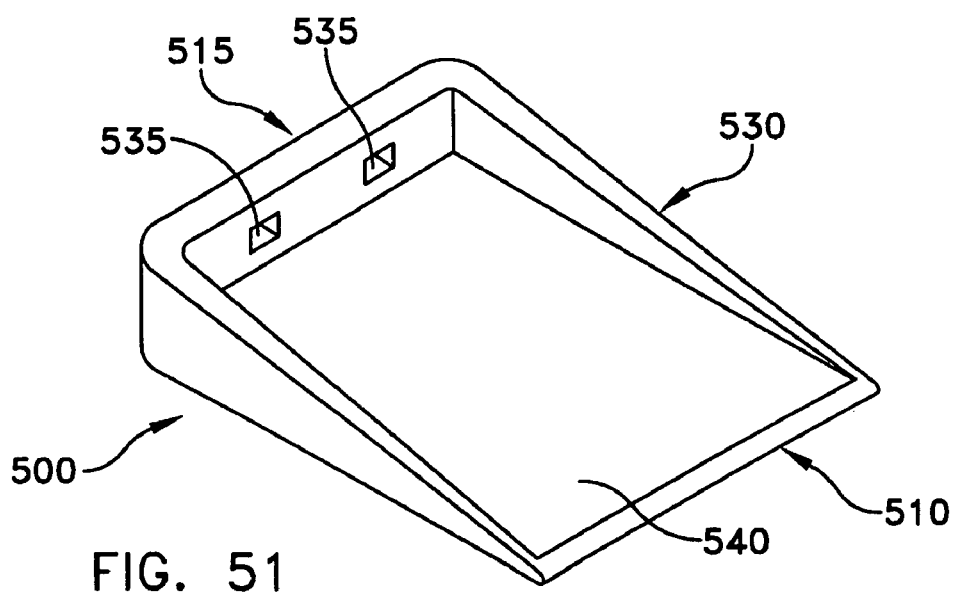
Figure 52:
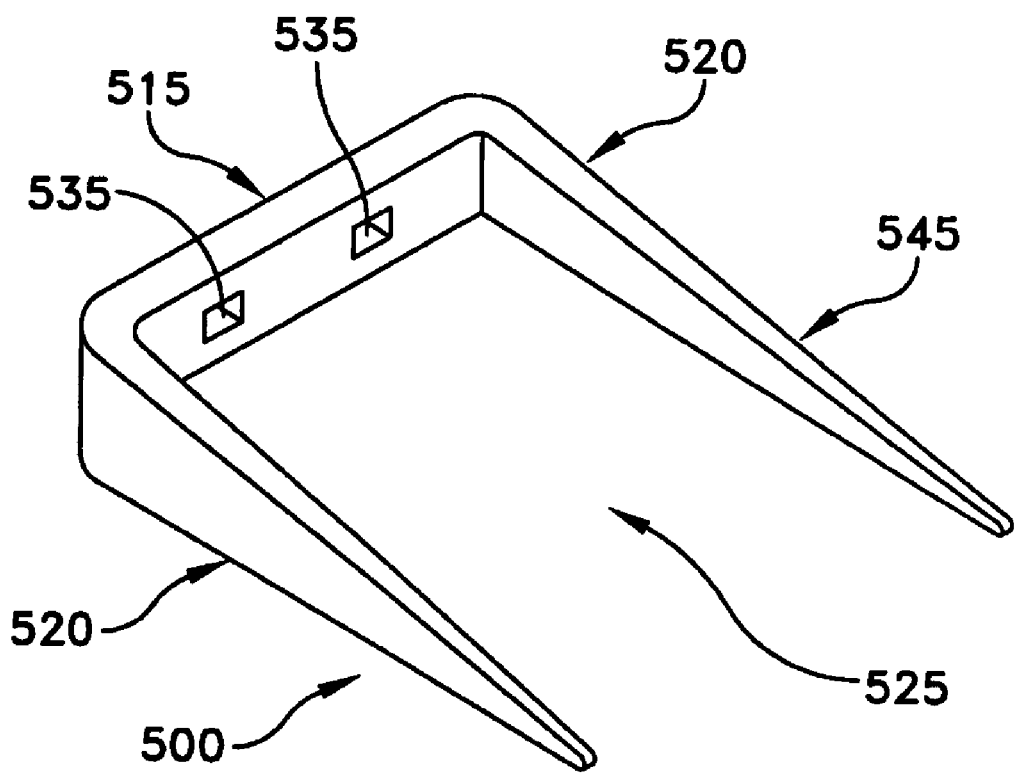
Figure 53:
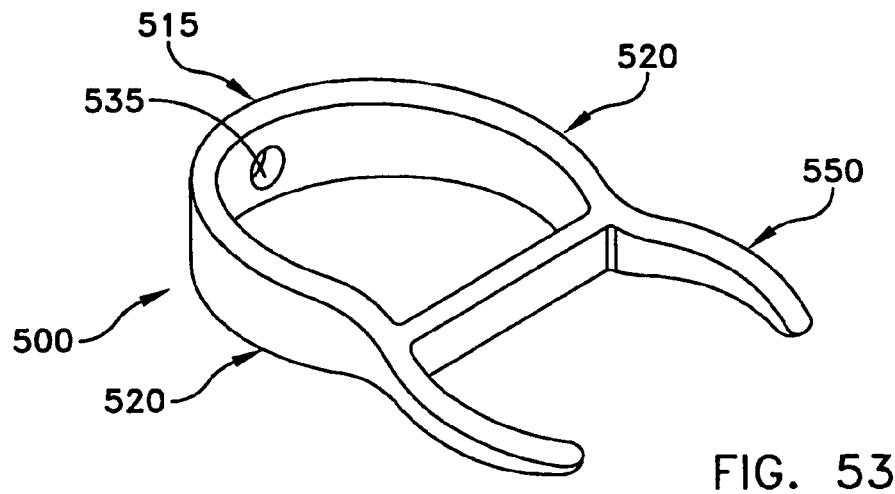
Figure 54:
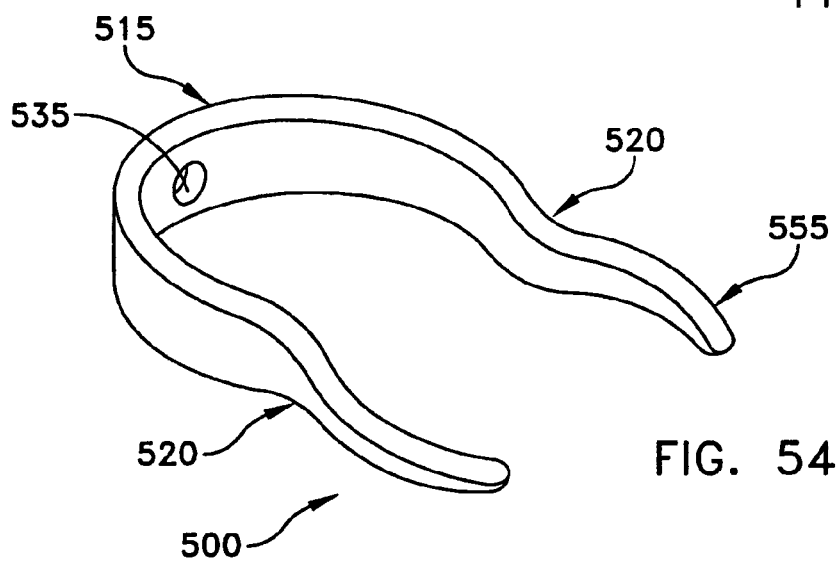
Figure 55:
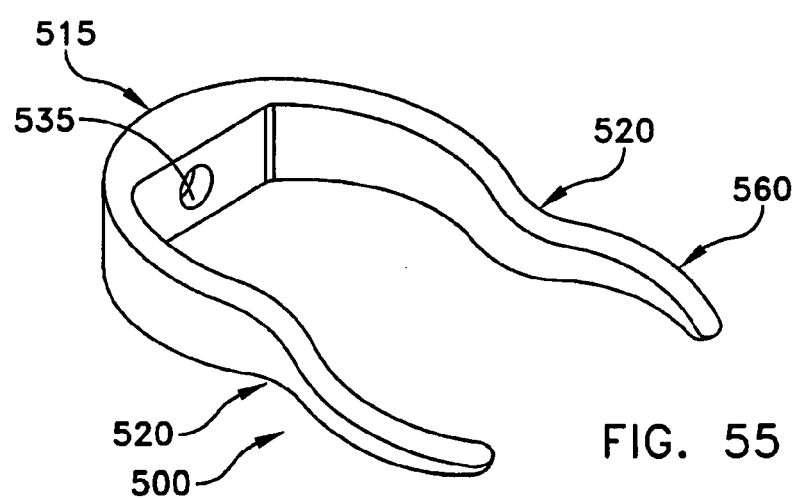
Figure 56:
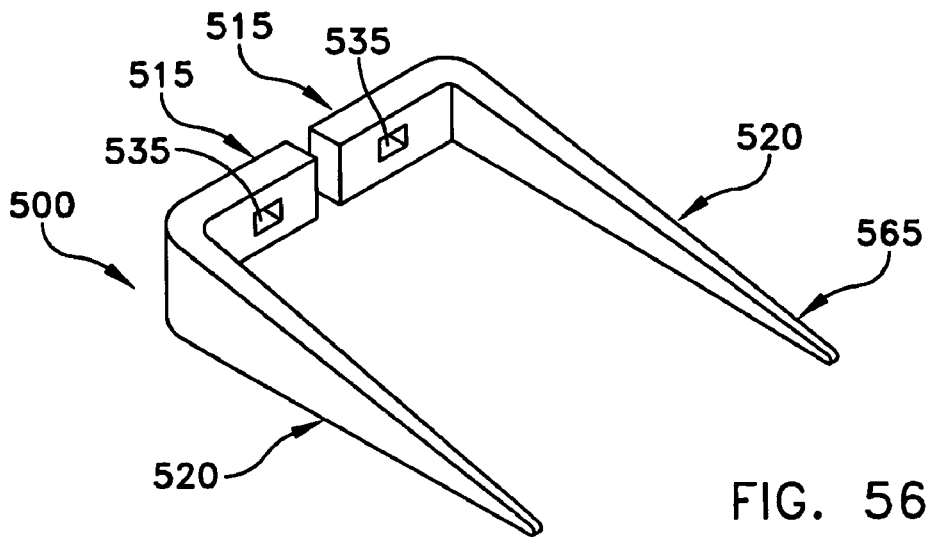
Figure 57:
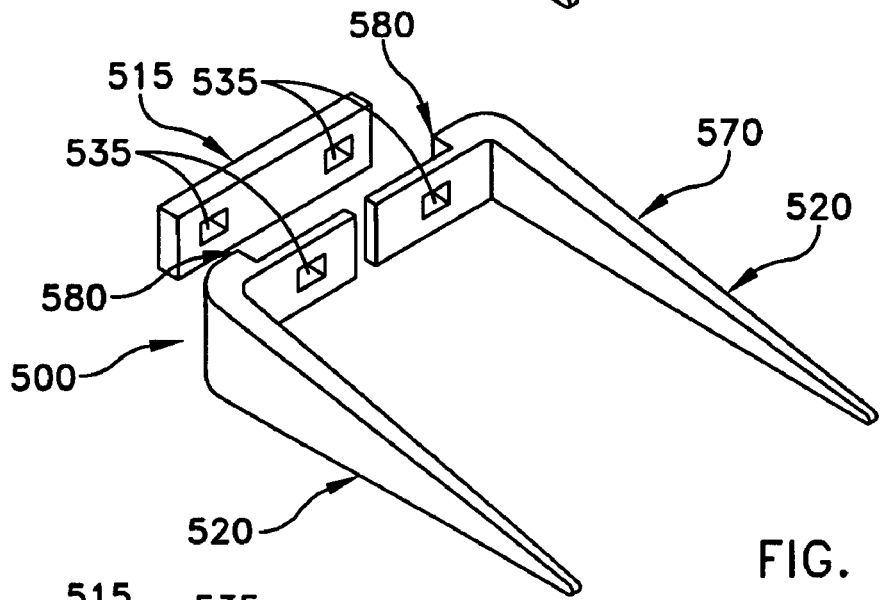
Figure 58:
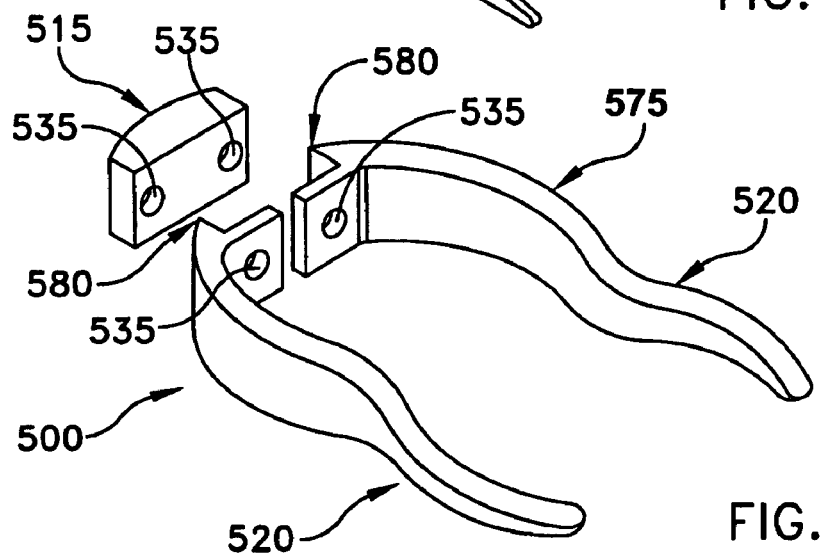
Figure 59:
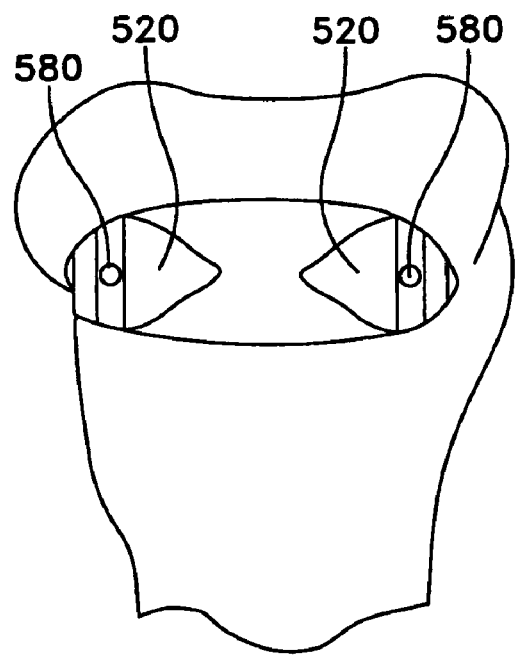
Figure 60:
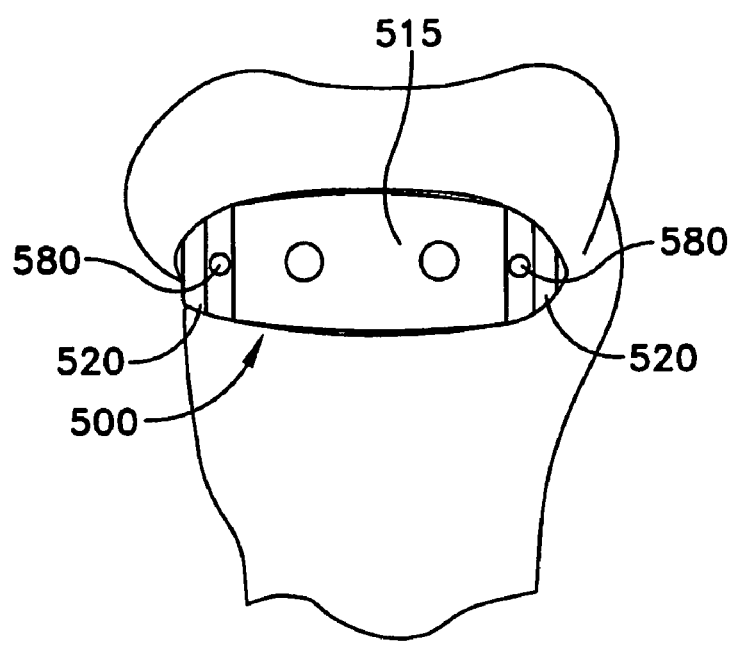
Figure 61:
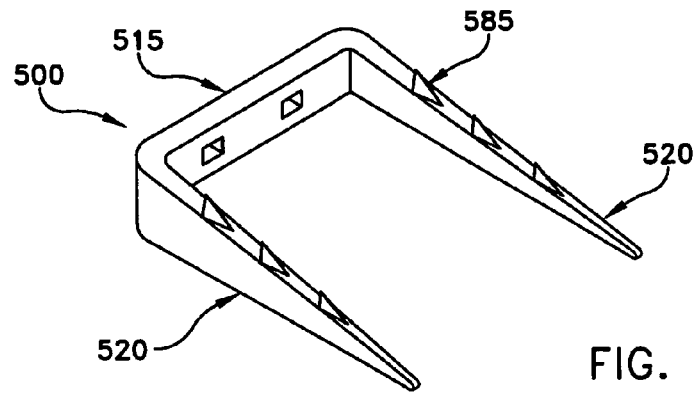
Figure 62:
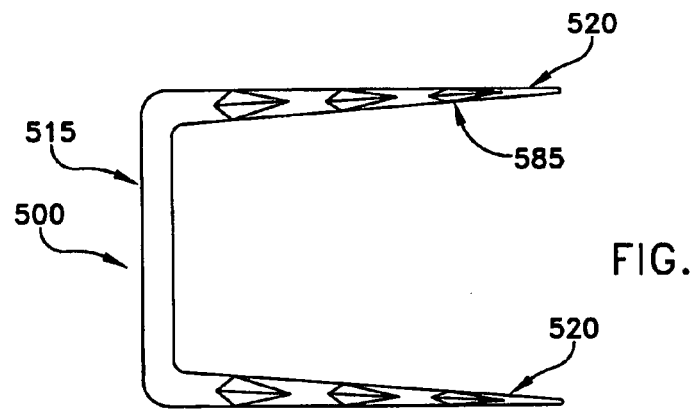
Figure 63:
Figure 64:
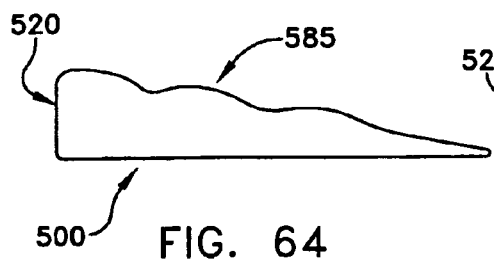
Figure 65:
Figure 66:
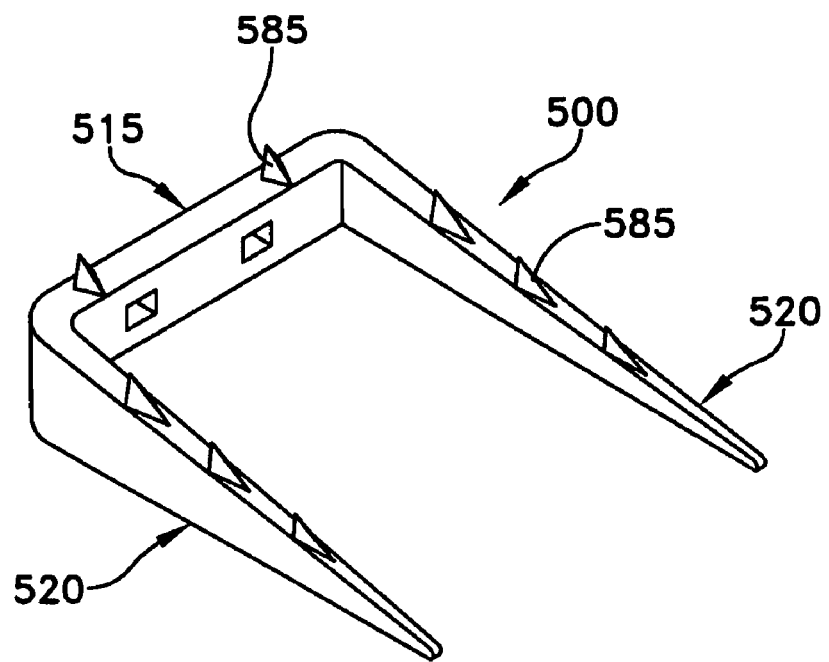
Figure 67:
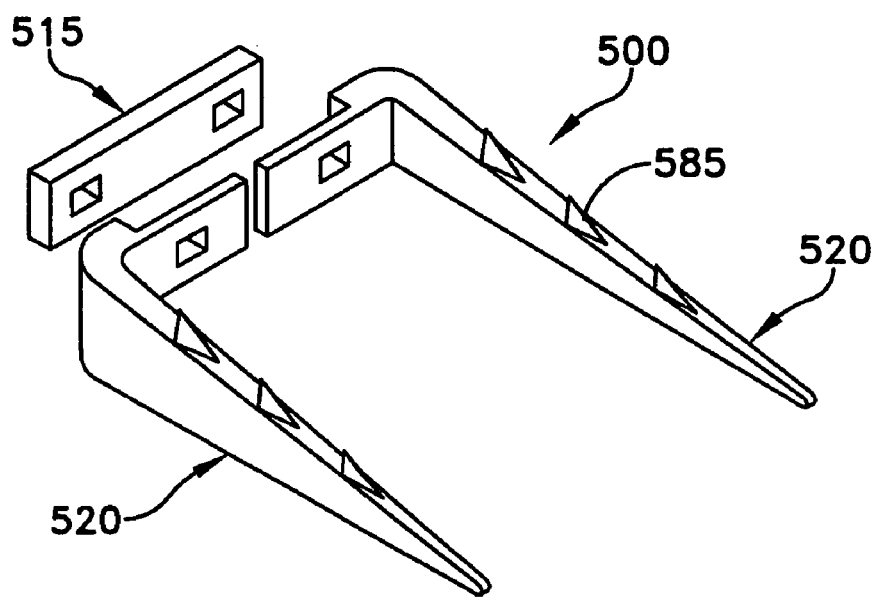

As with multi-part implant 125, the overall design of substitute implant 500 is wedge-shaped (FIG. 49), with a leading (or distal) edge 510 that fits into the closed (or distal) portion of the open wedge osteotomy, and a base (or proximal) side 515 that fits into the opening (or proximal side) of the open wedge osteotomy. Implant 500 comprises two opposing side walls 520 (FIG. 50), each preferably measuring about 2-5 mm wide, with their surfaces framing the perimeter of the bony void with an open inside perimeter 525, the leading side or edge 510, and the high base side 515. Base 515 preferably has a height of about 2-10 mm or greater. In a preferred embodiment of the present invention, base 515 has a slightly wider width than distal end 510, and base 515 is radiused at its outboard sides (FIG. 51). The length of implant 500 approximates the depth of the osteotomy, typically measuring about 40-70 mm. Implant 500 is configured so that, overall, it closely follows the perimeter of tibia 10 across the osteotomy void 110.

Figure 49:
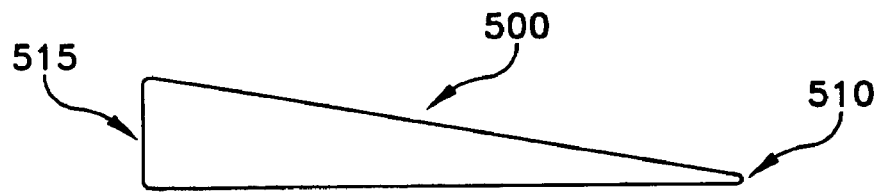

Implant 500 may utilize a variety of shapes and constructs in addition to those shown in FIGS. 49-51, as will be described below.

Referring next to FIG. 51, in a preferred embodiment of the present invention, implant 500 comprises a solid wedge frame implant 530. At the leading (or distal) end 510, the height of implant 500 decreases or tapers to conform to the closed portion of the tibial osteotomy. At base (or proximal end) 515, the implant is taller to conform with the larger, exposed opening of the wedge osteotomy. Implant 530 may be of the same or varying (e.g., widening) width as it extends from leading end 510 to base 515. Base 515 of implant 530 preferably includes one or more holes or openings 535 extending completely through base 515. Openings 535 allow material to be introduced into the interior of the implant, e.g. allograft or autograft bone, demineralized bone substitutes, other bone graft material preferably having osteoinductive or osteoconductive properties, bone cement, or other desired materials. Preferably, implant 530 has four continuous or joined sides including the base 515, the two sides 520, and a floor portion 540; the four components together define the open perimeter 525.

Referring now to FIGS. 52-55, there are shown single-piece wedge frames 545, 550, 555, and 560, respectively. These four frames are formed out of three (a base and two sides) continuous or joined portions, but do not have a leading (i.e., distal) edge, and have an open bottom (i.e., they omit the floor portion 540).

Referring now to FIGS. 56-60, in other preferred embodiments of the invention, there are provided multi-part wedge frames 565, 570 and 575, which comprise a base 515 and two opposing side walls 520. In the case of implant 565, base 515 may be formed in two halves, with one half connected to each side wall 520. In the case of the wedge frames 570 (FIG. 57) and 575 (FIG. 58), base 515 may comprise two halves, one connected to each side wall 530, and a connecting plate connecting the two base halves together. The various parts making up frames 565, 570 and 575 are preferably inserted separately into the osteotomy void 110 and, in the case of wedge frames 570 and 575, which include a connecting base member, secured together. Preferably, the insertion takes place posterior side first, then the anterior side and finally, in the case of frames 570 and 575, the connecting base last. Base 515 is preferably attached to sides 520 at 580, using screws, rods or any other fastening means, which are preferably of the same material as the implant.

A distinct advantage of the multi-part implant 565, 570, and/or 575, as well as the multi-part implant 125 described previously, is the ability to effect intended changes to the tibial slope by inserting one wall 520 of a specific height and size, and then inserting an opposing wall 520 of a potentially different height and size. These changes can be calculated preoperatively or may be a result of an intra-operative assessment by the surgeon.

Looking next at FIGS. 61-68, any of the aforementioned implants 500, as well as the aforementioned multi-part implant 125, can include projections, ridges or protrusions 585 (hereinafter sometimes collectively referred to herein as "projections 585") on its bone interface surfaces. These projections 585 are shaped in such a way as to allow for easy insertion of implant 500 into the osteotomy void 110 but prevent migration of implant 500 once fitted in place.

The various wedge shaped implants 500 may be formed out of a metal (e.g., titanium or stainless steel) or any other biocompatible material or polymer, absorbable or non-resorbable, that may or may not be osteoinductive or osteoconductive.

Figure 68:
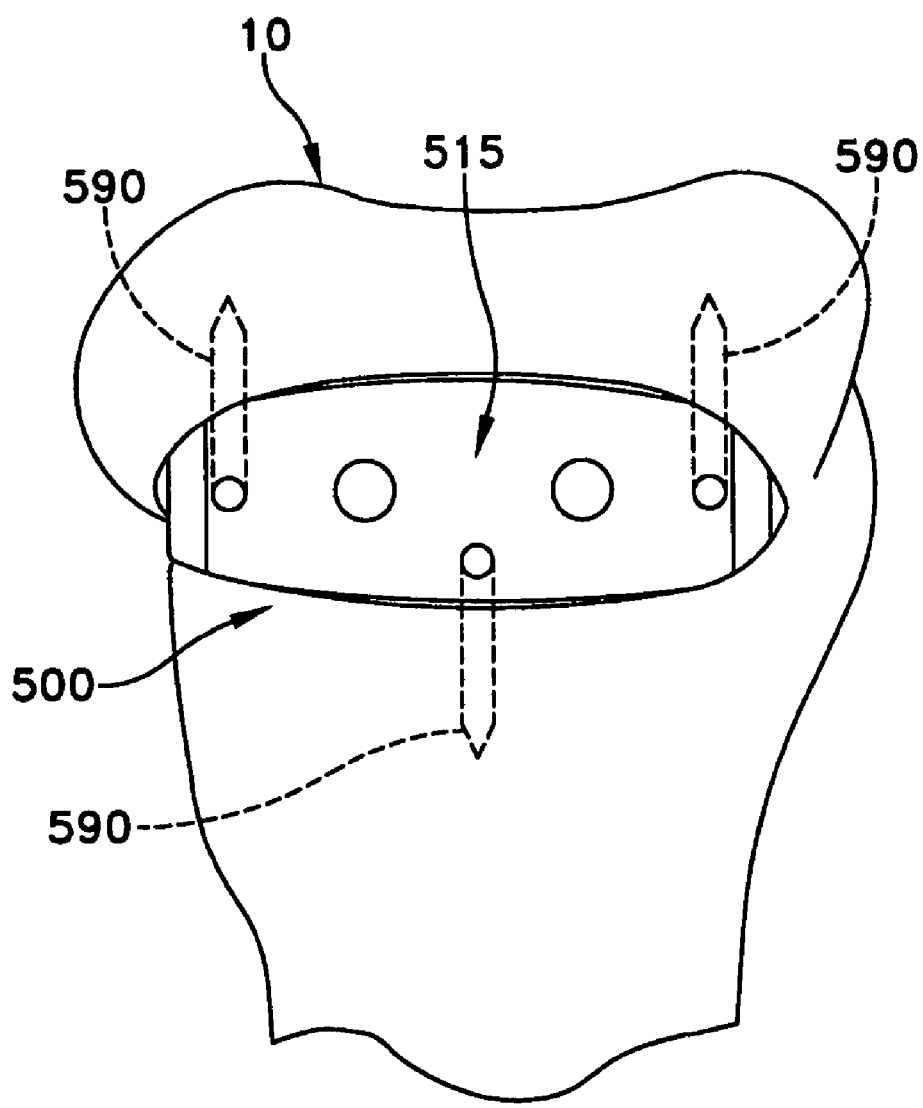
Figure 69:
Figure 70:
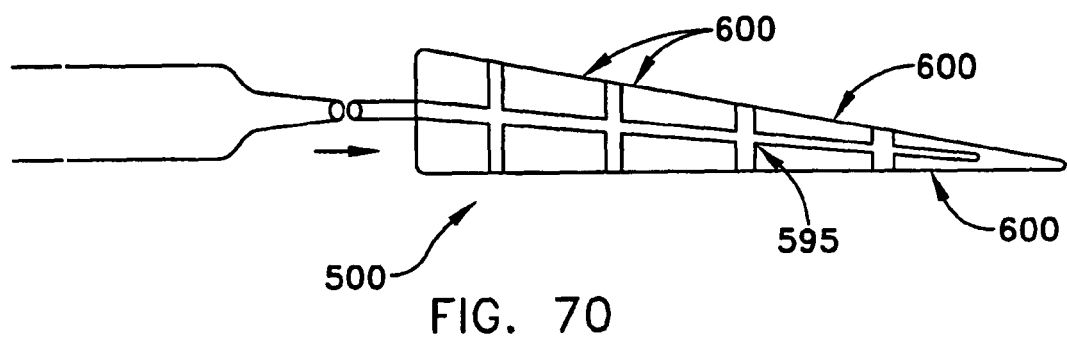
Figure 71:
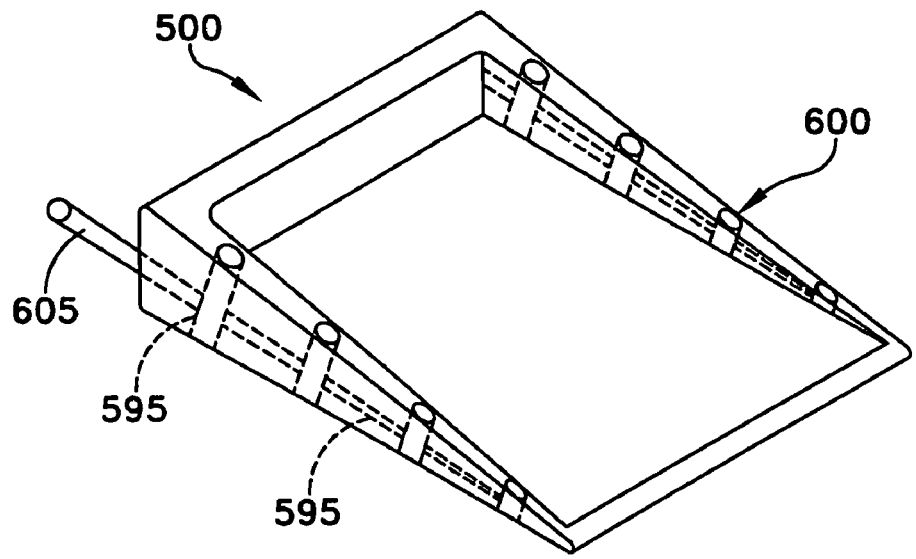
Figure 72:
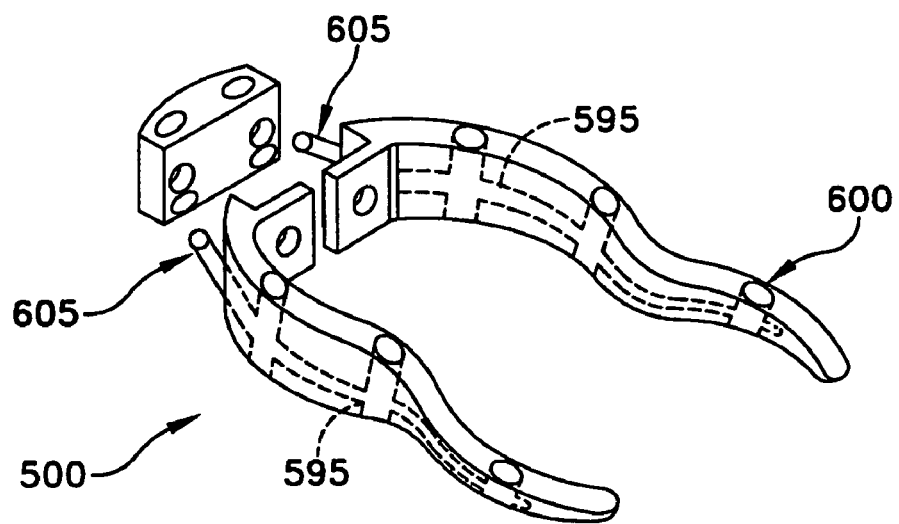
Figure 73:
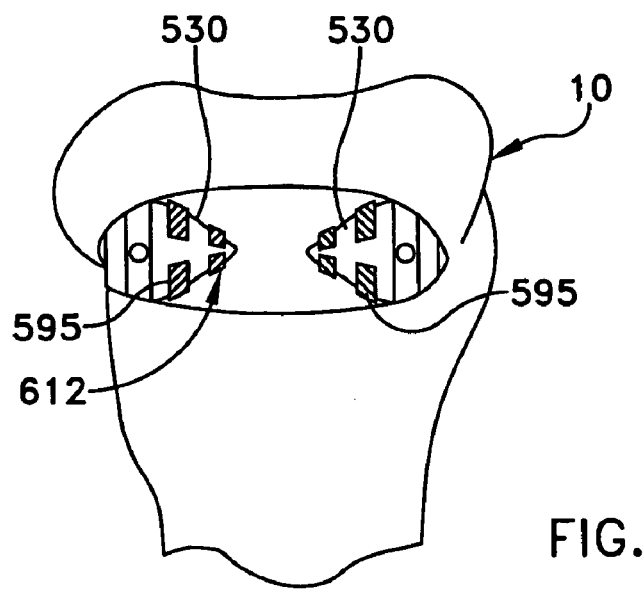
Figure 74:
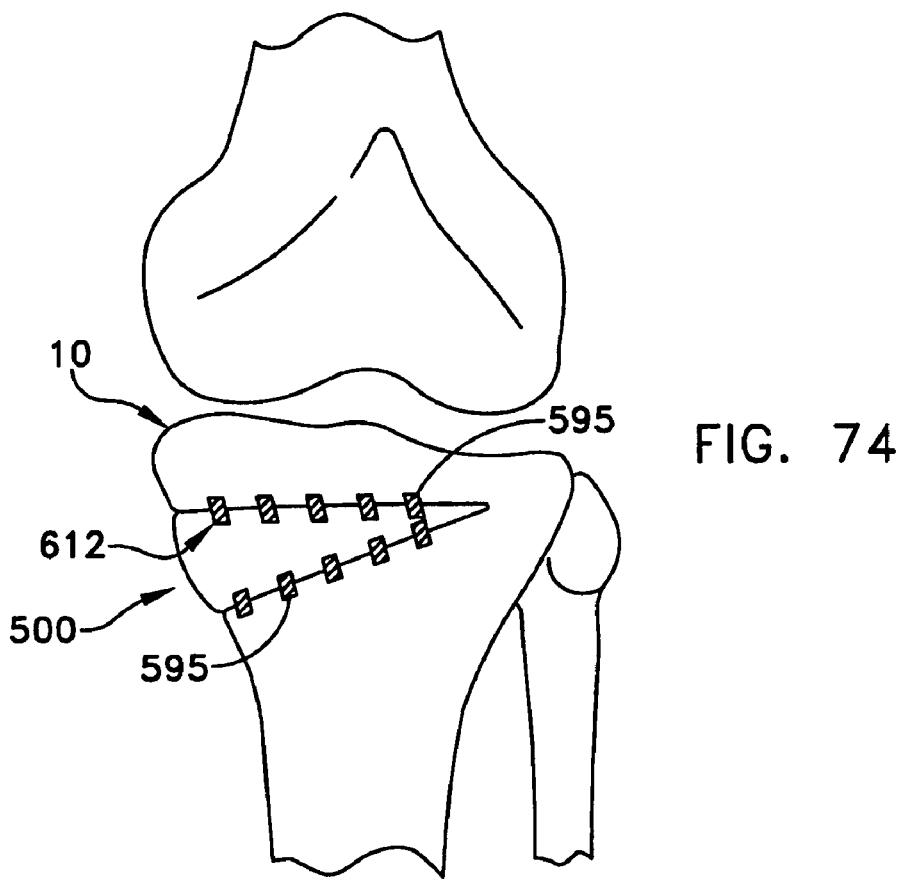
Figure 75:
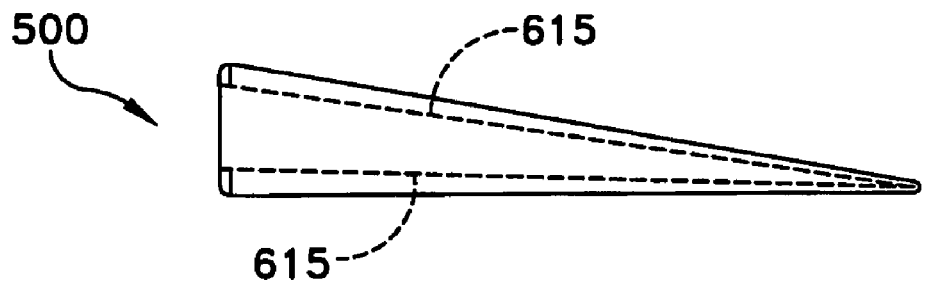
Figure 76:
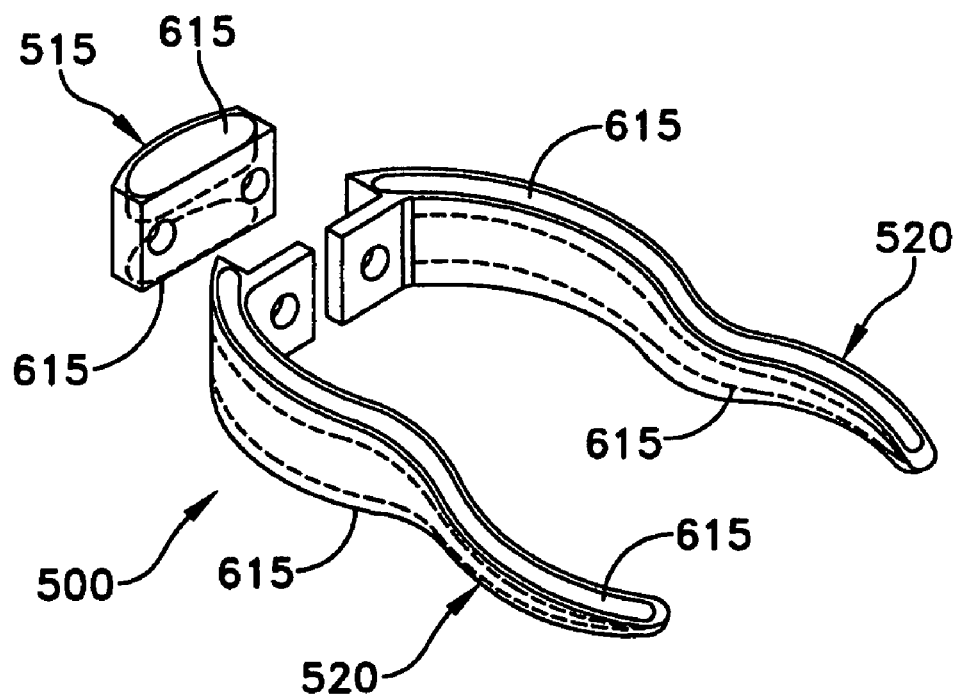

Looking next at FIG. 68, the base 515 of implant 500 can be further secured to tibia 10 with the placement of screws or rods 590, preferably angled through base 515 into tibia 10. Screw or rods 590 may be directed both superiorly and inferiorly into the tibia. Furthermore, base 515 of the implant can also function as a secure fixation system, thereby replacing the traditional static fixation plate and bone screws.

As noted above, base 515 can be made of a metal material, a bioabsorbable material, a biocomposite material that may or may not promote bony integration, or a combination of biocomposite materials and metal in order to add strength to the eventual loading of the osteotomy site. It may be preferable to provide a base member that provides sufficient weight-bearing support and strength through the natural healing period of the osteotomy site and then begin to resorb over time, thereby preventing or reducing the effects of stress shielding of the repair and new bone growth. Such a resorbable base member, in conjunction with a resorbable, solid walled implant, provides active compression across the osteotomy site, thereby promoting faster and stronger healing of the osteotomy site.

Looking now at FIGS. 69-74, in other preferred embodiments of the present invention, the wedge 500 may take various configurations which incorporate channels 595 extending through components for delivering biocompatible adhesive glues, bone cements, growth factors or grafting materials to the bone contacting surfaces 600. These materials are preferably resorbable. The provision of channels 595 in the implant is an important feature, since (i) it may permit the implant to be better secured within the osteotomy void 110 when glues or cement-like materials are delivered through channels 595, and (ii) it may facilitate formation of beneficial bony ingrowth when growth factors or grafting materials are delivered.

When adding nonresorbable cements or glues to secure the implant, it may be advantageous to allow natural cortical bone growth and new bone integration into and through the surfaces of the wedge implant; this may provide for better long-term security and stronger healing of the osteotomy site. As such, these adhesives and/or bone cement materials can be delivered through a narrow tube-like device 605 (FIG. 69) that incorporates openings 610 that align with channels 595 running to surface 600 of implant 500. Once adhesive or cement-like material 612 is delivered through tube device 605, into and through channels 595, to surface 600 of implant 500 and native bony surface of tibia 10, tube device 605 is withdrawn. Such a delivery approach provides for areas of adhesion while allowing native bony contact with surface 600 of implant 500. Also, by delivering material 612 through tube device 605, which may run the length of implant 500, and then withdrawing tube 605, more of implant 500 may integrate with new bone growth while using the an efficient amount of adhesive or cement material to secure implant 500.

Figure 77:
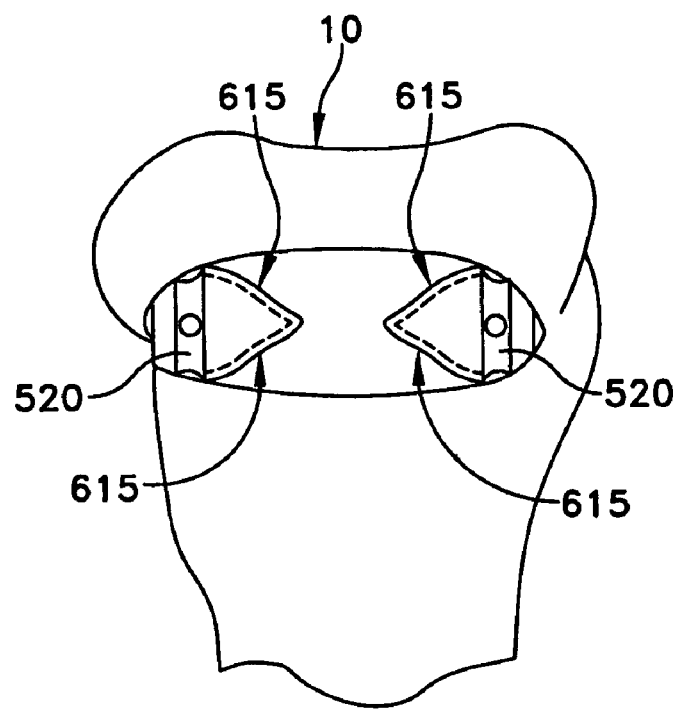
Figure 78:
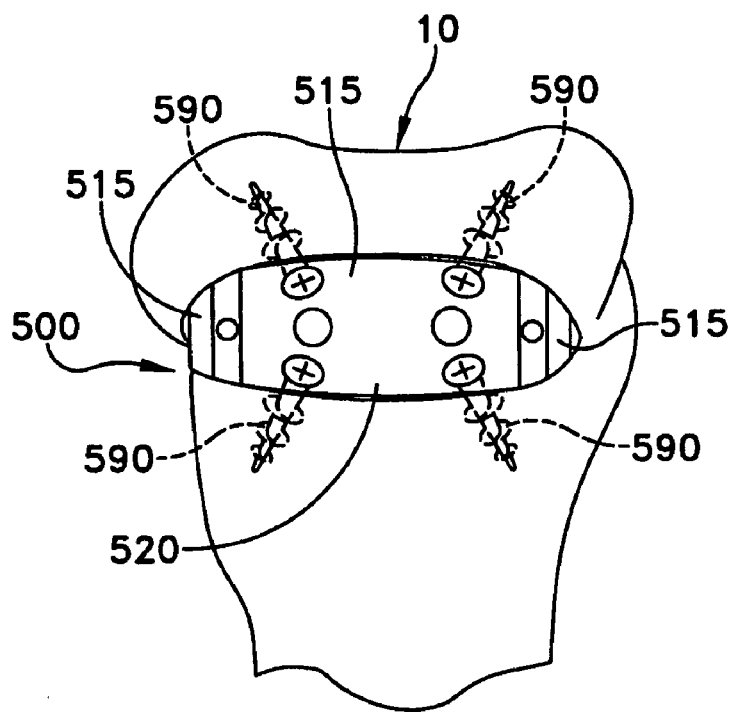
Figure 82:
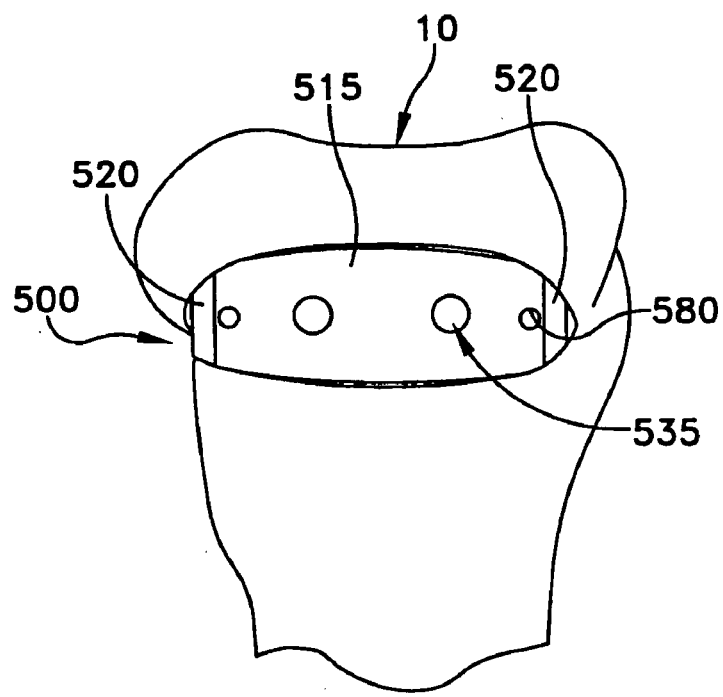

Referring now to FIGS. 75-78, in a preferred embodiment of the present invention, at least one implant/bone interface channel 615 is formed in implant 500. When using resorbable adhesives or bone cements, it may be advantageous to have material flow or be delivered within an open cavity that follows at least a substantial portion of the entire contact surface between implant 500 and bone 10 (FIG. 77). This configuration generally provides increased strength of fixation and improved attachment of implant 500 to bone 10. As such, after implant 500 is inserted and positioned, adhesive material is injected/delivered into implant/bone interface channel 615. Base 515 is preferably attached to tibia 10 with either screws 590 (FIG. 78) or with adhesive (not shown).

Three-Part Implant And Trial Procedure

Referring next to FIGS. 79-83, with the vertical height of actuator housing 360 fixed in place, the surgeon may insert a trial implant 500A for the posterior side and the anterior side of wedge frame implant 500 (FIG. 80). To this end, there are preferably provided a number of incrementally-sized trial stabilizers that the surgeon uses to attain the best anatomical fit for implant 500, and to ensure proper positioning for the attachment of the base 515 that fits into osteotomy opening 110.

Once the properly sized anterior side 520 and the properly sized posterior side 520 of implant 500 are inserted, actuator 350 is unlocked and rotated so as to slightly loosen corrective device 340 (FIG. 44). Actuator housing 360 is then removed from the corrective plates, and each plate is removed (FIG. 81). Bone graft and/or bone filler material can be introduced into the osteotomy, filling much of void 110. The appropriately sized base wall 515 of wedge implant 500 (FIG. 82) is fitted into wedge opening 110. Base 515 is then secured to side walls 520 through the use of the threaded fasteners 580. Additional bone graft material is then introduced through openings 535 in base 515 and the bony void is filled.

Figure 83:
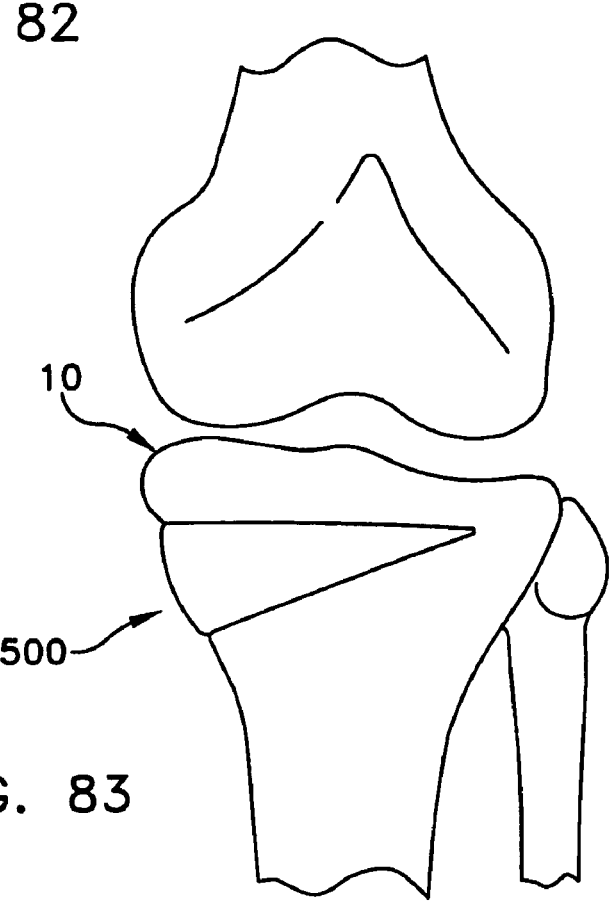
Figure 84:
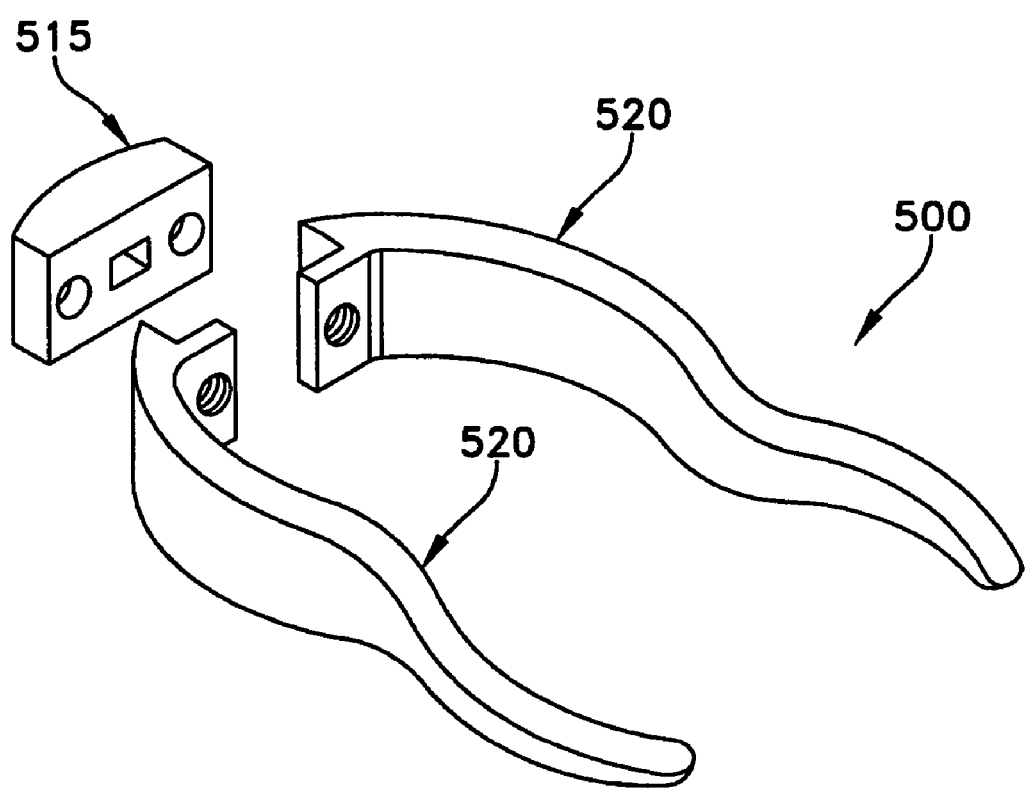
Figure 85:
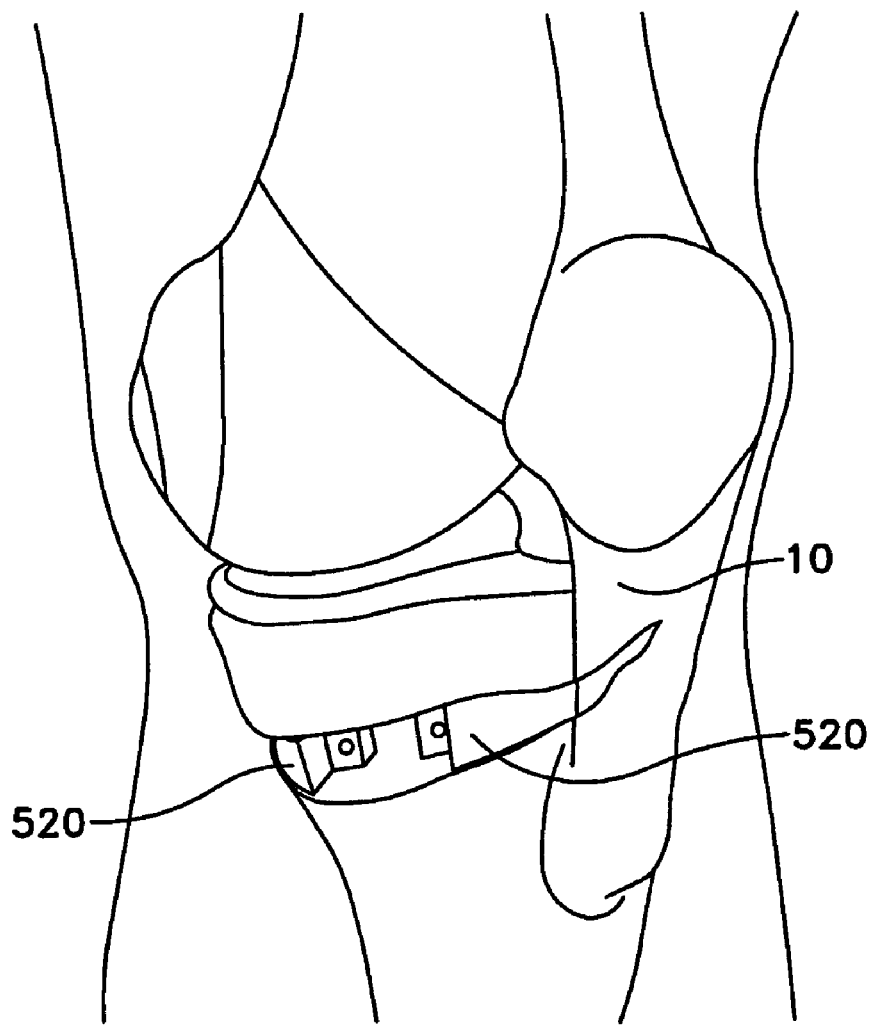
Figure 86:
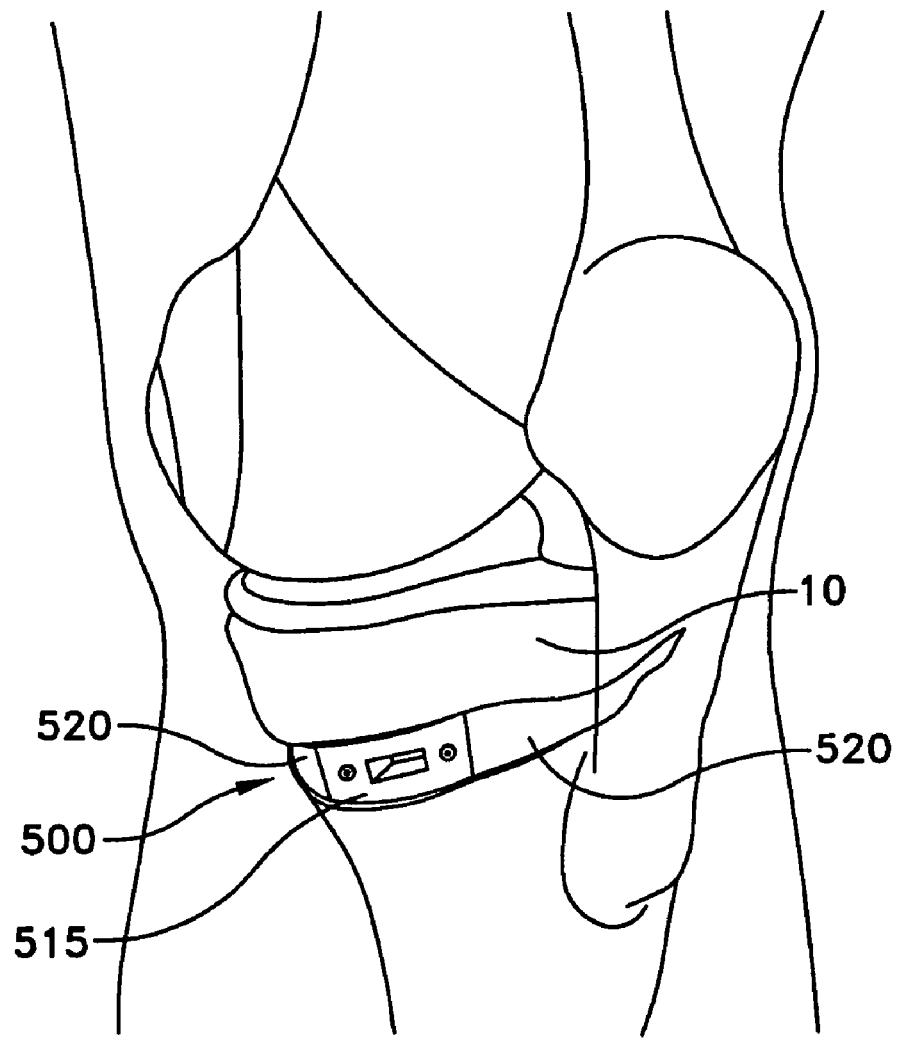
Figure 87:
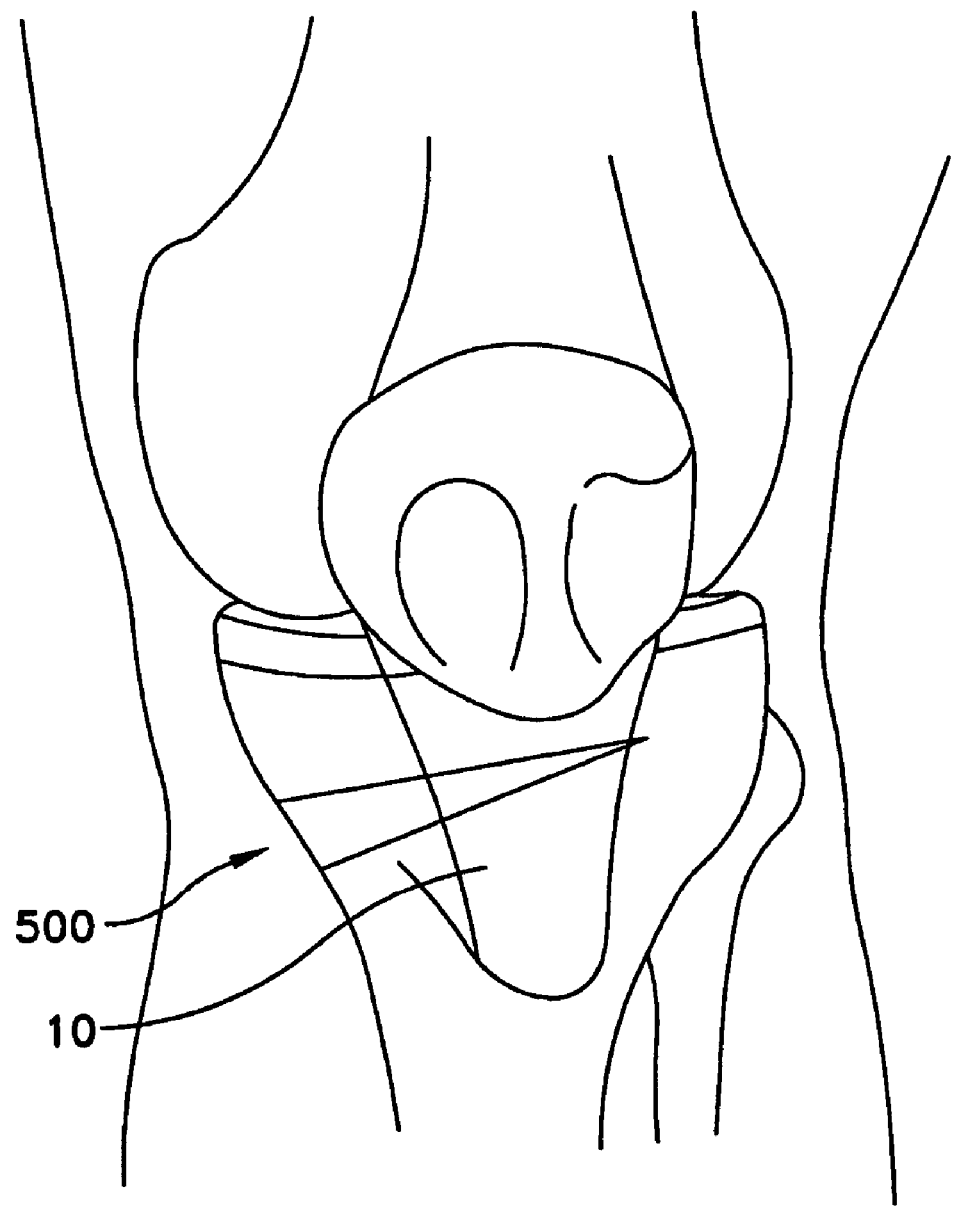

Referring now to FIG. 83, stabilization about the osteotomy site is achieved with the wedge-shaped implant 500 providing stability about the osteotomy site while maintaining the desired corrective angle. By allowing the direct contact of bone graft material with the bony cut surface of the osteotomy, within the perimeter of the wedge implant, the necessary physiologic compression and stimulation required to promote new tissue and bone growth through the bony void is provided.

FIGS. 84-87 show another depiction of the three-part wedge-shaped implant and the trial procedure described herein and illustrated in FIGS. 79-83.

One-Part Implant And Trial Procedure

Figure 88:
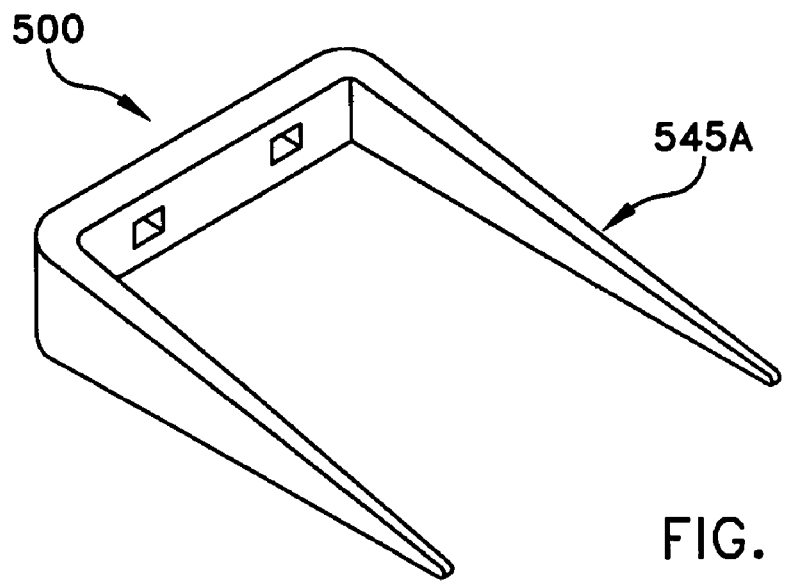
Figure 89:
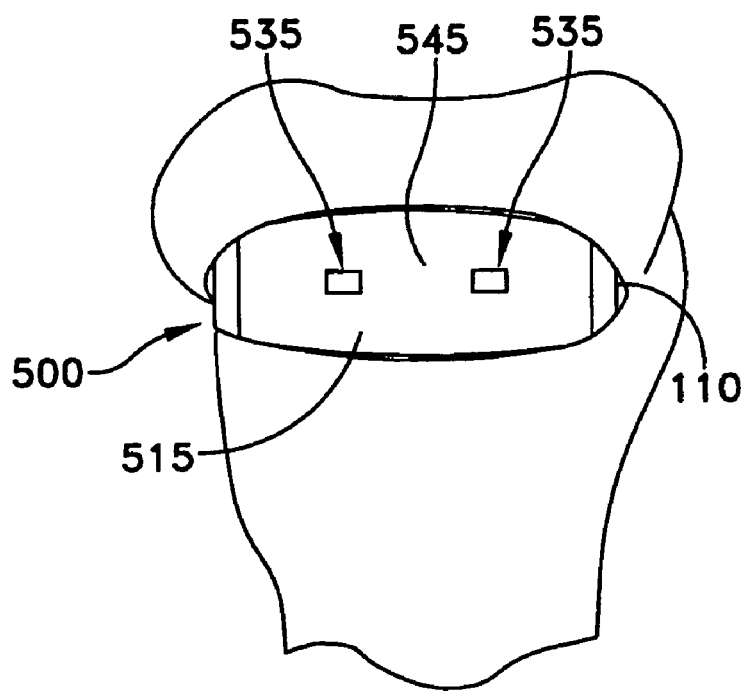

Referring now to FIGS. 88 and 89, there is shown a one-part, open-bottomed, wedge-shaped implant 545A. Again, the surgeon uses a trial implant 545A and inserts the trial implant 545A into osteotomy opening 110 to ascertain precise fit and sizing of trial implant 545A. Trial implant 545A is removed and the properly-sized implant 545 (FIG. 89) is inserted into the osteotomy void 110. The preferred bone graft material is introduced through the openings 535 of the base side 515 and the bony void is filled.

Again, stabilization is achieved with the wedge-shaped implant 545 providing stability about the osteotomy site while maintaining the corrective angle. By allowing the direct contact of bone graft material with the bony cut surface of the osteotomy, within the perimeter of the wedge implant, the necessary physiologic compression and stimulation required to promote new tissue and bone growth through the bony void 110 is provided.

Alternative Resection System 700 Comprising Two Blade Positioning Guide 705 And Resection Guide 710

Figure 110:
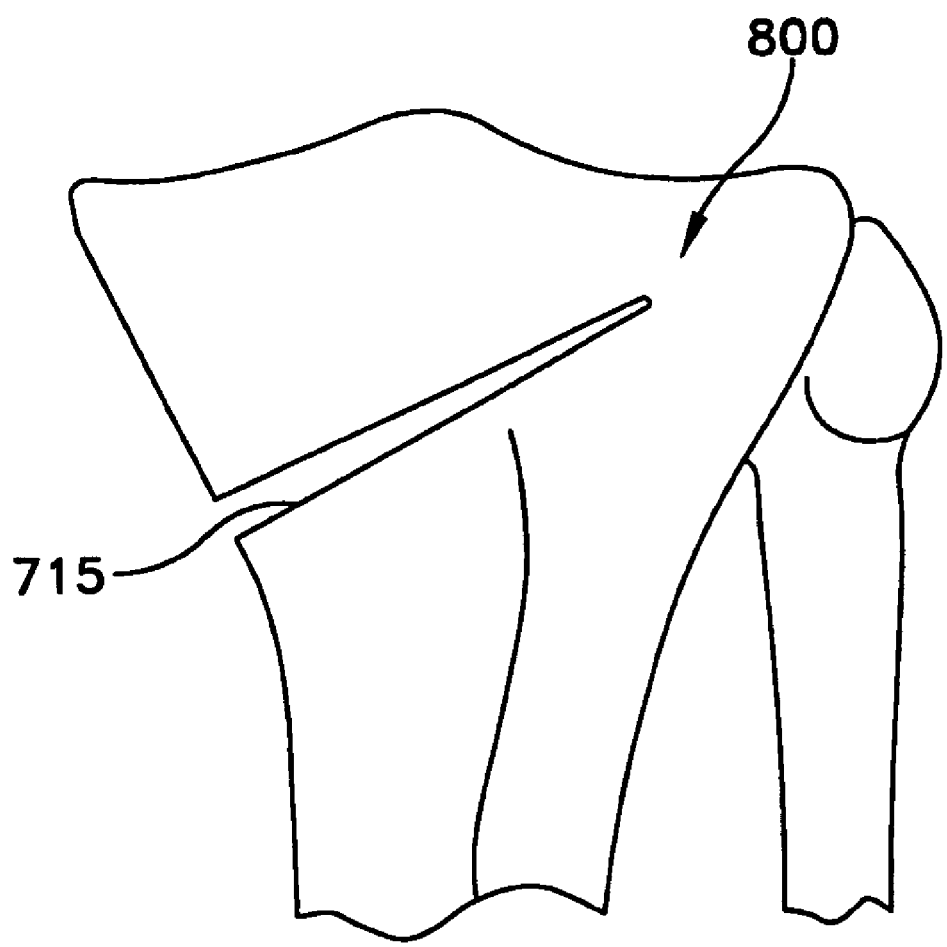
Figure 111:
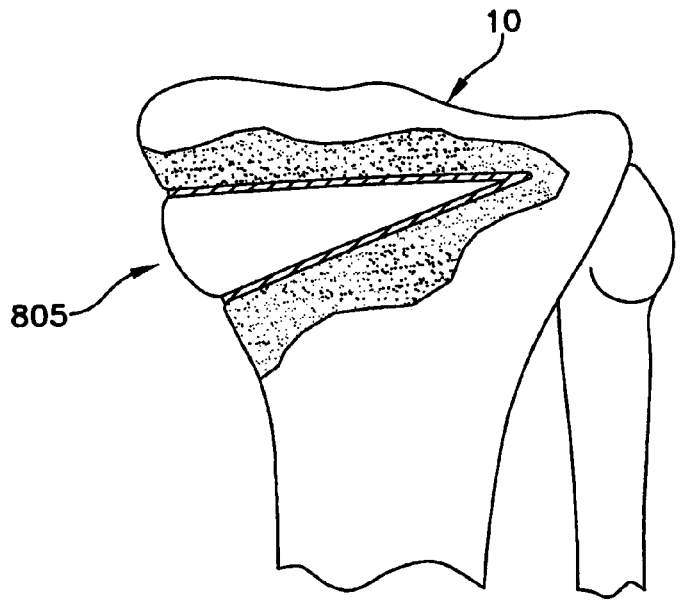

Referring next to FIGS. 90-109, in an alternative embodiment of the present invention, there is shown a resection system 700 comprising a two blade positioning guide 705 and a resection guide 710 for creating a bone cut 715 (FIG. 110).

Figure 90:
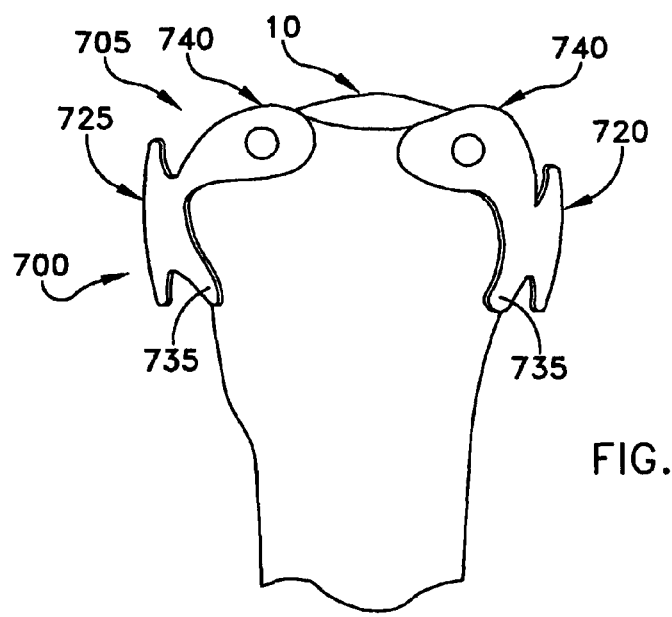
Figures 91, 92:
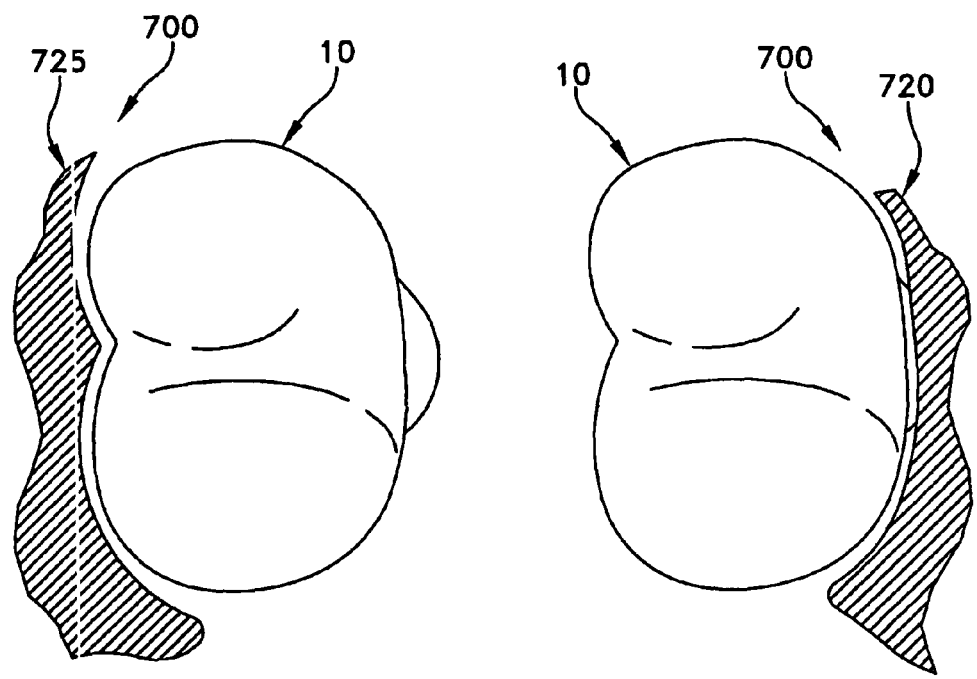

The osteotomy positioning guide 705 comprises two opposing blades 720, 725 (FIG. 90).

Figure 93:
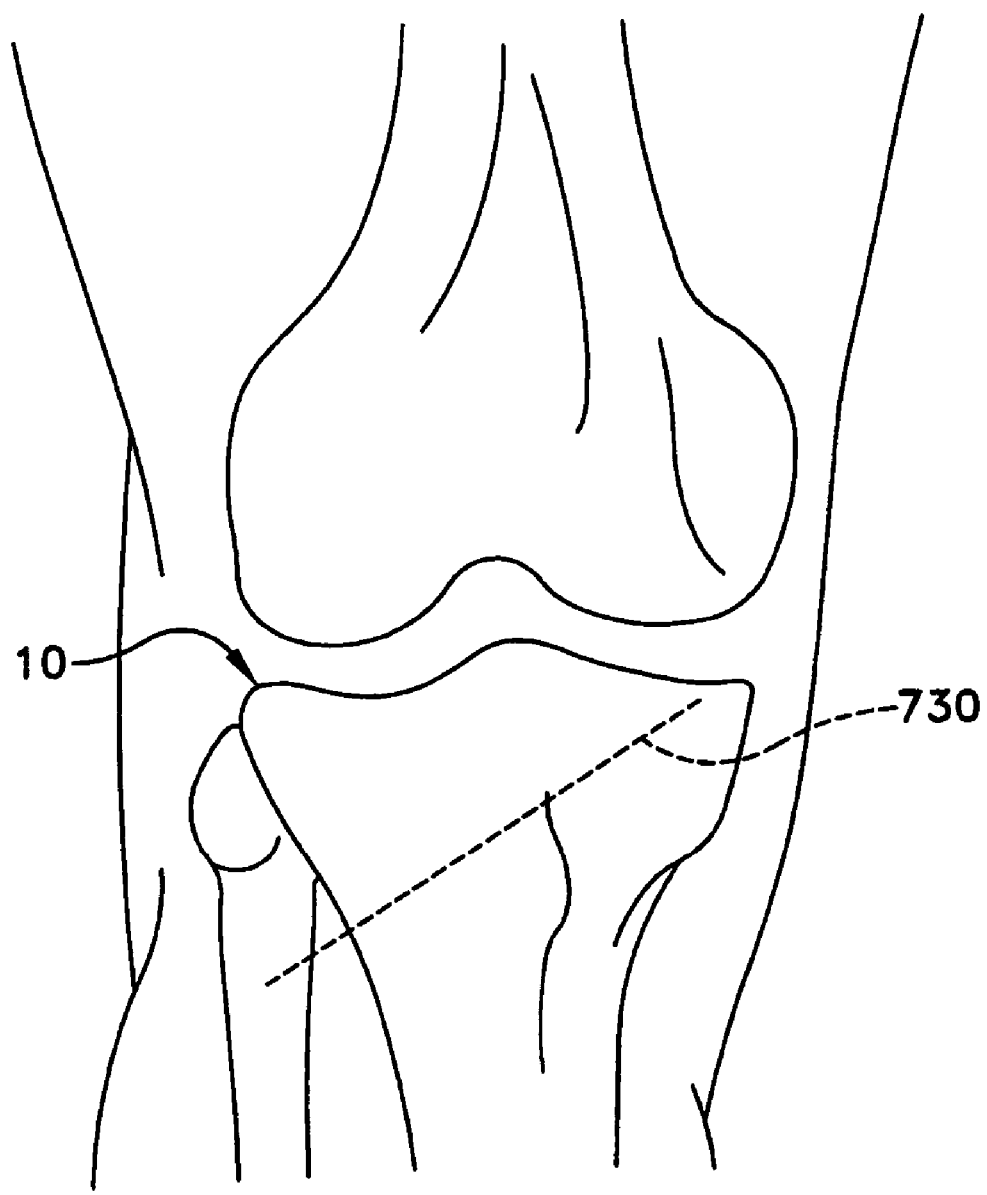
Figures 94, 95:
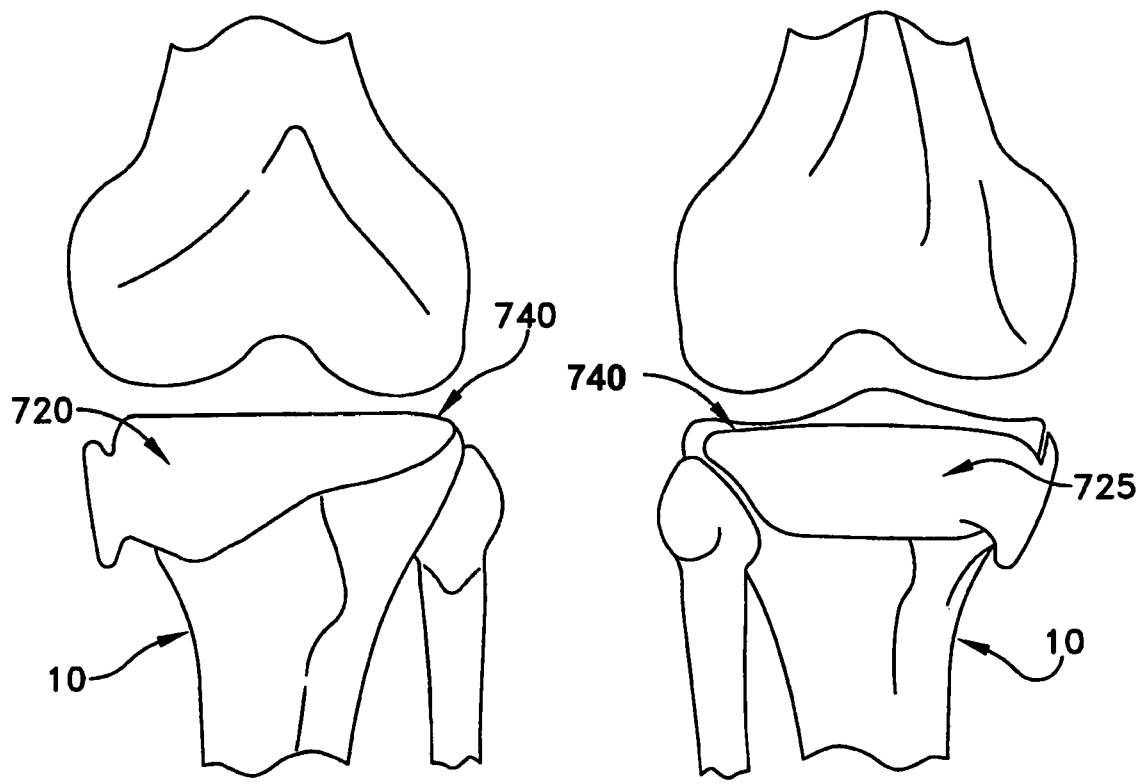
Figure 96:
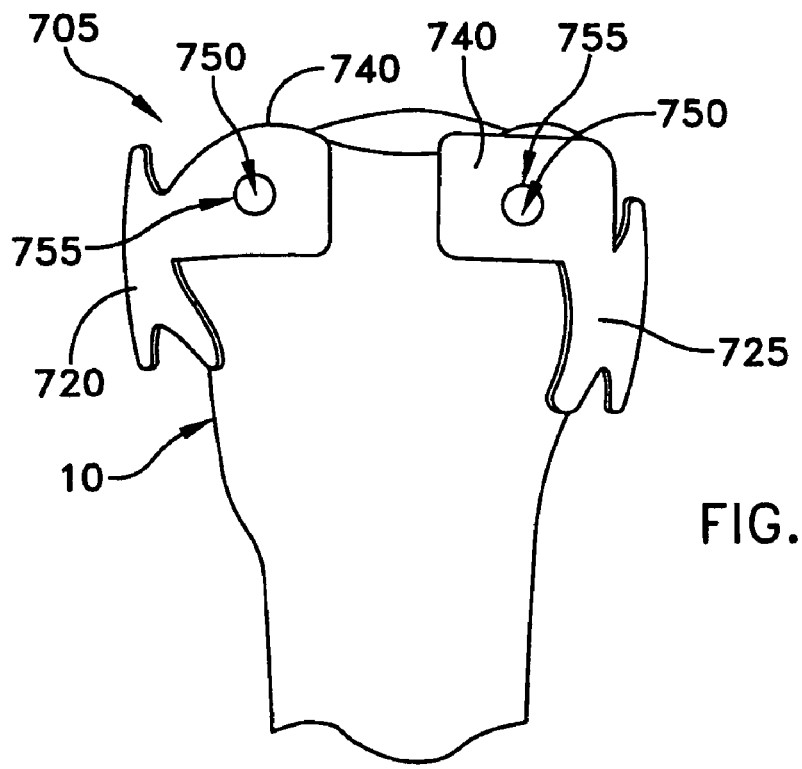
Figure 97:
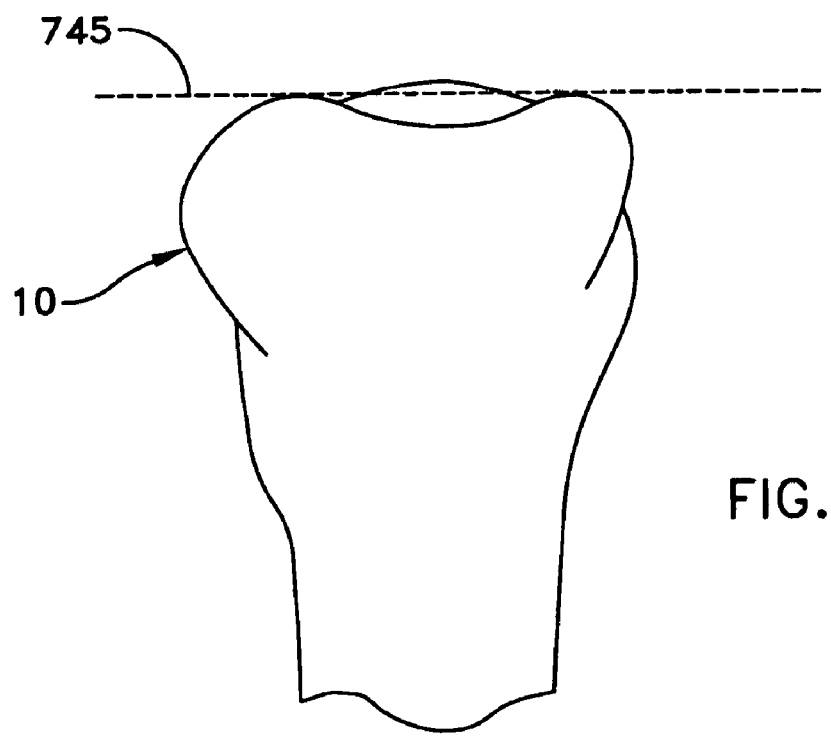

A posterior blade 720 (FIG. 91) is configured for the posterior aspect of the proximal tibia 10, and an anterior blade 725 (FIG. 92) is configured for the anterior aspect of the proximal tibia 10. Each blade member 720, 725 has a corresponding radius of curvature that allows it to fit closely to the surface of tibia 10 (FIGS. 91 and 92) into which the transverse resection 730 is to be performed (FIG. 93). Each blade member 720, 725 is preferably wide enough to protect soft tissue and neurovasculature structures during the osteotomy procedure. Each blade member 720, 725 preferably has a small handle 735 (FIG. 90) integral with the member itself. Handle 735 allows easier deployment and positioning of each blade member 720, 725 around the proposed osteotomy site. The blade members 720, 725 can vary in length, width and thickness but, generally, will measure approximately 6-8 cm in length, 3-5 cm in width and 1-3 mm in thickness. Each individual blade 720, 725 is inserted through the incision site and guided around tibia 10. Superior margins 740 of each opposing blade 720, 725 can be adjusted in order to align blades 720, 725 with the anterior-posterior slope 745 of the tibia (FIG. 97). Once each blade member 720, 725 is properly positioned, the blade is secured in place using fixation holes 750 (FIG. 96) and fixation screws or pins 755. Fixation hole 750 on each blade member 720, 725 is preferably located about 1-3 cm below superior margin 740. However, each matching set of blade members 720, 725 preferably has equal distances from superior margin 740 to fixation hole 750.

Osteotomy guide 705 is preferably radiolucent, so as to allow the surgeon to take radiographs or use fluoroscopy with blade members 720, 725 in place.

In one embodiment of the present invention (not shown), osteotomy positioning guide members 720, 725 are expandable once placed through an incision.

Resection guide 710 is shown in more detail in FIGS. 98-103. Resection guide 710 comprises at least one oblique cutting slot 760, and is configured for attachment onto the fixation screws or pins 755 of blade members 720, 725.

When bone resection guide 710 is attached to tibia 10 using fixation screws 755, cutting slot 760 is properly located relative to the anterior-posterior slope 765 of tibia 10 (FIG. 100). Desired changes in slope 765 are preferably introduced by removing and re-positioning one or both of the screws 755 holding blade members 720, 725 and resection guide 110 to the tibia. Resection guide 710 has a corresponding radius of curvature for its body that allows a close fit to a bone surface 770 (FIG. 101). Preferably, the thickness or distance from bone surface 770 to the opposing side of resection guide 710 is such that a resecting instrument 775 (such as a bone saw cutting blade 775) cuts uniformly across tibia 10 at the same cutting depth. Preferably, there is provided a system of sized resection guides 710 with cutting slots 760 that correlate to the resection point of entry on the medial side of the knee (distance 285 below the joint line, as obtained from a preoperative radiograph, see FIG. 36) and to the planned oblique angle 290 of the resection (see FIG. 36) in order for resecting instrument 775 (FIG. 101) to remain superior to anterior tibial tubercle 270 (see FIG. 36). These resecting guides 710 preferably range in overall size from about 2-5 cm across tibia 10 (from anterior to posterior), about 3-5 cm in length and about 5-10 mm in thickness. Cutting slot 760 is preferably located about 3-5 cm below the joint line (FIG. 103), with an oblique cutting angle 290 of 20-60 degrees (FIG. 102).

Osteotomy Procedure Using Alternative Resection System 700 (Two Blade Positioning Guide 705 And Resection Guide 710)

A routine knee arthroscopy is generally carried out to remove any loose bodies and to perform general joint debridement. During the arthroscopy, other repair procedures may be carried out such as meniscus repair, cartilage repair or tissue regeneration procedures. Following the arthroscopy, an antero-medial skin incision is made over the tibia 3-5 cm below the joint line from the anterior tibial tubercle to the postero-medial border of the tibia.

Figure 104:
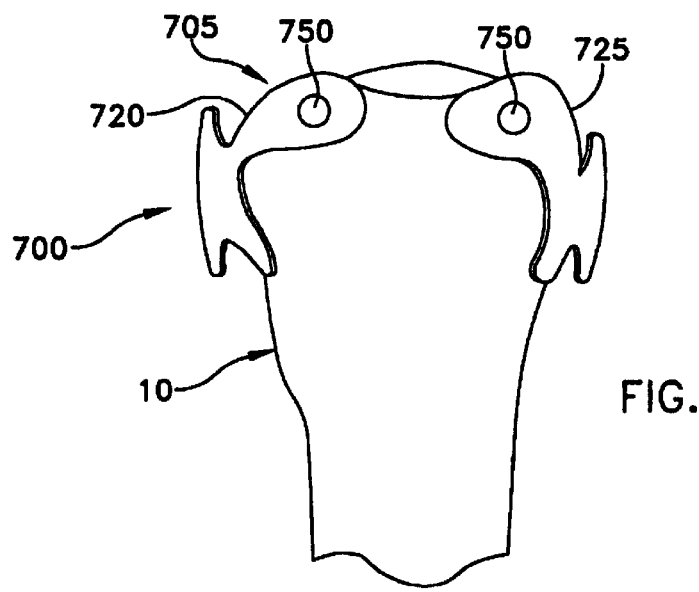
Figures 105, 106:
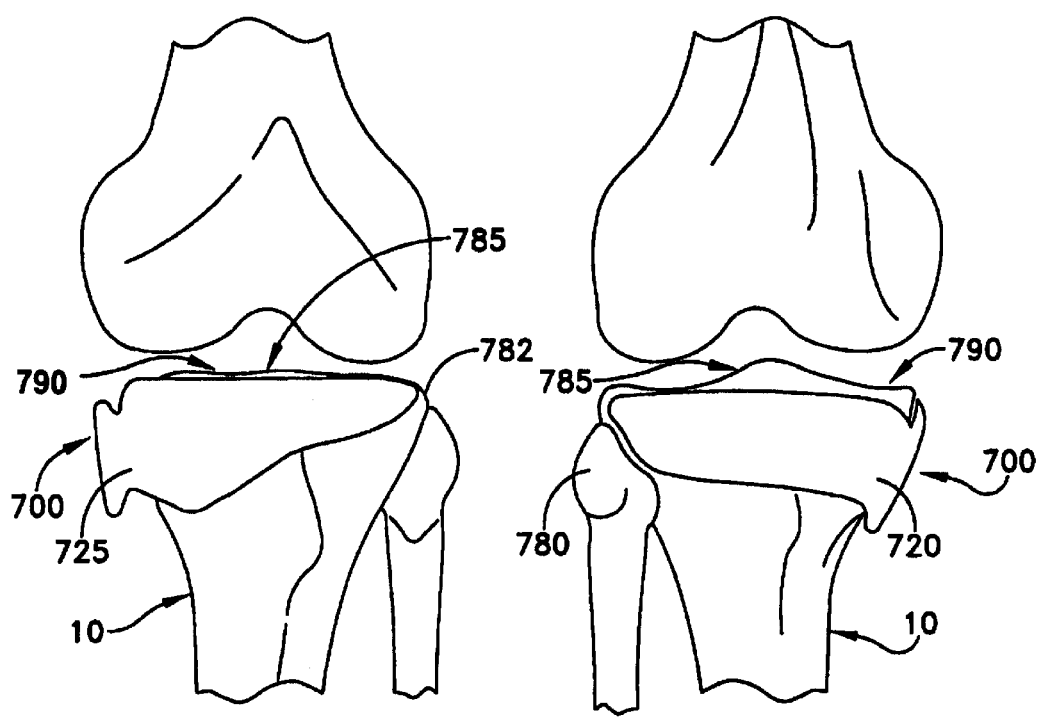

Referring now to FIGS. 104-110, a kit including resection system 700 is preferably opened at the surgical site. System 700 comprises the blade members 720, 725 and the section guide 710 that provide for a precise slope or plane of bone cut 715 (FIG. 110), and the protection of surrounding neurovasculature structures during the cutting operation. The two opposing blade members 720, 725 include the posterior blade 720 and the anterior blade 725, which are inserted through the incision site and guided around the bone 10 targeted for the osteotomy (FIG. 104). The pes anserinus is retracted, allowing visualization of the superficial medial collateral ligament (MCL). The MCL is retracted superiorly to allow the insertion of posterior blade member 720 below the medial collateral ligament and around the postero-medial border, hugging the posterior aspect of the knee. Posterior blade 720 reaches laterally to the medial border of the fibula and rests against fibular head 780 (FIG. 105). Anterior blade member 725 is inserted under the patella tendon and reaches to antero-lateral border 782 of the tibia 10 (FIG. 106). Each blade member 720, 725 has a corresponding radius of curvature that allows it to fit closely to the bone surface into which the osteotomy will be cut. These blade members 720, 725 can vary in length, width and thickness but, generally, will measure approximately 5-8 cm in length, 3-5 cm in width and 1-3 mm in thickness. Superior margins 740 of each opposing blade 720, 725 are aligned along tibial plateau 785 to follow the natural anterior-posterior slope or plane of the plateau. However, the surgeon can also adjust the position of either blade 720, 725 to affect a specific desired tibial slope change. The joint line can further be identified with the placement of Keith needles at region 790 (FIGS. 105 and 106) through the knee capsule and under the meniscus. This use of Keith needles aids the surgeon in properly aligning each blade member along the joint line. Each blade member 720, 725 is secured in place through its respective fixation hole 750 with the provided fixation screw or pin 755.

Figure 107:
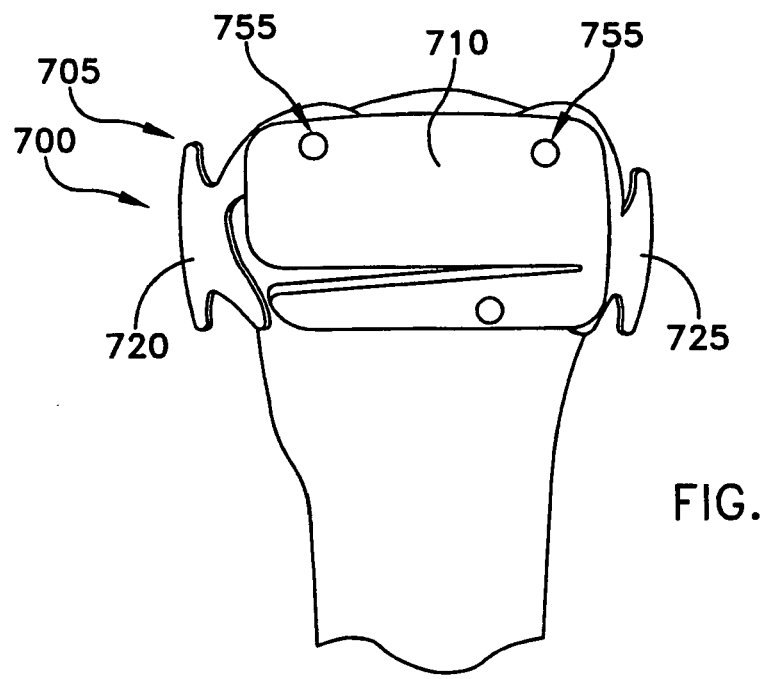
Figure 108:
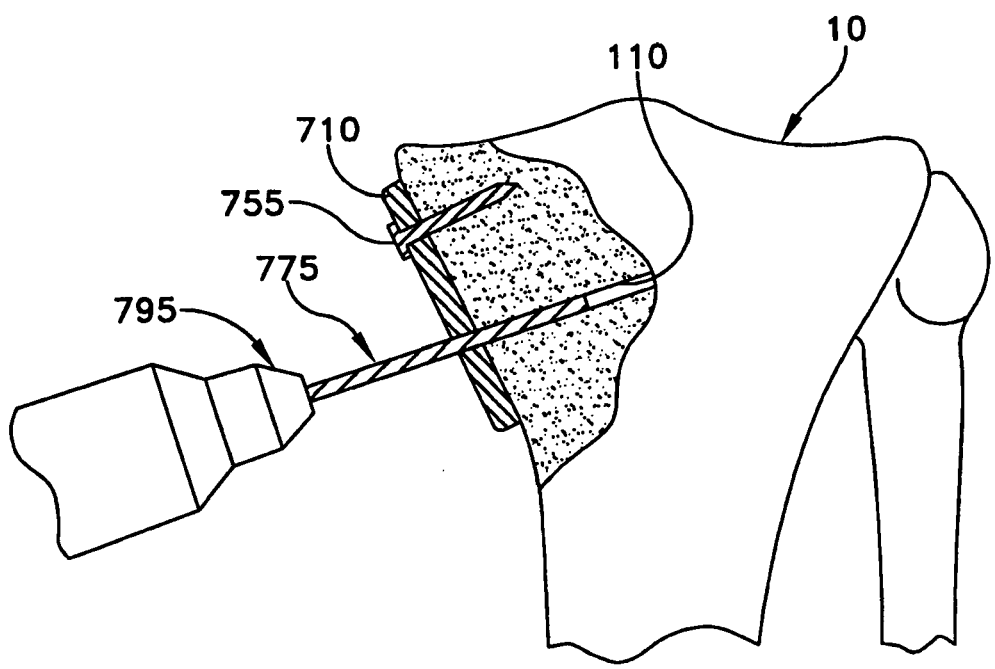
Figure 109:
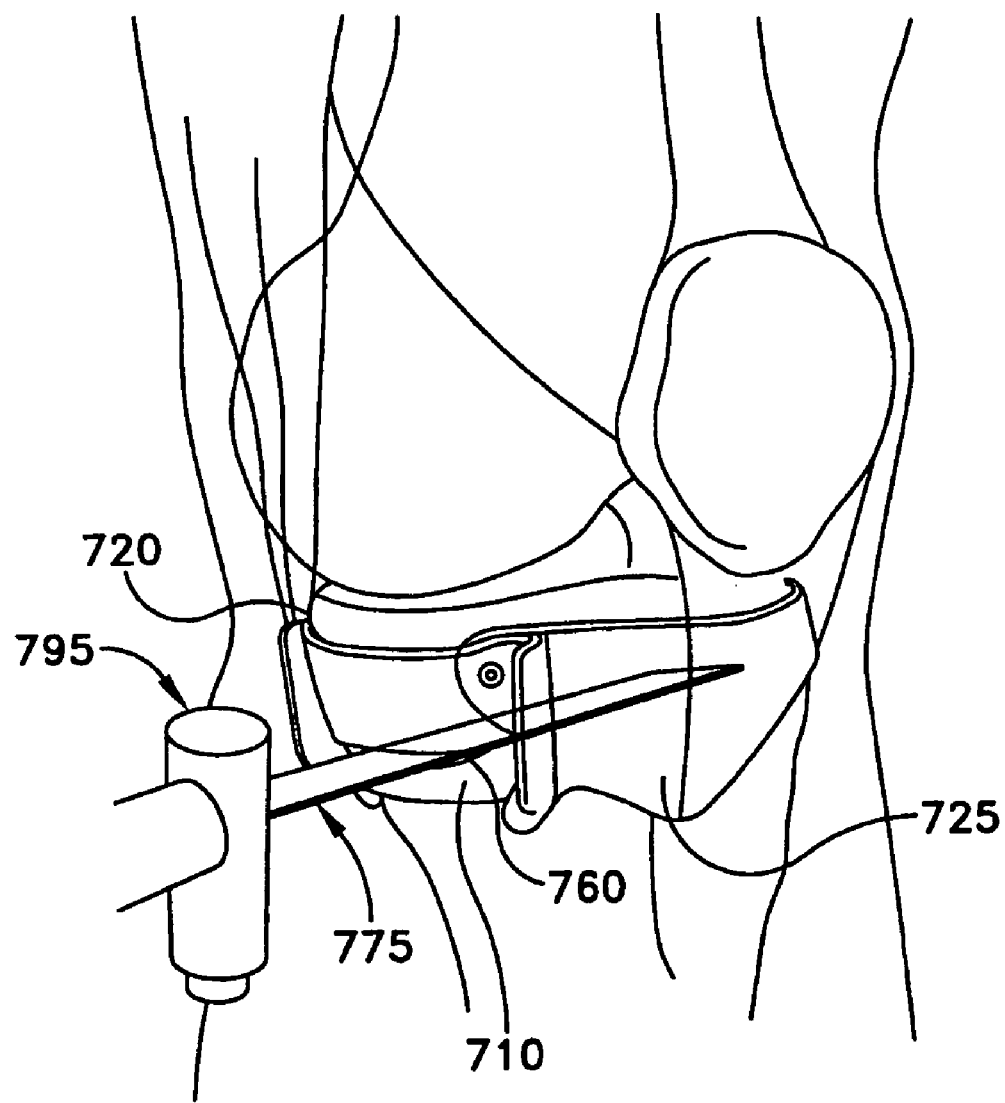

Next, a proper slotted cutting guide 710 is chosen. Preferably, there is provided a system of cutting guides 710 that correspond to overall sizing (i.e. small tibia, medium tibia, or large tibia) with each cutting guide body having a radius of curvature that allows it to fit closely to the bone surface. Based upon the preoperative planning procedure, the surgeon chooses the appropriately sized cutting guide 710, matching the preoperatively measured distance 285 below the joint line for the point of entry (FIG. 103) with the oblique cutting angle required to remain above tibial tubercle 270 (FIG. 36). The surgeon attaches or connects cutting guide 710 to the fixation screws or pins 755 of blade members 720, 725 (FIG. 107). The exact placement of bone cut 715 (FIG. 110) is precisely defined, incorporating the planned plane or anterior-posterior slope of the cut. Cutting guide 710 is preferably configured with a thickness or distance from the bone surface to the opposing side such that cutting blade 775 cuts uniformly across tibia 10 at the same cutting depth. The surgeon fits a blade stop 795 (FIG. 109) onto cutting saw blade 775 to mark the required distance of cut 715 as determined preoperatively. With protection of neurovasculature structures provided by blade members 720, 725, with the appropriate cutting guide 710 attached, and the appropriate cutting distance measured and ensured via blade stop 790, the cutting operation can be safely performed through slot 760 of the cutting guide 710 (FIGS. 108 and 109), effectively completing the osteotomy or bone cut through the bone cortices, leaving a minimum 1 cm bone hinge 800 on the lateral aspect of the proximal tibia 10 (FIG. 110). The slotted cutting guide 710 is then removed, leaving the positioning guide blade members in place.

Preferably, and following the formation of the osteotomy cut via a bone saw, the surgeon ensures that the bone cortices are cut by using a thin osteotome and probing the cortices inside the bone cut. Once assured that the bone cortices are cut, the surgeon removes the blade members 720, 725. Next, bone cut 715 (FIG. 110) is opened using an opening wedge device such as the mechanical jack 90 (FIGS. 13-15) or the alternative mechanical jack 300 (FIGS. 44-47). The wedge is opened until the desired angle is achieved. At this point the surgeon preferably slowly opens the wedge another 2 mm or so to allow for easier insertion of the wedge frame implant.

With the desired corrective angle achieved, the surgeon then prepares to stabilize and secure the open wedge osteotomy and insert bone graft material into the osteotomy void. This may be done using an appropriately sized implant such as the multipart implant 125 (FIGS. 19 and 20) or an alternative wedge osteotomy implant 500 (FIGS. 48-60, 61-68, 69-74, 75-78, 79-87 and 88-89) disclosed above. Each implant is sized according to the opening height of the wedge osteotomy and the depth of the cut. From the preoperative planning exercise, the surgeon most often has determined the correct implant size. However, the surgeon may also elect to use an implant trial to determine correct implant size as well.

Expandable Wedge Implant 805

Referring now to FIGS. 111-125, in another preferred embodiment of the present invention, there is shown an expandable wedge implant 805 comprising two opposing sides 810 which are coupled with an opening device such as the mechanical jack 90 (FIGS. 13-15) or alternative mechanical jack 300 (FIGS. 44-47) to create an open wedge osteotomy.

Figure 112:
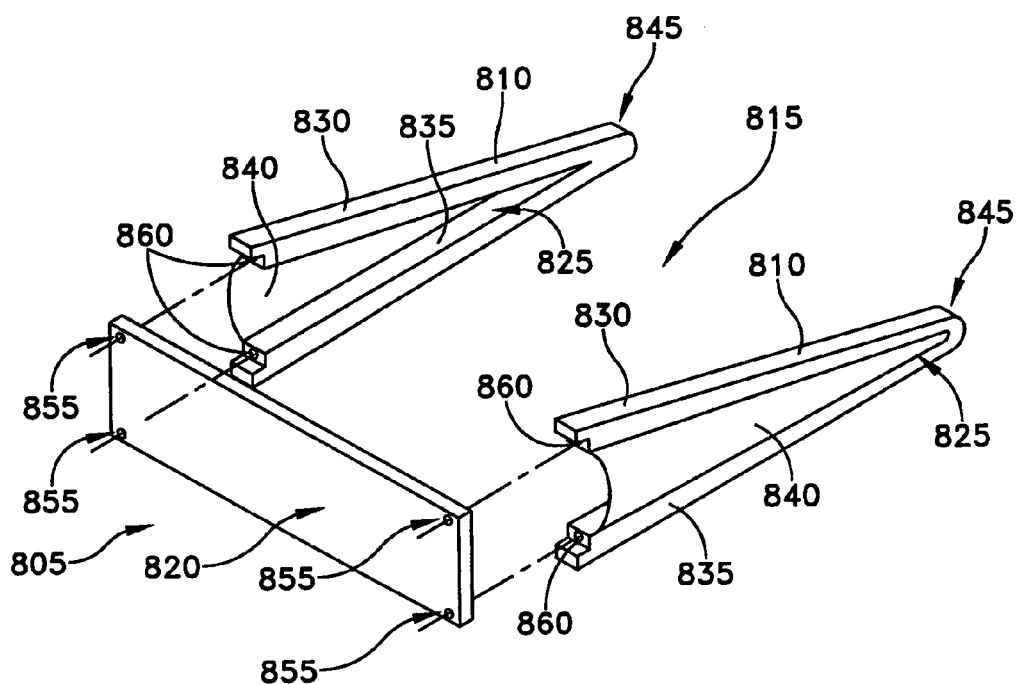
Figure 113:
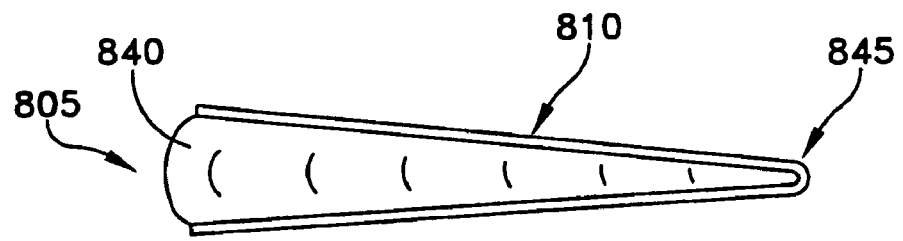
Figure 114:
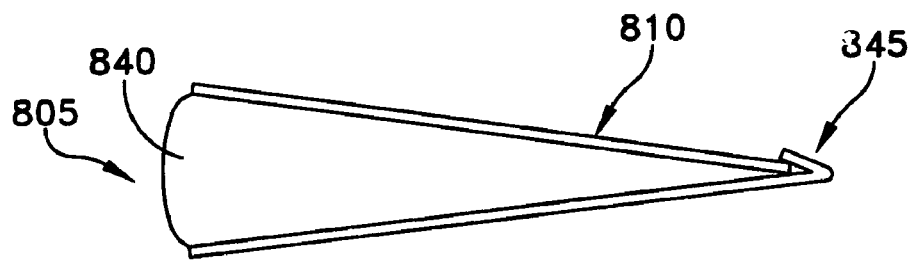
Figure 115:
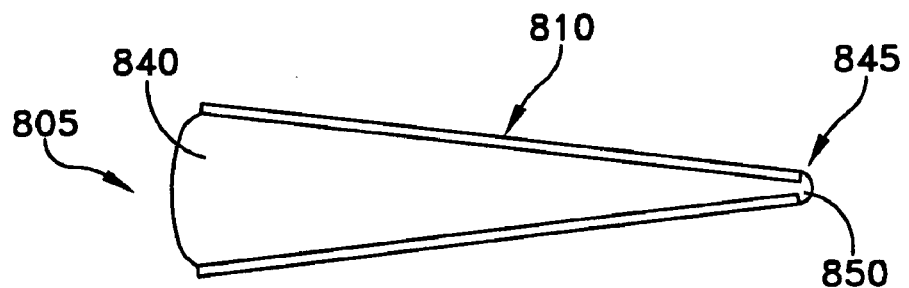

Expandable wedge implant 805 comprises two opposing sides 810 (FIG. 112) whose surfaces frame the perimeter of the bony void and preferably create an opening 815 within the perimeter of sides 810 (FIG. 112). A base side 820 fits into the opening of the wedge osteotomy and is attachable to sides 810. Each one of the sides 810 is transversely split 825 along its length to form two opposing frame members 830, 835. Opposing frame members 830, 835 of each side 810 are connected to one other with an expandable material 840, e.g., a flexible sheet of biocompatible material. When the two frame members 830, 835 are spread apart within a bony void (or are separated within a bone cut to create a bony void), the expandable material 840 forms a containment system around the perimeter of implant 805 so as to hold graft or bone filler materials within implant opening 815.

The transversely split sides 810 can be continuous in form at leading end 845 (FIG. 113); or split sides 810 can be connected or joined at leading end 845 (FIG. 114); or split sides 810 can be connected with expandable material 850 at leading end 845 (FIG. 115); or split sides 810 can be otherwise hinged at leading end 845 (e.g., with a pivot pin), etc.

Figure 116:
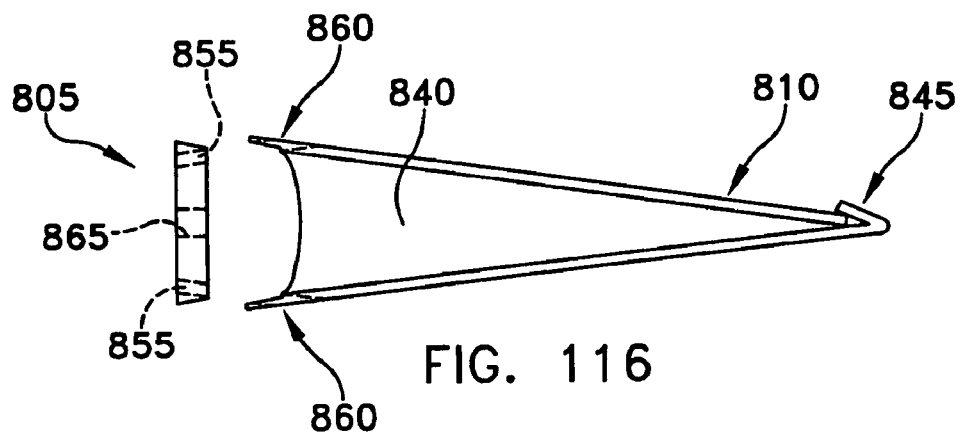

Base side 820 preferably includes passageways 855 for attachment of base side 820 to the ends 860 of transverse split sides 810 with screws, rods or other fastener (FIG. 116). Base 820 preferably also includes holes or openings 865 through which bone graft or bone filler materials can be injected or introduced (FIG. 116). Once injected or introduced, the void-filling material expands implant 805 and expandable material 840 along the perimeter of the osteotomy with the graft material inside having direct contact with the bony surfaces of the osteotomy.

Expandable material 805 is preferably manufactured from, or comprised of, any expandable biocompatible material. Expandable material 840 is preferably resorbable or osteoinductive or osteoconductive in nature.

Figure 117:
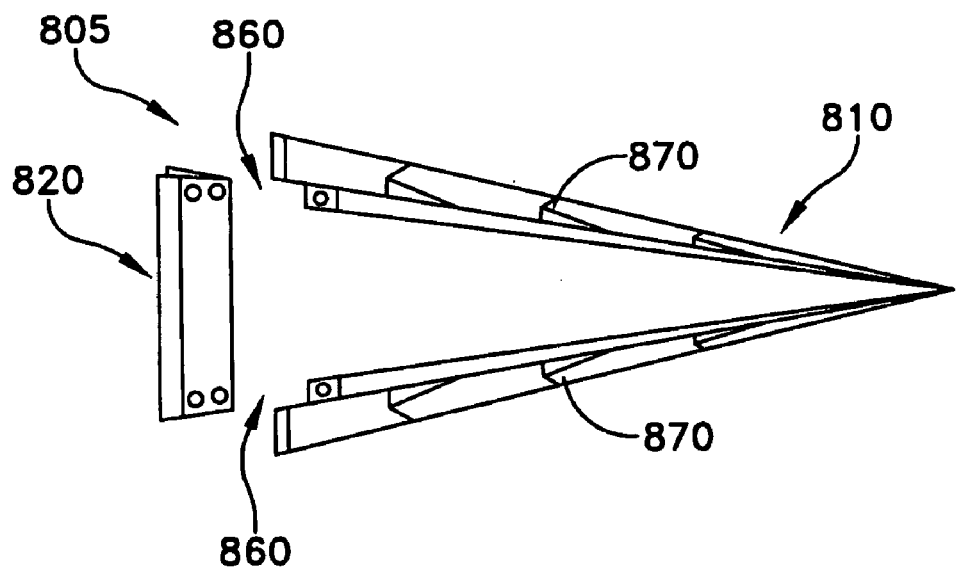

Referring now to FIG. 117, any of the expandable wedge implants 805 may incorporate projections, ridges or other protrusions 870 (hereinafter sometimes collectively referred to as "projections 870") on its bone interface surfaces. Projections 870 are shaped in such a way as to allow for easy insertion of implant 805 into the osteotomy but prevent migration of the implant once fitted into place.

The expandable wedge implants may comprise metal (e.g., titanium or stainless steel) or other biocompatible material or polymer. The selected material may be either absorbable or non-resorbable, which may also be either osteoinductive or osteoconductive.

Figure 118:
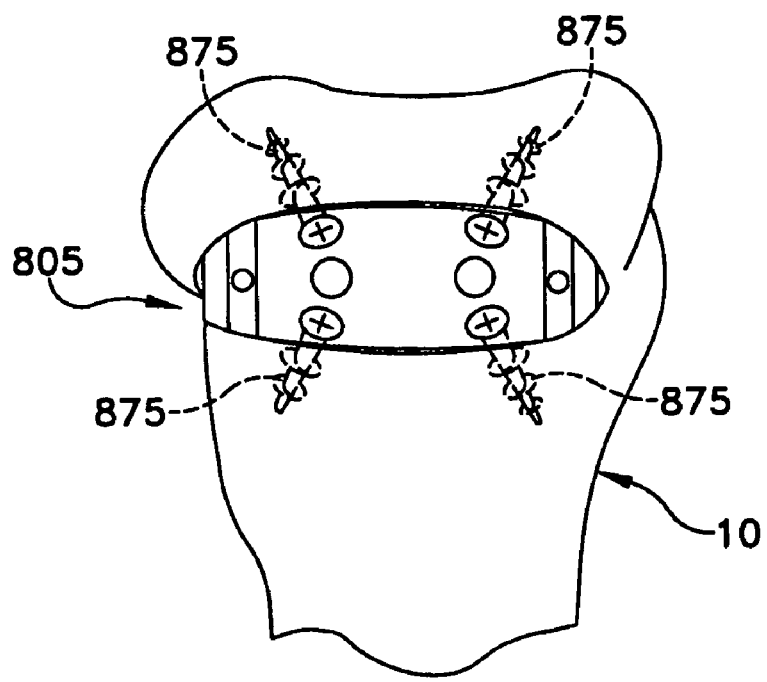

Base member 820 of expandable wedge implant 805 preferably provides secure fixation by insertion of bone screws 875 through the base and into the bone of the femur (not shown) or tibia 10 (FIG. 118). By allowing base member 820 of implant 805 to function as a secure fixation system, thereby replacing the traditional static fixation plate and bone screws, base member 820 can comprise a metal material, a biocomposite material that preferably promotes bony integration, or a combination of biocomposite materials or biocomposite material with metal in order to add strength to the eventual loading of the osteotomy site. Preferably, base member 820 is configured to provide sufficient weight bearing support and strength through the natural healing period of the osteotomy site and then begins to resorb over time, thereby preventing or reducing the effects of stress shielding of the repair and new bone growth. Such a resorbable base member 820 used in the expandable wedge implant 805 provides for active compression across the osteotomy site, thereby promoting faster and stronger healing of the osteotomy site. Also, bone screws 875 used to secure the base member may be formed of the same or similar materials as base member 820.

Figure 119:
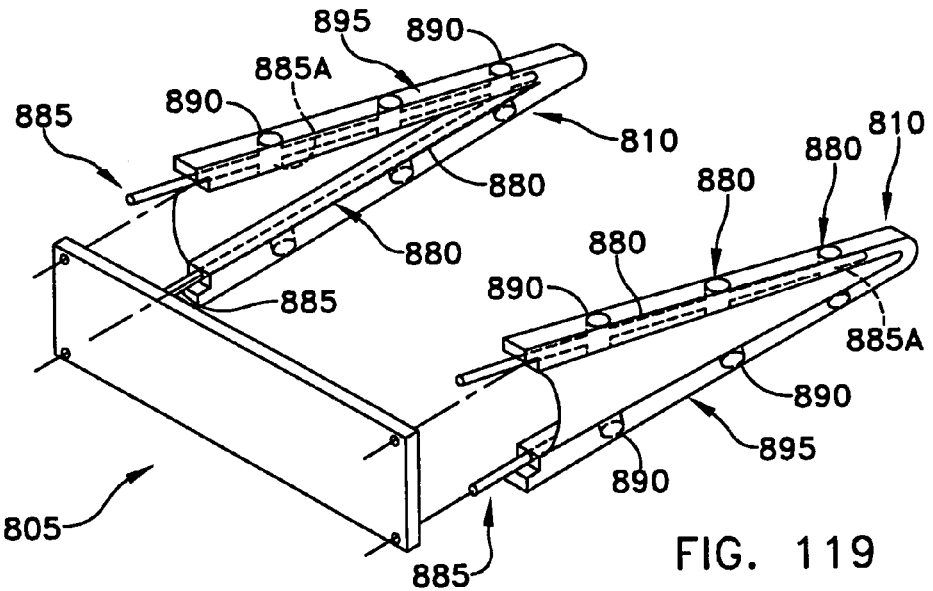
Figure 120:
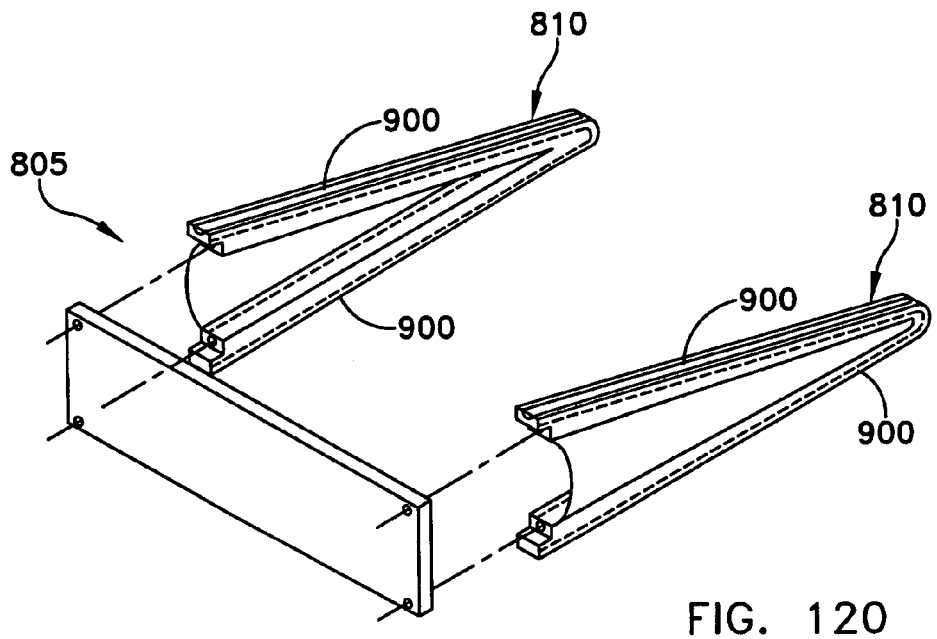

Referring now to FIGS. 119 and 120, transverse split wedge design 805 preferably also includes channels 880 through its solid material surfaces for delivering biocompatible adhesive glues, bone cements, growth factors or grafting materials. These materials are preferably resorbable. The importance of adding channels 880 is to better secure implant 805 within the osteotomy wedge void when glues or cement-like materials are delivered; and/or, in the case of adding growth factors or grafting materials, to promote the formation of bony in-growth to secure the implant.

When adding nonresorbable cements or glues to secure implant 805, it may be advantageous to allow natural cortical bone growth and new bone integration into and through the surfaces of the wedge implant; this may provide for better long-term security and stronger healing of the osteotomy site. As such, these adhesives and/or bone cement materials can be delivered through a narrow tube-like device 885 (FIG. 119) that incorporates openings 885A that align with channels 880 running to surface 890 of implant 805. Once the adhesive or cement-like material is delivered through tube device 885 into and through channels 880 to the interface of implant 805 and native bony surface of tibia 10, tube device 885 is withdrawn. Such a delivery approach provides areas of adhesion while allowing native bony contact with portions of surface 890. Also, by delivering material through tube device 885, which preferably runs the length of implant 805, and then withdrawing tube 885, more of implant 805 is allowed to integrate with new bone growth while using an efficient amount of adhesive or cement material to secure implant 805.

When using resorbable adhesives or bone cements, implant 805 is alternatively configured to have the material flow or be delivered within a cavity 900 that follows the entire contact surface between implant 805 and the bone (FIG. 120). The provision of cavity 900 provides increased strength of fixation and security. As such, after implant 805 is inserted and positioned, the adhesive material is injected/delivered into the implant/bone interface cavity 900. Base side 820 is then attached with screws or adhesive.

Osteotomy Technique Using Expandable Wedge Implant

Referring now to FIGS. 121-130, following the creation of a bone cut as described above, the surgeon chooses the properly sized expandable wedge implant trial 805A (FIG. 121), based upon the preoperative procedure described above and shown in FIGS. 35-37. Trial implant 805A is inserted into the osteotomy bone cut and the proper sized implant is determined. Trial 805A is removed and the correctly sized implant 805 (without base side 820) is inserted (FIG. 122).

Figure 126:
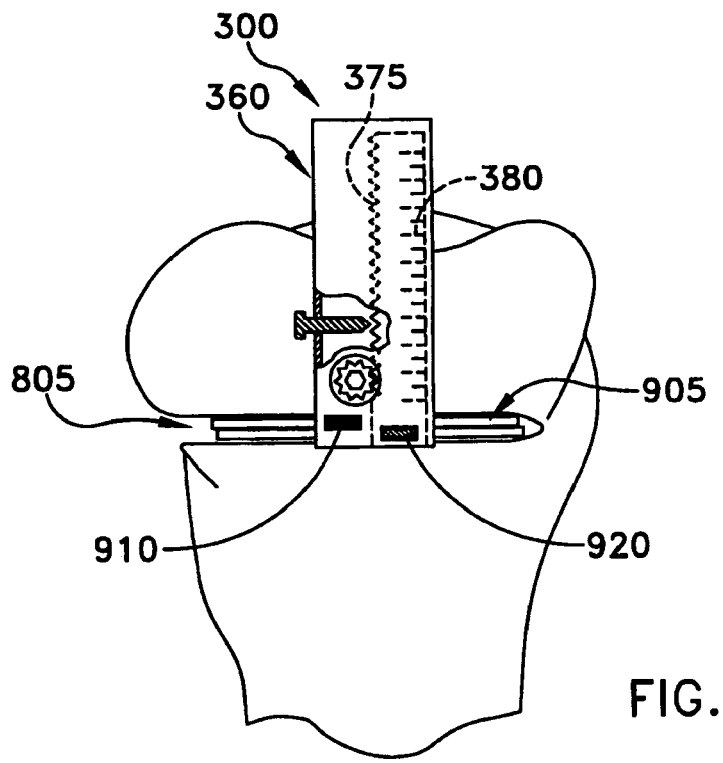
Figure 127:
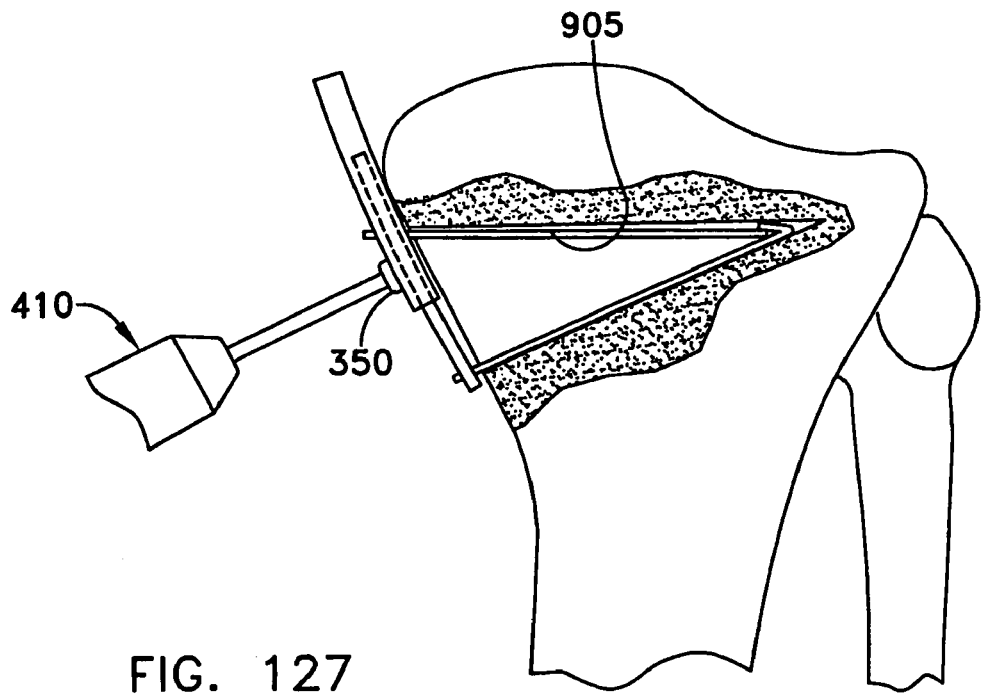
Figure 128:
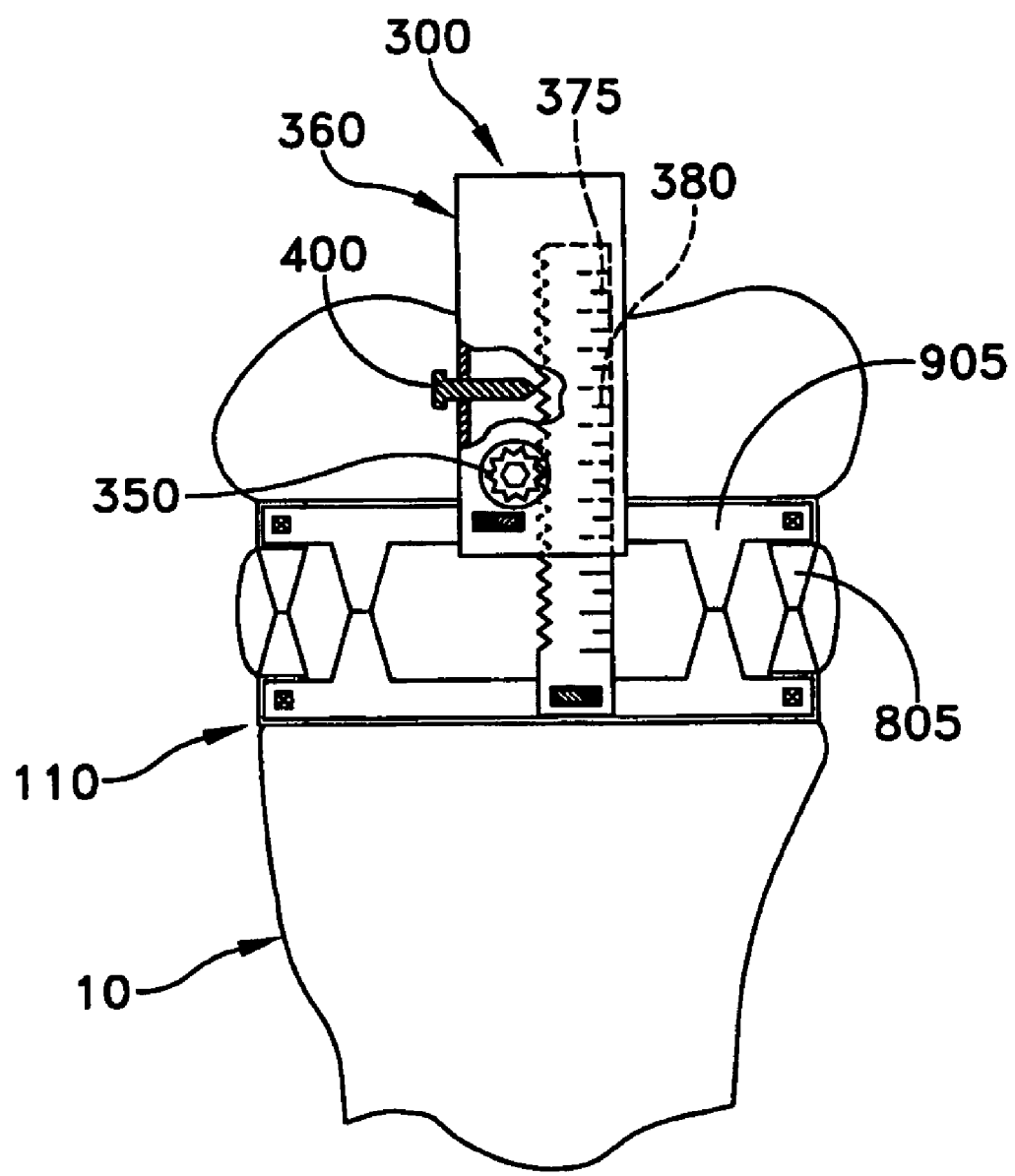
Figure 129:
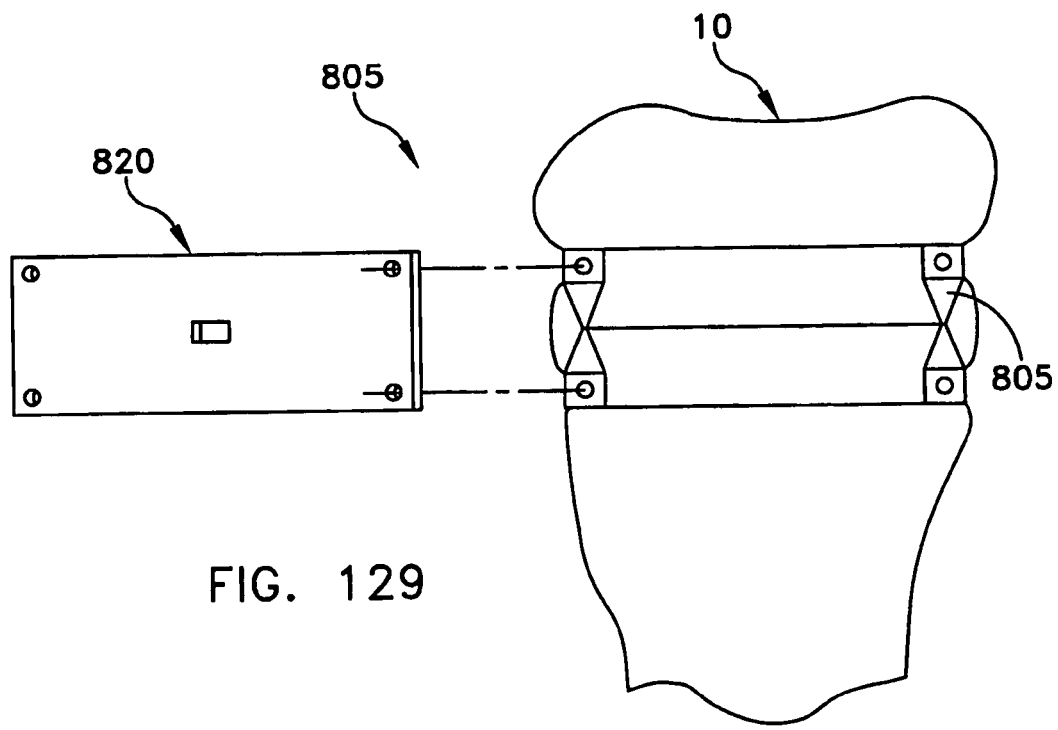
Figure 130:
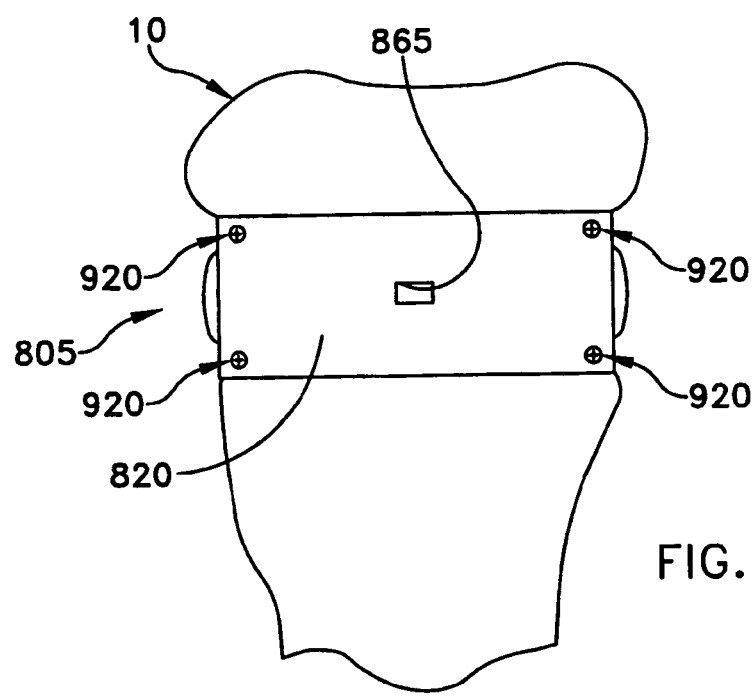

Next, the wedge opening plate 805 is assembled. An opening wedge plate device 905 is preferably provided with four attachment points 910 (FIGS. 123-125) that are designed to fit into fixation holes 915 (FIG. 122) on transverse split sides 810. Attachment points 910 provide support to allow the opening of the wedge osteotomy with implant 805 inserted therein. Plate device 905 is inserted into the bone cut with its four attachment points 910 inserted into the openings 915 at the ends of the wedge implant 805 (FIG. 124). The surgeon connects two connector portions 920 of plate device 905 to actuator housing 360 (FIG. 126). The surgeon the uses driver tool 410 to rotate actuator 350 so as to begin opening the bony wedge (FIG. 127). As the wedge is opened, the surgeon views calibrated markings 380 on sliding member 375. The wedge is opened until the desired angle is reached. Locking pin 400 is then activated so as to prevent movement of sliding member 375 (FIG. 128). With the actuator housing 360 still in place, the preferred bone graft material is then introduced into bony wedge void 110. When void 110 is almost filled with material, actuator 350 is unlocked, and rotated so as to slightly loosen corrective device 300. Actuator housing 360 is then removed from plate device 905, being careful not to remove the graft material. The appropriately-sized base wall 820 for wedge implant 805 is then chosen and fit into the wedge opening (FIG. 129). Base wall 820 is then secured to side walls 810 through the use of threaded fasteners 920. Additional bone graft material may then be introduced through openings 865 of base wall 820 of wedge 805 and the bony void is further filled (FIG. 130).

Stabilization is achieved with expandable wedge implant device 805 at the osteotomy site while maintaining the corrective angle. By allowing the direct contact of bone graft material with the bony cut surface of the osteotomy, within the perimeter of the expandable wedge implant, the necessary physiologic compression and stimulation required to promote new tissue and bone growth through the bony void is provided.

It is to be understood that the present invention is by no means limited to the particular constructions herein disclosed and/or shown in the drawings, but also comprises any modifications or equivalents within the scope of the invention.

What is claimed is:

1. A method for performing an open wedge osteotomy in a tibia comprising:
    providing a system for performing the open wedge osteotomy in the tibia, the system comprising:
        a positioning guide having an alignment component for aligning a top portion of the positioning guide with a tibial plateau of the tibia, and having fixation bores for attaching selected devices to the positioning guide;
        a cutting guide having a guide attachment component for selectively attaching the cutting guide to the positioning guide;
        protector member for protecting soft tissue during cutting;
        a mechanical jack having a jack attachment component for selectively attaching the jack to the positioning guide, the mechanical jack having a pair of opposed plates each with first ends configured to remain substantially adjacent to one another and second ends of the pair of plates being configured for selective positioning (i) from a first position to (ii) a second position to form the open wedge osteotomy in the tibia; and
        an implant for deployment in the open wedge osteotomy in the tibia;
    aligning the positioning guide with a joint line of the tibia using the alignment component;
    fixing the positioning guide to the tibia using a fixation component;
    attaching the guide attachment component of the cutting guide to the positioning guide to position an angled cutting slot in a predetermined orientation with the joint line of the tibia;
    moving a cutting blade through the angled cutting slot of the cutting guide to form the cut in the tibia;
    attaching the mechanical jack to the positioning guide;
    positioning the first ends of the pair of plates of the mechanical jack in the cut, the pair of plates having their second ends in the first position with the second ends of the pair of plates being substantially adjacent;
    actuating the mechanical jack to move the second ends of the pair of plates from the first position to the second position with the second ends of the pair of plates apart from one another to distract the tibia at the cut and provide the open wedge osteotomy in the tibia; and
    inserting the implant into the tibia to support the open wedge osteotomy in the tibia.

2. A method for performing an open wedge osteotomy in a tibia according to claim 1 wherein the alignment component comprises a top surface of the positioning guide, and further wherein the step of aligning the positioning guide with the joint line of the tibia comprises aligning the top surface of the positioning guide with the joint line of the tibia.

3. A method for performing an open wedge osteotomy in a tibia according to claim 1 wherein the fixation component comprises two fixation screws and the positioning guide forms two fixation screw holes therein configured to receive each of the two fixation screws therethrough, respectively, and further wherein the step of fixing the positioning guide to the tibia comprises attaching each of the two fixation screws through the positioning guide into the tibia.

4. A method for performing an open wedge osteotomy in a tibia according to claim 1 wherein the cutting guide is provided with a passageway therethrough, wherein the guide attachment component comprises a connection screw selectively disposed through the passageway to anchor the cutting guide to the tibia, and wherein the step of attaching the cutting guide to the positioning guide comprises positioning the cutting guide adjacent the positioning guide, positioning the connection screw through the passageway of the cutting guide, and threadably engaging the connection screw with the positioning guide.

5. A method for performing an open wedge osteotomy in a tibia according to claim 1 wherein the step of actuating the mechanical jack to move the second ends of the pair of plates from the first position to the second position with the second ends of the pair of plates apart from one another, further comprises the step of reading calibrations disposed on the mechanical jack so as to distract the tibia at the cut to a given distance as indicated by the calibrations.

6. A method for performing an open wedge osteotomy in a tibia according to claim 1 wherein the implant comprises a multi-part implant for deployment in the open wedge osteotomy in the tibia, the multi-part implant having a first component for disposition in a posterior portion of the open wedge osteotomy, a second component for disposition in an anterior portion of the open wedge osteotomy, and a connection device for selectively connecting the first component and the second component to one another, the implant having channels extending therethrough and in communication with injection ports and with outlets disposed adjacent the tibia.

7. A method for performing an open wedge osteotomy in a tibia according to claim 6 wherein the step of inserting the multi-part implant into the tibia further comprises the step of assembling the implant in-situ so as to provide a minimally invasive surgical procedure.

8. A method for performing an open wedge osteotomy in a tibia according to claim 6 wherein the step of inserting the multi-part implant into the tibia further comprises the step of assembling the implant outside of the open wedge osteotomy.

9. A method for performing an open wedge osteotomy in a tibia according to claim 1 further comprising interposing the protector members between the tibia and soft tissue.

10. A method for performing an open wedge osteotomy in a tibia according to claim 9, wherein the first protector member is placed on an anterior side of the tibia and the second protector member is placed on a posterior side of the tibia.

11. A method for performing an open wedge osteotomy in a tibia comprising:
    providing a system for performing the open wedge osteotomy in a tibia, the system comprising:
        a cutting guide having a guide attachment component for selectively attaching the cutting guide to the tibia;
        a first protector member;

a second protector member;

a mechanical jack having a pair of opposed plates, first ends of the pair of plates being configured to remain substantially adjacent to one another, and second ends configured for selective positioning from (i) a first position to (ii) a second position to distract the tibia at the cut; and an implant for supporting the open wedge osteotomy in the tibia;

aligning the cutting guide with a joint line of the tibia;

attaching the cutting guide to the tibia to position an angled cutting slot in a predetermined orientation with the joint line of the tibia;

attaching the first protector member to a first side of the cutting guide; attaching the second protector member to a second side of the cutting guide;

positioning a cutting blade through the angled cutting slot of the cutting guide to form a cut in the tibia;

positioning the first ends of the pair of plates of the mechanical jack into the cut in the tibia, the pair of plates having their second ends in the first position with the second ends of the pair of plates substantially adjacent;

actuating the mechanical jack to move the second ends of the pair of plates from the first position to the second position to create a wedge-shaped void in the tibia; and inserting the implant into the wedge-shaped void in the tibia.

12. A method for performing an open wedge osteotomy in a tibia according to claim 11, wherein the first protector member is positioned on the anterior side of the tibia and the second protector member is positioned on the posterior side of the tibia to protect soft tissue during a tibial cutting operation, wherein a connector portion of the first protector member and a connector portion of the second protector member are configured to selectively attach directly to the tibia using fixation screws to anchor the first protector member and the second protector member to the tibia, respectively, wherein a first alignment reference on the first protector member and a second alignment reference on the second protector member allow alignment of the first protector member and the second protector member with a joint line of the tibia, the method comprising aligning the first protector member and the second protector member with the joint line of the tibia, and attaching the first protector member and the second protector member to the tibia to provide a first attachment site defined by the first protector member and a second attachment site defined by the second protector member, and attaching the cutting guide to the tibia comprises attaching the cutting guide based on locations of the first attachment site and the second attachment site.

13. A method for performing an open wedge osteotomy in a tibia according to claim 11, wherein the implant comprises a multi-part implant for supporting the open wedge osteotomy in the tibia, the multi-part implant having a first component for disposition in a posterior portion of the open wedge osteotomy, a second component for disposition in an anterior portion of the Open wedge osteotomy, and a connection device for selectively connecting the first component and the second component to one another, the implant having channels extending therethrough and in communication with injection ports and with outlets disposed proximate the tibia.

* * * * *